United States Patent [19]
Lee et al.

[11] Patent Number: 5,627,908
[45] Date of Patent: May 6, 1997

[54] METHOD FOR CYTOLOGICAL SYSTEM DYNAMIC NORMALIZATION

[75] Inventors: Shih-Jong J. Lee, Bellevue; Alan C. Nelson, Redmond; Larry A. Nelson, Bellevue; Carl E. Youngmann; Keith L. Frost, both of Seattle, all of Wash.

[73] Assignee: NeoPath, Inc., Redmond, Wash.

[21] Appl. No.: 309,063

[22] Filed: Sep. 20, 1994

[51] Int. Cl.$^6$ .................. G06K 9/00; G06K 9/38
[52] U.S. Cl. ................... 382/133; 382/128; 382/270
[58] Field of Search ...................... 382/133, 170, 382/172, 129, 134, 270, 275, 215, 274, 272, 159, 160, 128; 356/39, 42; 377/10; 364/413.1

[56] References Cited

U.S. PATENT DOCUMENTS

| | | | |
|---|---|---|---|
| 3,705,383 | 12/1972 | Frayer | 377/10 |
| 3,824,393 | 7/1974 | Brain . | |
| 3,908,078 | 9/1975 | Auerbach et al. | 364/413.1 |
| 3,916,176 | 10/1975 | Alien et al. | 377/10 |
| 3,999,047 | 12/1976 | Green | 382/172 |
| 4,034,342 | 7/1977 | Kruklitis . | |
| 4,175,860 | 11/1979 | Bacus . | |
| 4,706,207 | 11/1987 | Hennessy et al. | 364/413.08 |
| 4,965,725 | 10/1990 | Rutenberg | 382/159 |
| 5,029,226 | 7/1991 | Klein et al. . | |
| 5,068,788 | 11/1991 | Goodenough et al. | 382/172 |
| 5,072,382 | 12/1991 | Kamentsky . | |
| 5,073,857 | 12/1991 | Peters et al. | 382/128 |
| 5,257,182 | 10/1993 | Luck et al. . | |
| 5,287,272 | 2/1994 | Rutenberg et al. | 382/159 |
| 5,313,532 | 5/1994 | Harvey et al. | 382/159 |
| 5,315,700 | 5/1994 | Johnston et al. . | |
| 5,361,140 | 11/1994 | Hayenga et al. . | |

OTHER PUBLICATIONS

Tanaka, Noboru et al., Automated cytologic screening (CYBEST model 4), Applied Optics vol. 26, No. 16, pp. 3301–3307 Aug. 15, 1987.

Cseke, Istvan, A Fast Segmentation Scheme for White Blood Cell Images, IEEE 0–8186–2920–Jul. 1992.

Bacus, James W. and Les J. Grace, "Optical Microscope System For Standardized Cell Measurements and Analyses", *Applied Optics*, 26:16, pp. 3280–3293, 15 Aug. 1987.

Bartels, Peter H., et al., "A Self–Learning Computer Program for Cell Recognition", *ACTA Cytologica: The Journal of Clinical Cytology*, 14:8, pp. 486–494, Oct. 1970.

Tanaka, Noboru, et al., "Automated Cytologic Screening System (CYBEST Model 4): an Integrated Image Cytometry System", Reprinted from *Applied Optics*, vol. 26, No. 16, pp. 3301–3307, Aug. 15, 1987. Copyright© 1987 by the Optical Society of America and reprinted by permission of the copyright owner.

Duda, Richard O. and Peter E. Hart, "Fisher's Linear Discriminant", *Patent Classification and Scene Analysis*, Copyright ©1973, pp. 114–119.

Dytch, Harvey E. et al., "An Interactive Microcomputer–Based System for the Quantitative Analysis of Stratified Tissue Sections", *Analytical and Quantitative Cytology and Histology*, vol. 9, No. 1, pp. 69–78, Mar. 1987.

(List continued on next page.)

*Primary Examiner*—Leo Boudreau
*Assistant Examiner*—Brian L. Johnson
*Attorney, Agent, or Firm*—Hans I. Sun; Emil Moffa

[57] ABSTRACT

A cytological system dynamic normalization of a normal threshold. An analysis score from a slide is compared against a threshold to determine whether or not the slide is normal or requires microscopy review. The normal threshold is dynamically adjusted using a three step process. The process is implemented on an automatic cytology system. The first step is initial calibration of the system to determine an initial threshold. The second step is a running adjustment of the normal threshold in response to the presentation of new slides to the automatic cytology system. The third step is the batch certification of every slide. The threshold may be adjusted for an analysis score, a quality control score, or a screening score.

25 Claims, 41 Drawing Sheets

OTHER PUBLICATIONS

Enslein, Kurt and Peter W. Neurath, "Augmented Stepwise Discriminant Analysis Applied to Two Classification Problems in the Biomedical Field", *Computers and Biomedical Research*, 2, 568–581 (1969).

Kurman, Robert J. et al., "Part 1: Specimen Adequacy" and Part 2: Descriptive Diagnoses, *The Bethesda System for Reporting Cerivcal–Vaginal Cytologic Diagnoses*, Springer–Verlag.

Smith, Warren J., "Modern Optical Engineering: The Design of Optical Systems", Copyright ©1966 by McGraw–Hill Book Company, pp. 308–325.

Weber, J.E. et al., "Fuzzy Reasoning, Possibility Theory and Probability Theory in Expert Systems for Histopathology", IEEE/Ninth Annual Conference of the Engineering in Medicine and Biology Society, pp. 1560–1562, ©1987.

Wied, G.L. et al., "Expert Systems as Classifiers in Diagnostic Cytopathology", IEEE/Ninth Annual Conference of the Engineering in Medicine and Biology Society, pp. 1915–1917, ©1987.

Wied, G.L. et al., "Expert System Design Under Uncertainty of Human Diagnosticians", IEEE/Eighth Annual Conference of the Engineering in Medicine and Biology Society, pp. 757–760, ©1986.

Wied, G.L. et al., "Ticas–Stratex, an Expert Diagnostic System For Stratified Cervical Epithelium", IEEE/Ninth Annual Conference of the Engineering in Medicine and Biology Society, pp. 1557–1559. ©1987.

Serra, J., *Image Analysis and Mathematical Morphology*, pp. 372–423, Academic Press, 1982.

Smith, "Image Evaluation", *Modern Optical Engineering*, McGraw–Hill Book Company, 1966, pp. 308–323.

Patten, Jr., Stanley, "Diagnostic Cytopathology of the Uterine Cervix", Basel, Switzerland, Publisher: S. Karger, 1969, 2nd Edition 1978, Third vol. in *Monographs in Clinical Cytology*, edited by G.L. Wied, pp. 10–15.

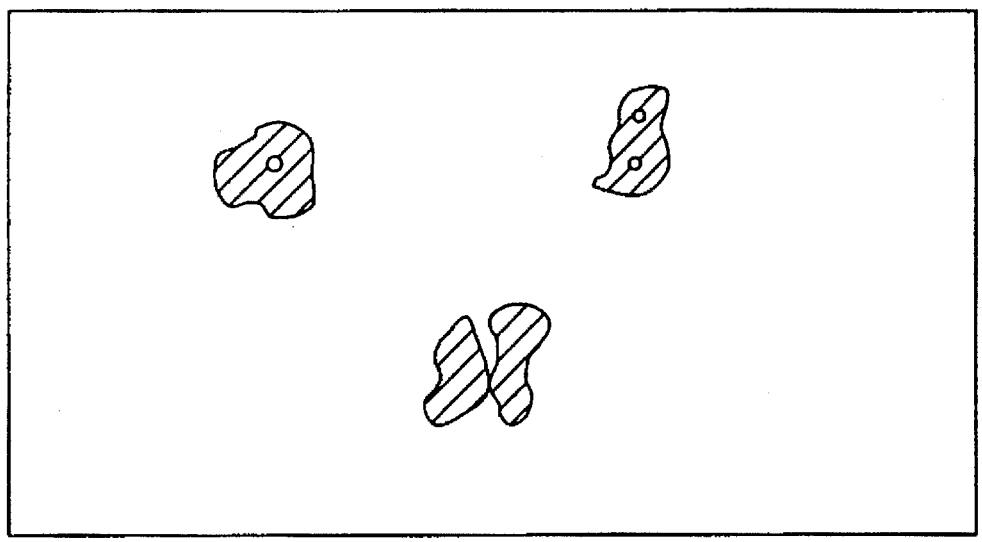
Fig_15A
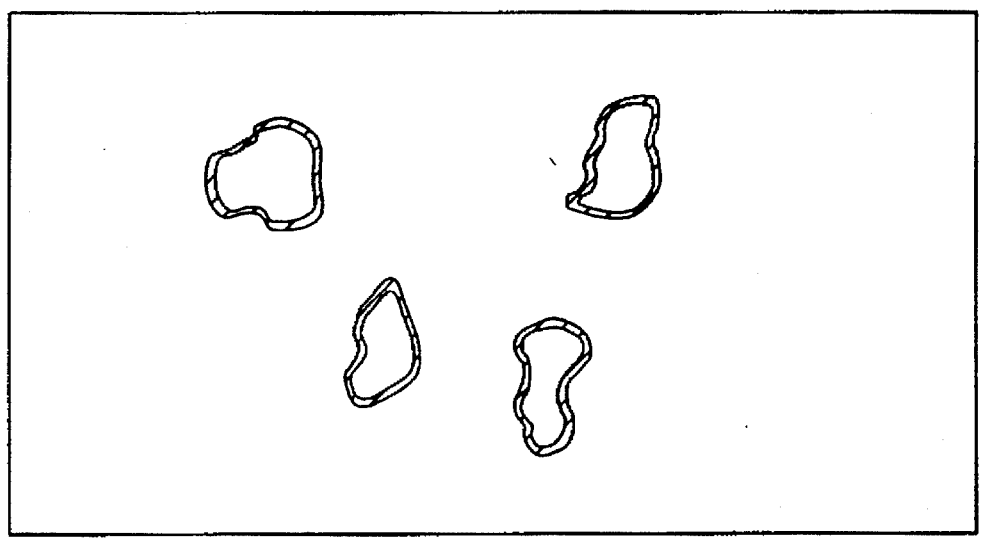
Fig_15B

Fig_24

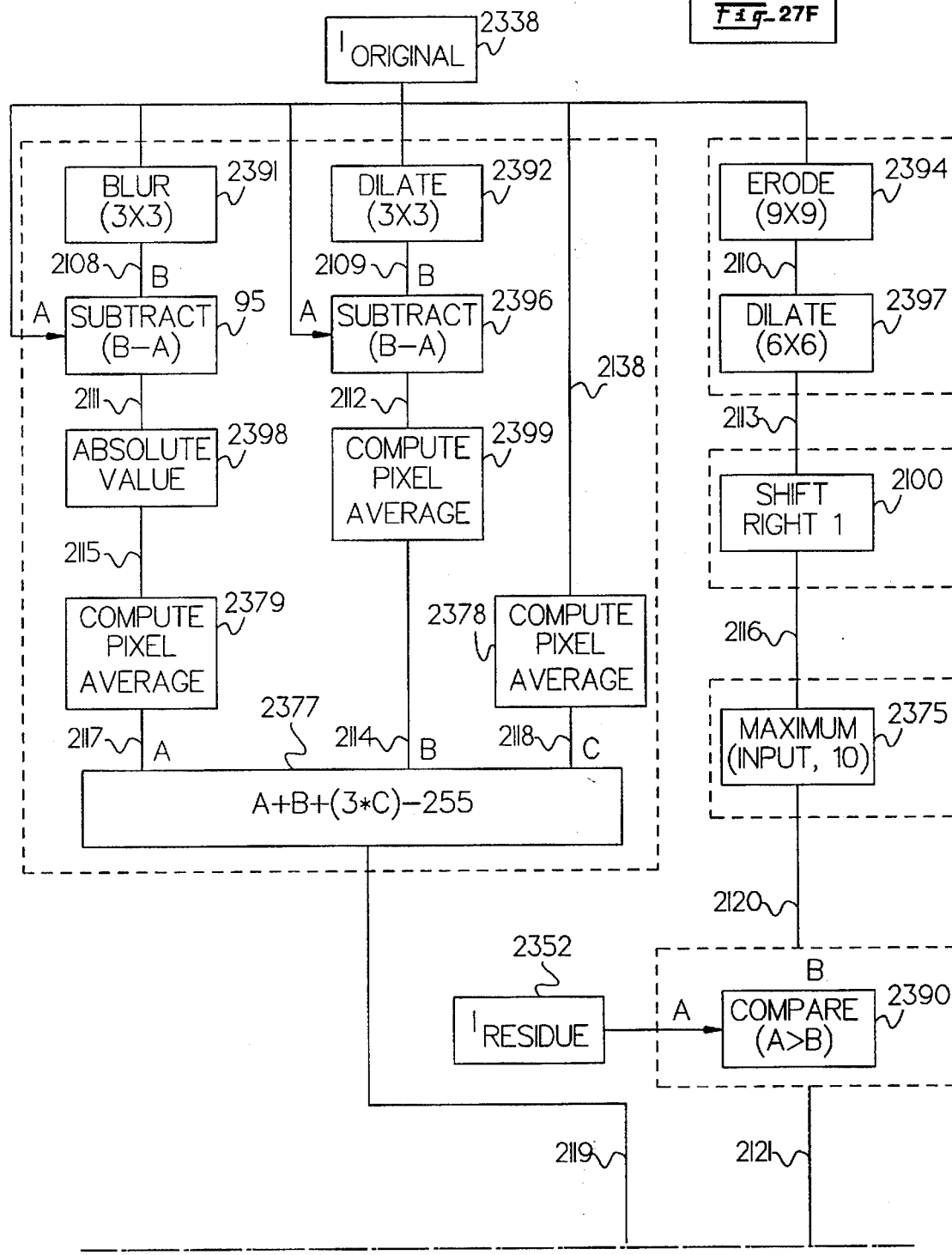

Fig_31

METHOD FOR CYTOLOGICAL SYSTEM DYNAMIC NORMALIZATION

BACKGROUND OF THE INVENTION

This invention relates to a cytological specimen classifier, more particularly to a method for dynamically normalizing decision variations concerning biological specimens.

BACKGROUND OF THE INVENTION

Conventional Pap smears prepared in accordance with Papanicolaou staining procedures have characteristics that vary a great deal from smear to smear. Some of these variations are caused by patient population differences. As an example, labs having slides from sexually transmitted disease clinics will normally have a higher percentage of abnormal slides. A normal slide from this population may have a higher occurrence of benign cellular change or inflammatory conditions. Other significant sources of variations are specimen sampling and preparation. Also, the Papanicolaou staining procedure may be subject to a wide variety of variations in staining recipe, staining material, staining batches, etc. These preparation variations are found as inter-lab differences as well as intra-lab staining batch differences.

Machines that automate or semi-automate cervical smear screening typically generate an analysis score for each screened slide. The higher the analysis score, the more likely the slide is from a patient with an abnormality. The score is sensitive to the above variations. Normal slides with darker cell staining are more likely to have higher analysis scores. An automated cervical smear screening system with a fixed analysis score threshold typically yields different performance operating points, such as normal slide specificity and abnormal slide sensitivity, for slides from different labs or different batches from the same lab. Such inconsistencies lead to inconsistent classification results.

Until the present invention, the problems arising from the above described specimen variations remained unsolved. As a result, no automated or semi-automated cervical smear screener has been proven to be effective in screening Pap smears. Attempts have been made to standardize Papanicolaou sampling, preparation, and staining processes. However, such standardization methods increase costs of automated or semi-automated Pap screeners and have the further undesirable requirement of altering standard lab practice.

Therefore, it is a motive of the invention to provide a dynamic normalization method and apparatus that dynamically adjusts the anomaly score threshold based on the specimen population.

SUMMARY OF THE INVENTION

The invention provides a dynamic normalization method and apparatus comprising three stages of processing. An initial calibration stage normalizes inter-lab variations. A continuous parameter adjustment stage normalizes the intra-lab batch variations. A batch certification stage assures the integrity of the dynamic normalization process. The initial calibration process is performed during system installation. The running adjustment stage provides calibration slides which have stable characteristics and are used as a basis for a running adjustment. The calibration slides are provided in batches including a short term batch, a mid term batch, and a long term batch. The batches represent the amount of time that has lapsed since calibration slide processing.

In one aspect of the invention, the short term batch represents 300 calibration slides most recently processed. The mid term batch represents 600 calibration slides processed prior to the processing of the short term slides, and the long term batch represents the 1200 calibration slides processed prior to the processing of the midterm slides. The dynamic normalization process contains a batch certification stage to ensure the integrity of the dynamic calibration process. Weighted probabilities are used to reject or qualify the batch.

It is one object of the invention to provide continuous lab and system certifications.

It is another object of the invention to provide a practical solution to compensate for the specimen variations without altering the current practice in specimen preparations.

It is another object of the invention to provide information to monitor lab staining and population variations for lab process quality control.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIGS. 15A and 15B are diagrams illustrating a portion of the method for refining objects of interest.

DETAILED DESCRIPTION OF THE PREFERRED EMBODIMENT

Figure 1A:
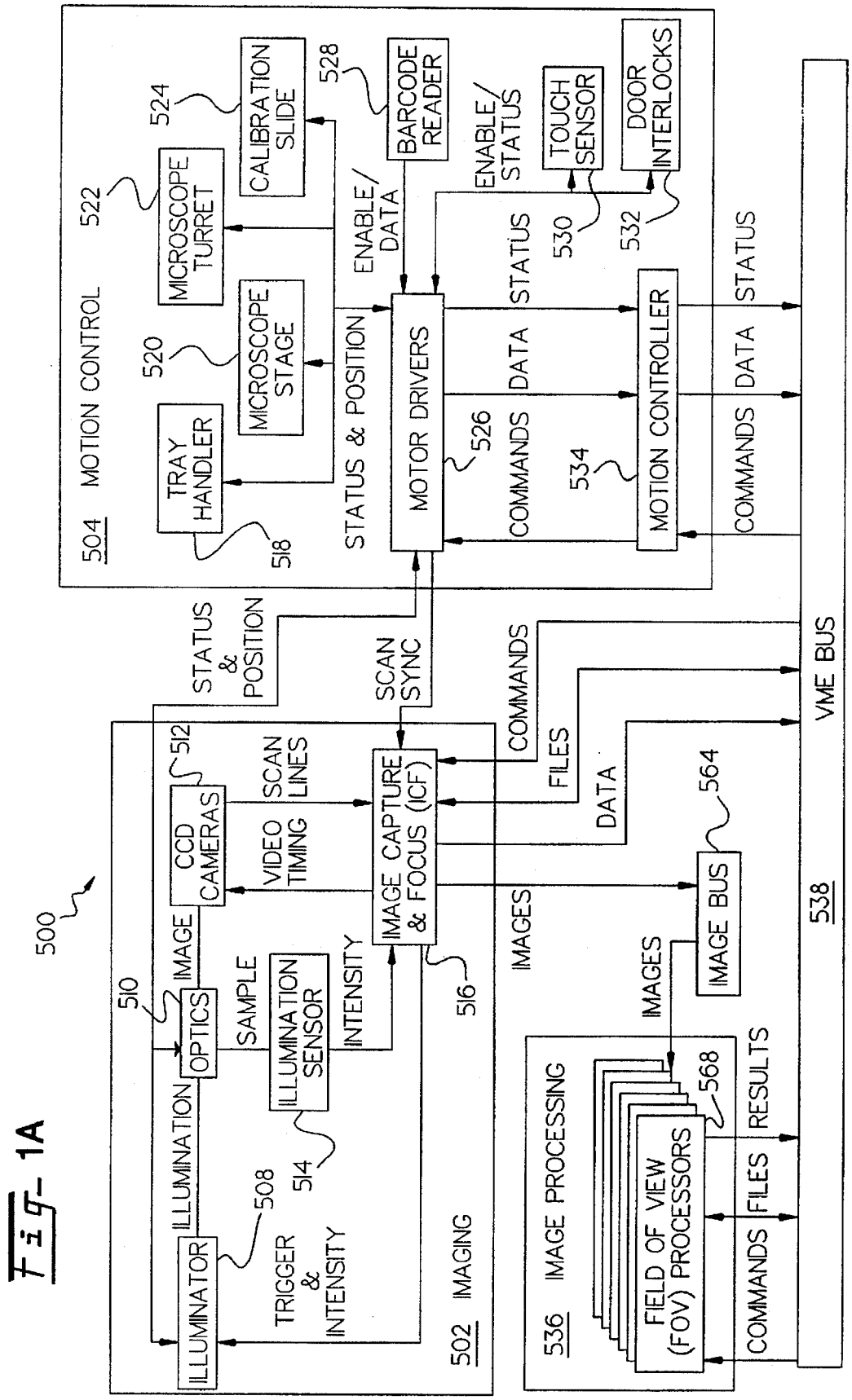
FIGS. 1A and 1B show a schematic diagram of the cytological system dynamic normalization apparatus of the invention.

In a presently preferred embodiment of the invention, the system disclosed herein is used in a system for analyzing cervical pap smears, such as that shown and disclosed in pending U.S. patent application Ser. No. 08/571,686, filed Dec. 13, 1995, a continuation of abandoned U.S. patent application Ser. No. 07/838,064, entitled "Method For Identifying Normal Biomedical Specimens", by Alan C. Nelson, et al., filed Feb. 18, 1992; U.S. Pat. No. 5,528,703 which is a continuation in part of abandoned U.S. patent application Ser. No. 07/838,395, entitled "Method For Identifying Objects Using Data Processing Techniques", by S. James Lee et al., filed Feb. 18, 1992; U.S. Pat. No. 5,315,700, entitled "Method And Apparatus For Rapidly Processing Data Sequences", by Richard S. Johnston et al., filed Feb. 18, 1992; U.S. Pat. No. 5,361,140, entitled "Method and Apparatus for Dynamic Correction of Microscopic Image Signals" by Jon W. Hayenga, et al.; and pending U.S. patent application Ser. No. 08/302,355, filed Sep. 7, 1994 entitled "Method and Apparatus for Rapid Capture of Focused Microscopic Images" to Hayenga et al., which is a continuation-in-part of abandoned application Ser. No. 07/838,063 filed on Feb. 18, 1992 the disclosures of which are incorporated herein, in their entirety, by the foregoing references thereto.

The present invention is also related to biological and cytological systems as described in the following patent applications which are assigned to the same assignee as the present invention, filed on Sep. 20, 1994 unless otherwise noted, and which are all hereby incorporated by reference including pending U.S. patent application Ser. No. 08/309,118, to Kuan et al. entitled, "Field Prioritization Apparatus and Method," pending U.S. patent application Ser. No. 08/309,061, to Wilhelm et al., entitled "Apparatus for Automated Identification of Cell Groupings on a Biological Specimen," pending U.S. patent application Ser. No. 08/309,116 to Meyer et al. entitled "Apparatus for Automated Identification of Thick Cell Groupings on a Biological Specimen," pending U.S. patent application Ser. No. 08/309,115 to Lee et al. entitled "Biological Analysis System Self Calibration Apparatus," pending U.S. patent application Ser. No. 08/309,063 to Lee et al. entitled "Method for Cytological System Dynamic Normalization," pending U.S. patent application Ser. No. 08/309,248 to Rosenlof et al. entitled "Method and Apparatus for Detecting a Microscope Slide Coverslip," pending U.S. patent application Ser. No. 08/309,077 to Rosenlof et al. entitled "Apparatus for Detecting Bubbles in Coverslip Adhesive," pending U.S. patent application Ser. No. 08/309,931, to Lee et al. entitled "Cytological Slide Scoring Apparatus," pending U.S. patent application Ser. No. 08/309,148 to Lee et al. entitled "Method and Apparatus for Image Plane Modulation Pattern Recognition," pending U.S. patent application Ser. No. 08/309,250 to Lee et al. entitled "Apparatus for the Identification of Free-Lying Cells," pending U.S. patent application Ser. No. 08/309,209 to Oh et al. entitled "A Method and Apparatus for Robust Biological Specimen Classification," pending U.S. patent application Ser. No. 08/309,117, to Wilhelm et al. entitled "Method and Apparatus for Detection of Unsuitable Conditions for Automated Cytology Scoring."

It is to be understood that the various processes described herein may be implemented in software suitable for running on a digital processor. The software may be embedded, for example, in the central processor 540.

Figure 1B:
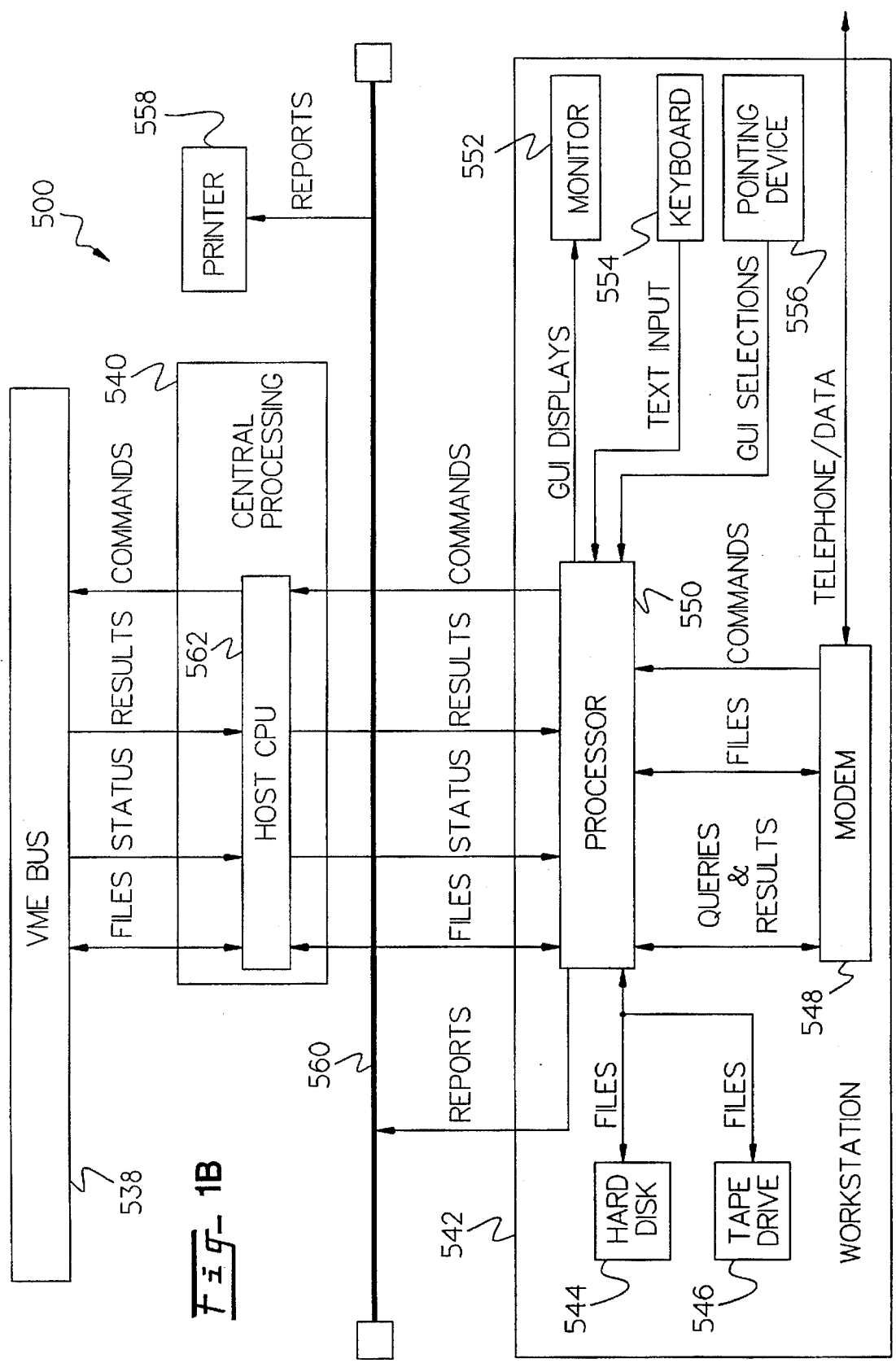
Figure 1C:
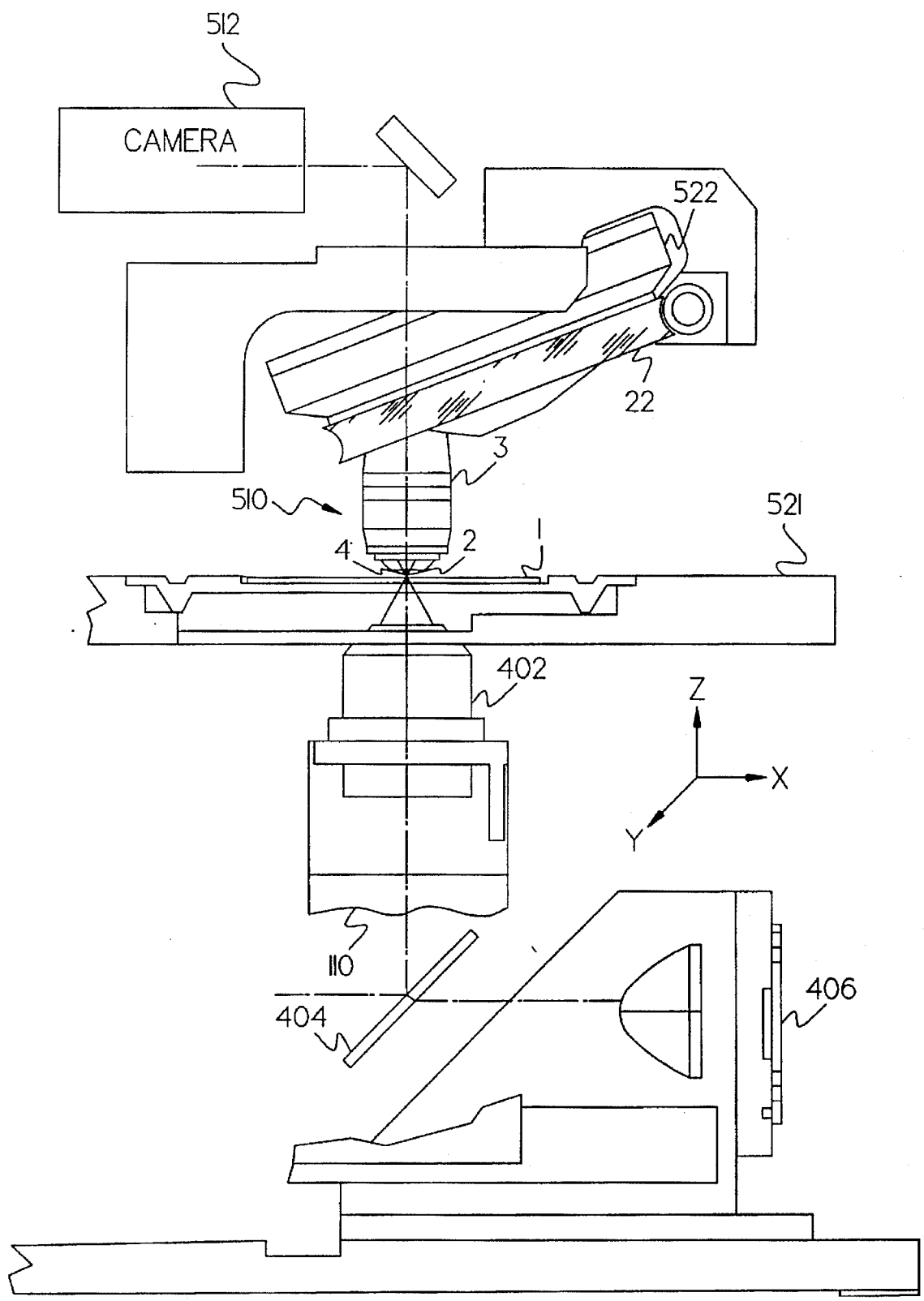
FIG. 1C schematically shows an automated microscope of the type used in automated cytological system having a calibration slide mounted on a movable stage.

Now refer to FIGS. 1A, 1B and 1C which show a schematic diagram of one embodiment of the apparatus of the invention for field of view prioritization. The apparatus of the invention comprises an imaging system 502, a motion control system 504, an image processing system 536, a central processing system 540, and a workstation 542. The imaging system 502 is comprised of an illuminator 508, imaging optics 510, a CCD camera 512, an illumination sensor 514 and an image capture and focus system 516. The image capture and focus system 516 provides video timing data to tile CCD cameras 512, the CCD cameras 512 provide images comprising scan lines to the image capture and focus system 516. An illumination sensor intensity is provided to the image capture and focus system 516 where an illumination sensor 514 receives the sample of the image from the optics 510. In one embodiment of the invention, the optics may further comprise an automated microscope 511. The illuminator 508 provides illumination of a slide. The image capture and focus system 516 provides data to a VME bus 538. The VME bus distributes the data to an image processing system 536. The image processing system 536 is comprised of field of view processors 568. The images are sent along the image bus 564 from the image capture and focus system 516. A central processor 540 controls the operation of the invention through the VME bus 538. In one embodiment the central processor 562 comprises a Motorola 68030 CPU. The motion controller 504 is comprised of a tray handler 518, a microscope stage controller 520, a microscope tray controller 522, and a calibration slide 524. The motor drivers 526 position the slide under the optics. A bar code reader 528 reads a barcode located on the slide 524. A touch sensor 530 determines whether a slide is under the microscope objectives, and a door interlock 532 prevents operation in case the doors are open. Motion controller 534 controls the motor drivers 526 in response to the central processor 540. An Ethernet communication system 560 communicates to a workstation 542 to provide control of the system. A hard disk 544 is controlled by workstation 550. In one embodiment, workstation 550 may comprise a Sun Spark Classic (TM) workstation. A tape drive 546 is connected to the workstation 550 as well as a modem 548, a monitor 552, a keyboard 554, and a mouse pointing device 556. A printer 558 is connected to the ethernet 560.

During identification of multiple cell patterns, the central computer 540, running a real time operating system, controls the microscope 511 and the processor to acquire and digitize images from the microscope 511. The flatness of the slide may be checked, for example, by contacting the four corners of the slide using a computer controlled touch sensor. The computer 540 also controls the microscope 511 stage to position the specimen under the microscope objective, and from one to fifteen field of view (FOV) processors 568 which receive images under control of the computer 540.

Figure 1D:
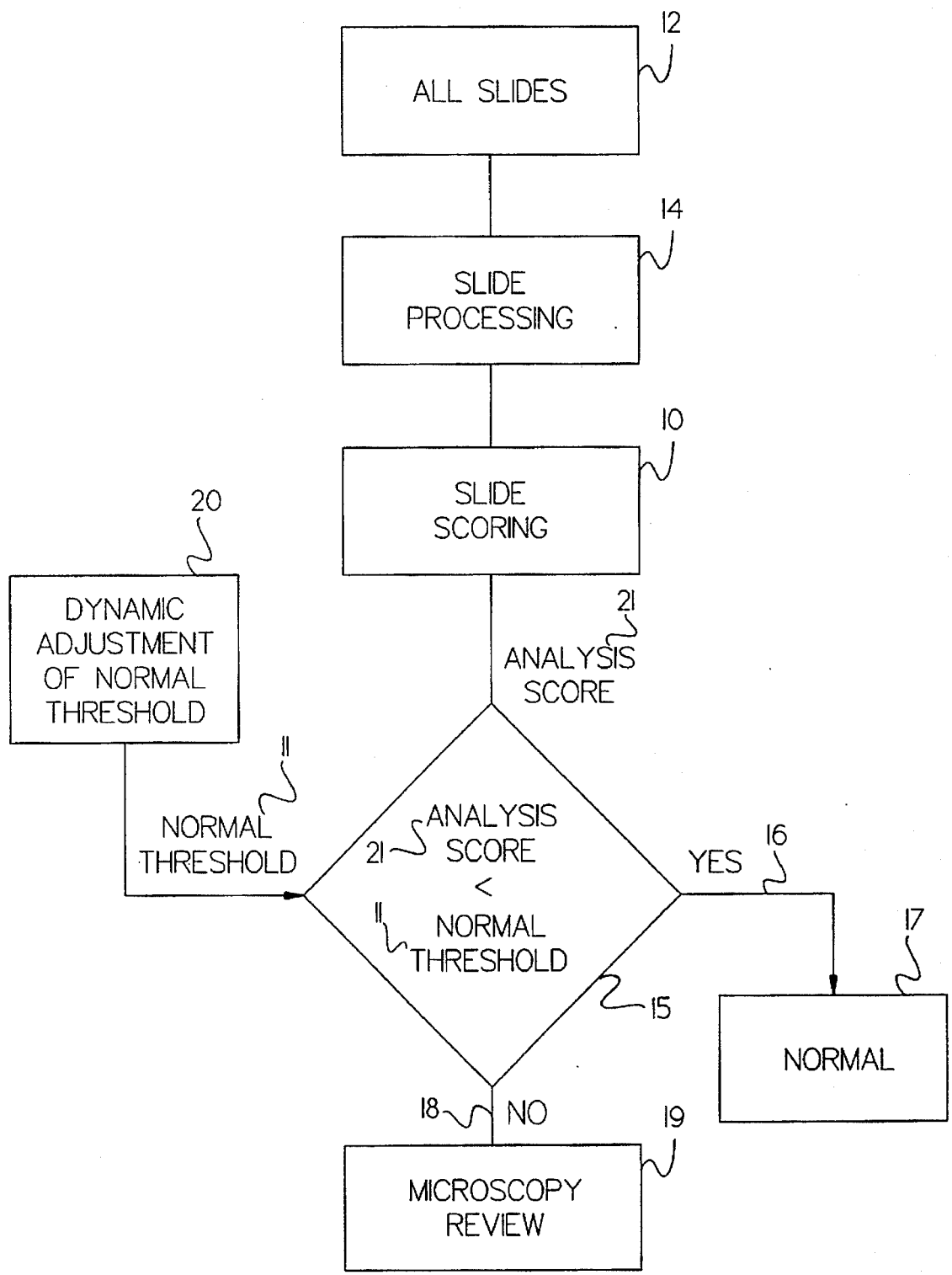
FIG. 1D shows a slide sorting schematic diagram of the invention.

Refer now to FIG. 1D which shows the slide scoring process of the invention. The invention provides a dynamic normalization method and apparatus for a biological specimen classifier such as the one shown in FIGS. 1A, 1B and 1C. Biological specimens 12 such as Pap smear slides are loaded into a slide processing stage 14. The slides are scored at step 10 and an analysis score 21 is generated. In one preferred embodiment of the invention, the analysis score 21 is generated by the method disclosed in a copending U.S. patent application entitled "Method for Identifying Normal Biomedical Specimens", filed Feb. 18, 1992 under application Ser. No. 07/838,064 incorporated herein by reference. The analysis score 21 is then compared to a threshold in step 15 where the threshold value differentiates between normal and potentially abnormal slide analysis scores. The slides 12 having an analysis score 21 less than a normal threshold 11 are classified as normal slides 17 which can be reported as normal without further human review. The slides 12 having an analysis score 21 greater than or equal to the normal threshold 11 are the potentially abnormal slides. The potentially abnormal slides require an independent microscopy review by a human in step 19. The decision logic may be expressed in pseudo code as follows:

---
IF analysis score < normal threshold THEN normal
ELSE microscopy review
---

The analysis score 21 is sensitive to the variations in patient populations and slide preparation methods. Normal slides with darker cell staining are more likely to have higher anomaly scores.

The dynamic normalization step 20 automatically adjusts the analysis score 21 threshold based on the specimen population. The threshold adjustment is designed to compensate for slide variations. The adjustment is also designed to yield stable operating characteristics in specificity and sensitivity. Those skilled in the art will recognize that the analysis score may be an anomaly score, quality control score, or screener score.

Figure 2:
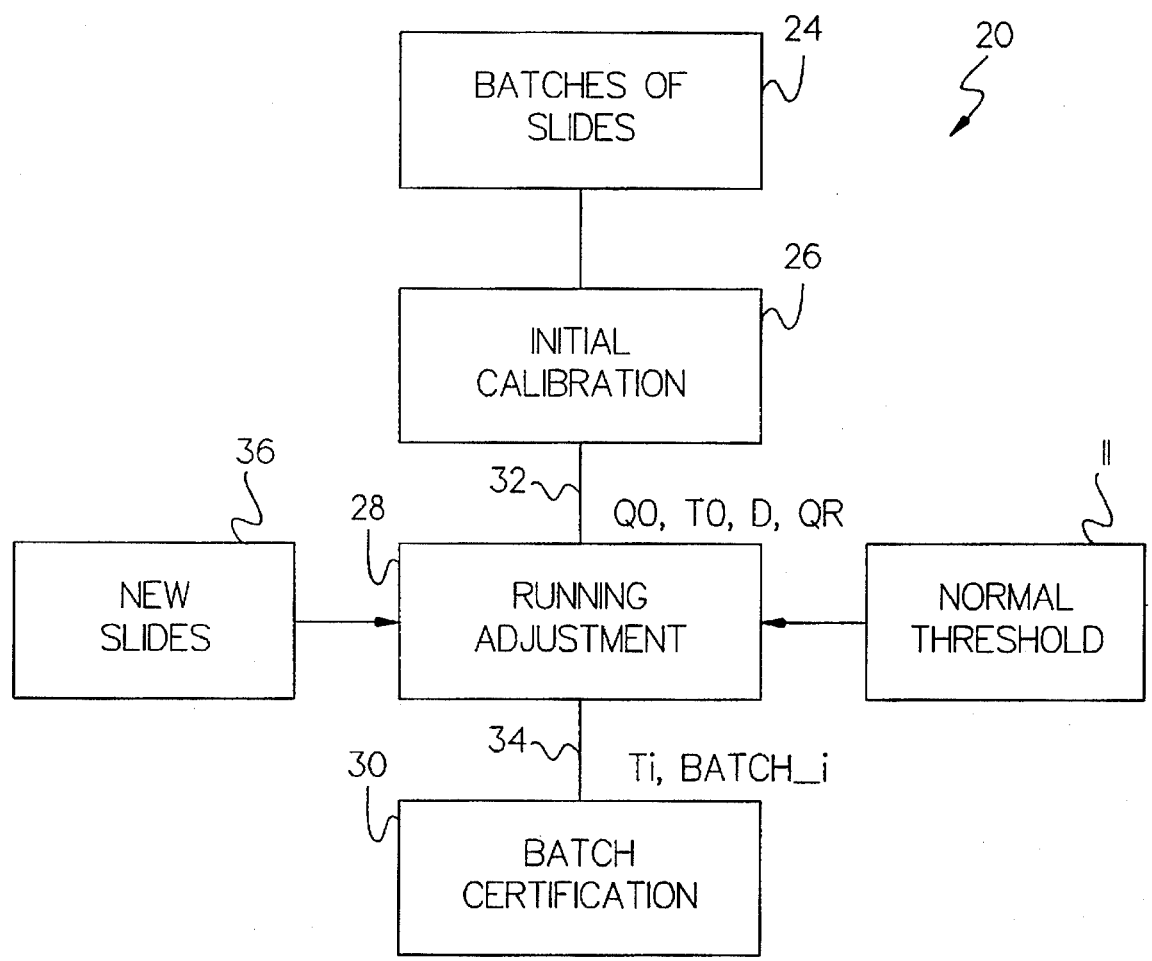
FIG. 2 shows processing stages for the dynamic calibration strategy.

Refer now to FIG. 2 which shows the dynamic adjustment of the normal threshold step 20 in more detail. The dynamic normalization step 20 achieves a consistent slide classification performance, as described by specificity vs. sensitivity, over a wide range of variations in labs, staining batches, and slide populations. The dynamic normalization step 20 comprises three stages of processing including an initial calibration stage 26, a running adjustment stage 28, and a batch certification stage 30.

The initial calibration stage 26 is designed to normalize the inter-tab variations. The running adjustment stage 28 is designed to normalize the intra-lab batch variations, and the batch certification stage 30 is designed to assure the integrity of the dynamic normalization process 20.

The initial calibration process 26 is conducted during system installation. The process may be repeated after major system upgrades or repairs. In addition, the apparatus of the invention is able to automatically detect significant changes in operating conditions through the batch certification stage and request the initiation of the calibration process. The steps comprising the initial calibration process for an 81% sort application are listed below:

(a) Select 300 normal and 200 abnormal slides from the archives of the lab. All slides should be representative to lab slide population and less than one year old.

(b) Process the slides to generate analysis scores. The scores of the successfully analyzed slides are gathered and sorted in descending order.

Figure 4A:
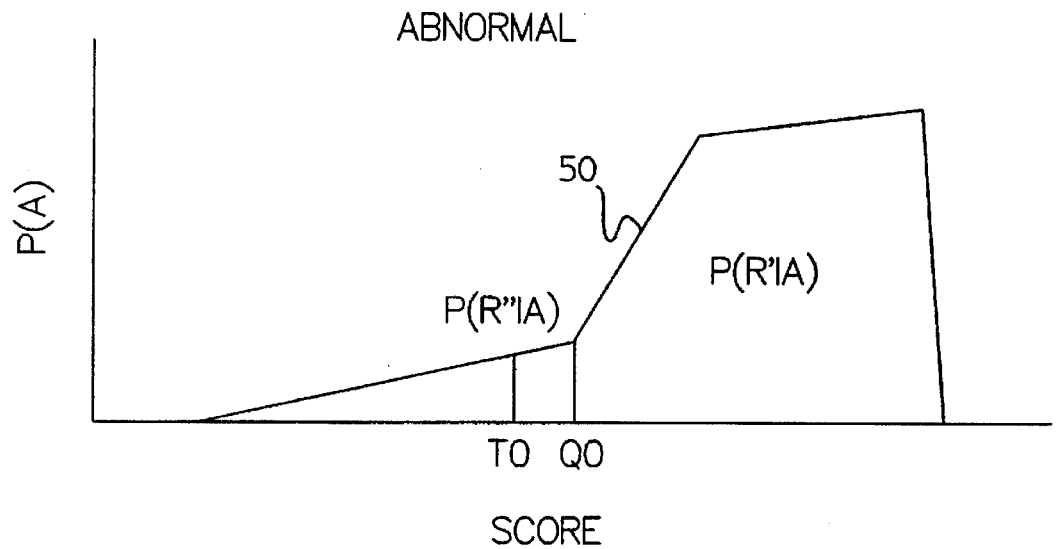
FIGS. 4A and 4B show Graphical illustrations of different thresholds and probabilities, $Q_o$ and $P(R'|N)$ in hypothetical distributions for abnormal and normal cases respectively.
Figure 4B:
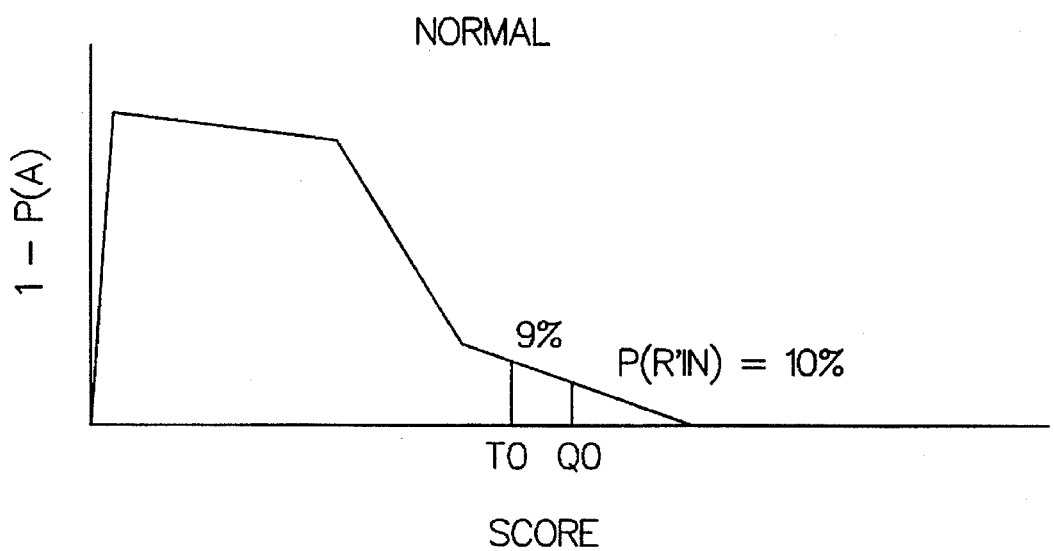

(c) The threshold value corresponding to the top 10% of the successfully processed normal slide population is defined as the initial qualification threshold $Q_0$. The expected percentage of normal slides rejected by $Q_0$, $P(R'|N)$, is equal to 0.1. FIG. 4A shows $Q_0$ and $P(R'|N)$ in hypothetical distributions.

(d) The percentage of abnormal slides called review, $P(R'|A)$, by $Q_0$ is determined.

(e) The threshold value corresponding to the top 19% of the successfully processed normal slide population is defined as the initial dynamic threshold $T_0$.

(f) The percentage of abnormal slides called review by $T_0$, $P(R''|A)$, is determined.

(g) Set the abnormal proportion $P(A)$ according to the slide population statistics of the lab of interest.

The default value is 1% for quality control applications.

(h) The dynamic threshold population ratio, D, is determined as:

$$D=(0.09(1-P(A))+P(A)(P(R''|A)-P(R'|A)))/((1-P(R'|N))(1-P(A))+P(A)(1-P(R'|A)))$$

(i) The expected qualification rejection proportion QR is determined as $$QR=P(R'|N)(1-P(A))+P(A)P(R'|A).$$

The outcomes of the calibration process are parameters: $Q_0$, $T_0$, D, and QR. These parameters will be used in the other stages of processing. Note that the number of calibration slides used in step (a) can be adjusted depending on the desired precision of the application. More slides will lead to greater precision in achieving the desired operating point. The training slides can be selected by different sampling methods such as random sample, stratified sample, etc.

Calibration slides are the slides which are successfully processed and slides having analysis score<Q. Calibration slides have stable characteristics and are used as the basis for a running adjustment.

Figure 3:
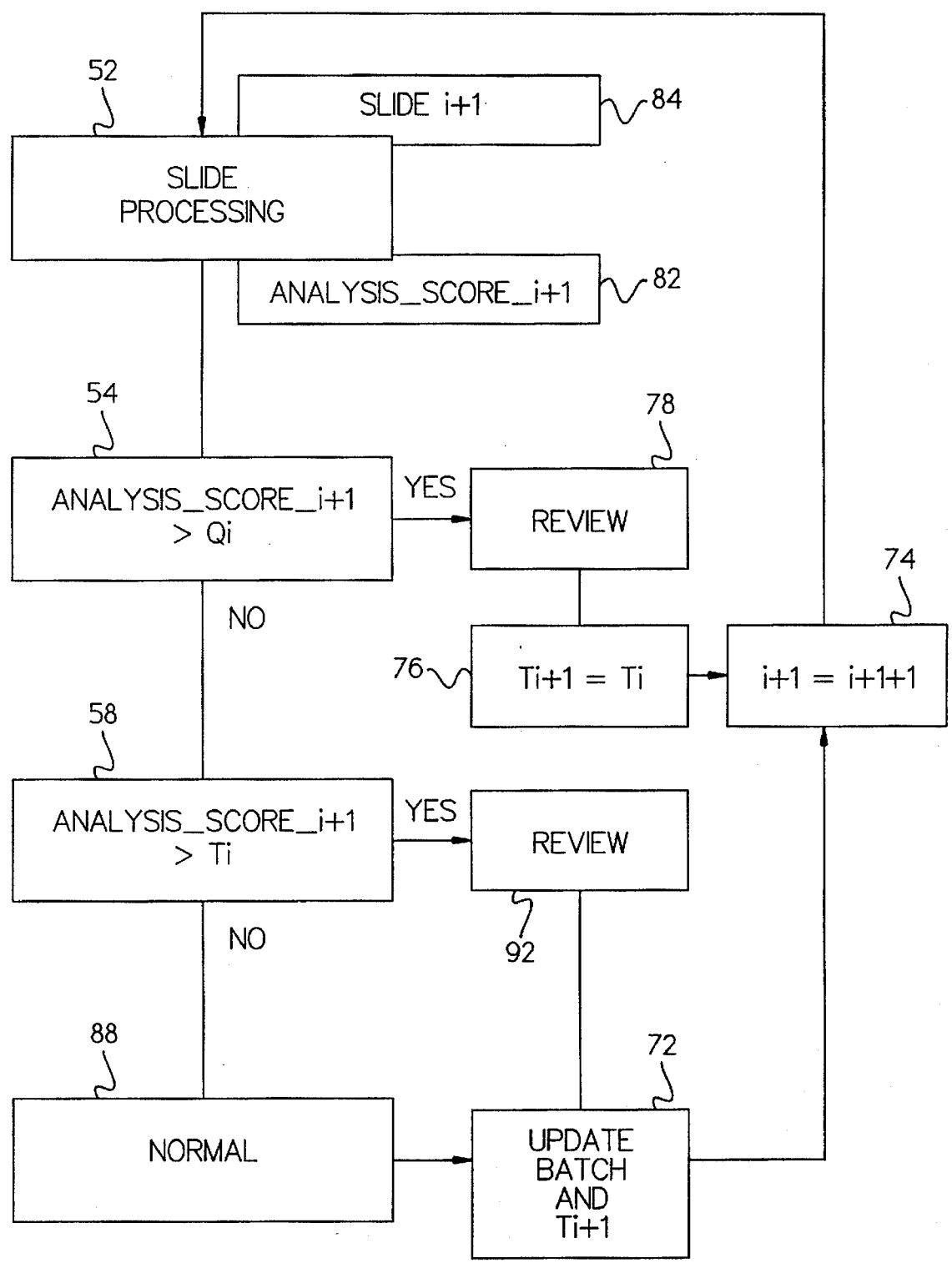
FIG. 3 shows a batch update process flow diagram.

Referring now to FIG. 3, FIG. 3 shows one example of a running adjustment method of the invention. In the running adjustment method of the invention a slide$_i$ is distinguished from slide$_{i+1}$ in that the slide$_{i+1}$ is the next slide to be examined in the running adjustment method. Slide$_{i+1}$ 84 is input to slide processing process step 52 and then analysis score$_{i+1}$ is output 82. If the analysis score$_{i+1}$ is greater than a threshold defined as $Q_i$, then the slide is sent for review in step 78. The review is a human review process where the slide is examined by a cytologist. If the analysis score$_{i+1}$ is less than or equal to $Q_i$, then the process advances to determine if the analysis score is greater than the threshold $T_i$. If it is, the slide is sent for human review in step 92. If the analysis score$_{i+1}$ is less than or equal to $T_i$ then the slide$_{i+1}$ is determined to be normal in step 88 and no review is necessary. If in step 54 the analysis score$_{i+1}$ is greater than $Q_i$ and the slide goes for review in step 78, the threshold $T_{i+1}$ is set equal to the old threshold $T_i$ in step 76. The process then increments to look at the next slide$_{i+1+1}$. If in step 58, the analysis score$_{i+1}$ is greater than $T_i$ the slide is sent for human review in step 92. In this case, the batch is updated and then T is updated for $T_{i+1}$. After the slide is determined to be normal in step 88, the batch is also updated and a new T is determined for $T_{i+1}$. In either one of these two cases, the process flows to step 74 where the next slide is loaded slide$_{i+1}$=slide$_{i+1+1}$. The process then flows back to step 52 to process the next slide. The process of the invention avoids updating the batch if the analysis score of the slide$_{i+1}$ is greater than $Q_i$. Otherwise the batch is updated.

Figure 5:
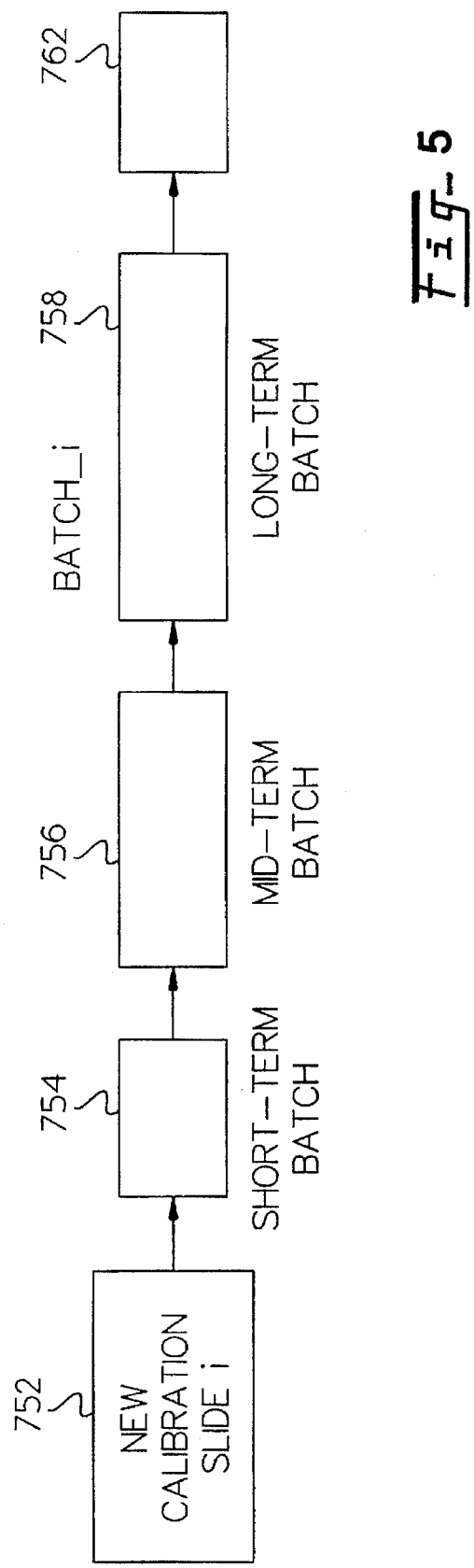
FIG. 5 shows a block diagram of one example of the batch processing method of the invention.

Refer now to FIG. 5 which shows a block diagram of one example of the batch processing method of the invention. In one aspect of the invention three running batches are defined including a short-term batch 754, a mid-term batch 756, and a long-term batch 758. The batches comprise calibration slides. In a preferred embodiment of invention, the short term batch consists of up to 300 calibration slides most recently processed. The mid-term batch consists of up to 600 calibration slides processed prior to the processing of the short-term slides. The long-term batch includes up to 1,200 calibration slides processed prior to the processing of the mid-term slides. A calibration slide is a slide which is determined to be satisfactory and suitable for analysis by the slide processing system. Its internal score is less than Q. In the state right after the initial calibration, only the short-term batch will be partially filled and there will be no slides in the other two batches. In the steady state of the processing, all batches should be filled. Note that the size of each batch can be adjusted based on the desired system sensitivity to the variations. The smaller the batch size, the more sensitivity of the system to small fluctuations in slide conditions. In addition, the number of different running batches can also be adjusted. It can be as simple as one fixed size batch or continuous batches of all slides processed by the system since the initial calibration. Moreover, the batch may not be a running one. It could be a fixed size batch given a starting point and an end point. In this case, the adjustment cannot be done until the completion of the slides in the whole batch.

The batches are updated dynamically for each slide. During slide processing, when a slide is qualified as a calibration slide the oldest slide in the long-term batch will be removed from the batch at 762 and the oldest slide in the mid-term batch will be moved to the long-term batch. Similarly, the oldest slide in the short-term batch will be moved to the mid-term batch. Finally, the newly processed calibration slide 752 will be included in the short-term batch. Note that a set of three running batches is associated with each processed slide i and the set may be different for different slides. The batch set for slide i is referred to batch_i. The update rules are similar for different alternations of the batches.

The batches are used to determine the dynamic threshold value Ti for each newly processed slide i+1. The dynamic threshold value is determined by ranking the analysis scores from slides in batch_i. In the ranking process, each slide from the short-term batch is given 4 counts, each slide from the mid-term batch, if exists, is given 2 counts, and each slide from the long-term batch, if exists, is given 1 count. The weighted raking approach gives highest weight for each slide in the short-term batch, and lowest weight for each slide in the long-term batch. Since there are more slides in the long-term batch than the short-term batch, the contributions from the three batches are equal. After the ranking process, the threshold corresponding to the top D proportion of the slides is used as the dynamic threshold value Ti. Note that the weight, for each batch is not limited to the described form and may be adjusted to achieve the desired system sensitivity to slide variations.

The classification logic for each successfully processed, and suitable for analysis, slide (slide i+1) comprises the following logical steps:

```
IF slide_score_i+1 > Qi
    THEN review and batch_i+1 = batch_i
ELSE IF slide_score_i+1 > Ti
    THEN review and update batch
        ELSE normal and update batch
``` where update batch is the process defined above which incorporates the current slide data into the calibration batch and updates T based on the strategy defined above.

To assure the integrity of the dynamic calibration strategy in dealing with the lab dynamics in slide preparations and patient populations, a batch certification process is implemented. The objective of this process is to constantly monitor the validity of the dynamic calibration process. To perform batch certification, the values of Qi, Ti, and Pi(Q) corresponding to each calibration slide i in the batches are recorded. Pi(Q) is the weighted probability of a slide rejected by the qualification thresholds Q's for super batch_i, where short-term is weighted by 4, mid-term by 2, and long-term by 1. Where super batch_i consists of all the calibration slides in batch_i as well as all successfully analyzed slides rejected by Q within the time period covered by batch_i. If Pi(Q)=QR then the calibration population matches the current slide population.

If the calibration population does not match the current slide population, an adjustment of the Q value may be required. The major cause of the difference is probably the percentage of normal slides called review, P(R'|N), which is preparation, sampling, and population dependent. The adjustment criteria and update rule for Q is

```
IF (Pi(Q) < 0.8QR or Pi(Q) > 1.2QR) THEN re-calibrate
ELSE IF (Pi(Q) < 0.95QR or Pi(Q) > 1.05QR)
    THEN Qi = adjust Q
    ELSE Qi = Qi-1
```

The adjust Q process generates a new Q following step 1(c) based on the super batch_i. After $Q_i$ is determined, an additional check is performed to validate this adjustment. If the adjustment suggests that the calibration population and the current population are significantly different, then a complete new calibration process is required. The checking rule is:

IF ($Q_i < 0.8 \ Q_0$ or $Q_i > 1.2 \ Q_0$) THEN re-calibrate
ELSE continue

In addition, the Ti generated above will also be checked to validate the new threshold. The checking rule is:

IF ($T_i < 0.8 \ T_0$ or $T_i > 1.2 \ T_0$) THEN re-calibrate
ELSE continue

Note that the certification limits can be adjusted based on the tolerable frequency of re-calibration and the desired operating point precision.

The invention may be applied to other than cytological specimens. The invention is equally applicable to all biological specimen examinations that are subject to variations from patient population, sampling, preparation, staining, and laboratory specific characteristics such as water, culture, and others. Examples of such biological specimen applications include urine sediment analysis specimens, histology examination specimens, and hematology examination specimens, and other similar biological specimens.

APPARATUS FOR IDENTIFICATION AND INTEGRATION OF MULTIPLE CELL PATTERNS, U.S. patent application Ser. No. 08/308,992

The slide classification method of the invention comprises an object classification step and a slide classification step. The object classification step processes a set of images from the slide. It detects and classifies the objects of interest. The object classification results are accumulated for the whole slide. The accumulated object classification results are then used by the slide classification step to derive an analysis score. The present invention integrates multiple classifiers at the object level to generate highly reliable object classification results. The object classification results are then used as the basis for slide classification. Given good object features, the slide classification can be implemented using the method disclosed in a copending application entitled "A Method and Apparatus for Robust Biological Specimen Classification", incorporated herein by reference.

Figure 6:
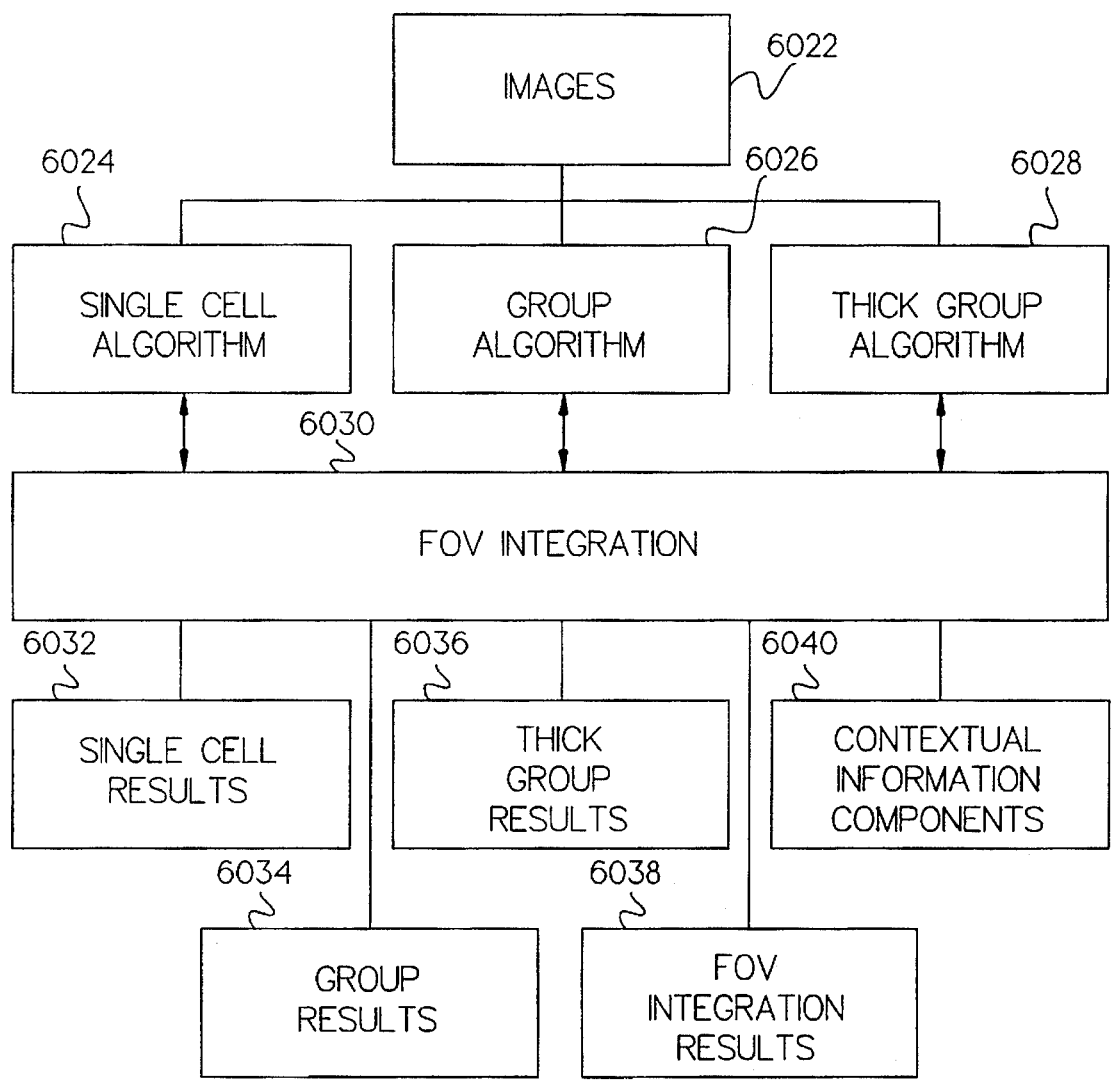
FIG. 6 shows the slide classification architecture.

Referring now to FIG. 6, the object classification stage includes four processing components: a single cell classifier 6024, a group classifier 6026, a thick group classifier 6028, and an FOV integrator 6030.

The single cell classifier 6024 detects and classifies a majority of free-lying and non nuclear overlapped cells in an image field of view (FOV). The potential pre-malignant or malignant cells are identified and assigned a confidence value for each detected object. The confidence value ranges from 0 to 1: "0" denotes objects which most likely are clearly normal cells and "1" denotes objects which are most likely true malignant cells. Objects having confidence values higher than an alarm threshold inn the range between 0 and 1 are called alarmed objects. Objects having confidence values lower than a normal threshold which is less than or equal to the alarm threshold are called negative objects.

Figure 7:
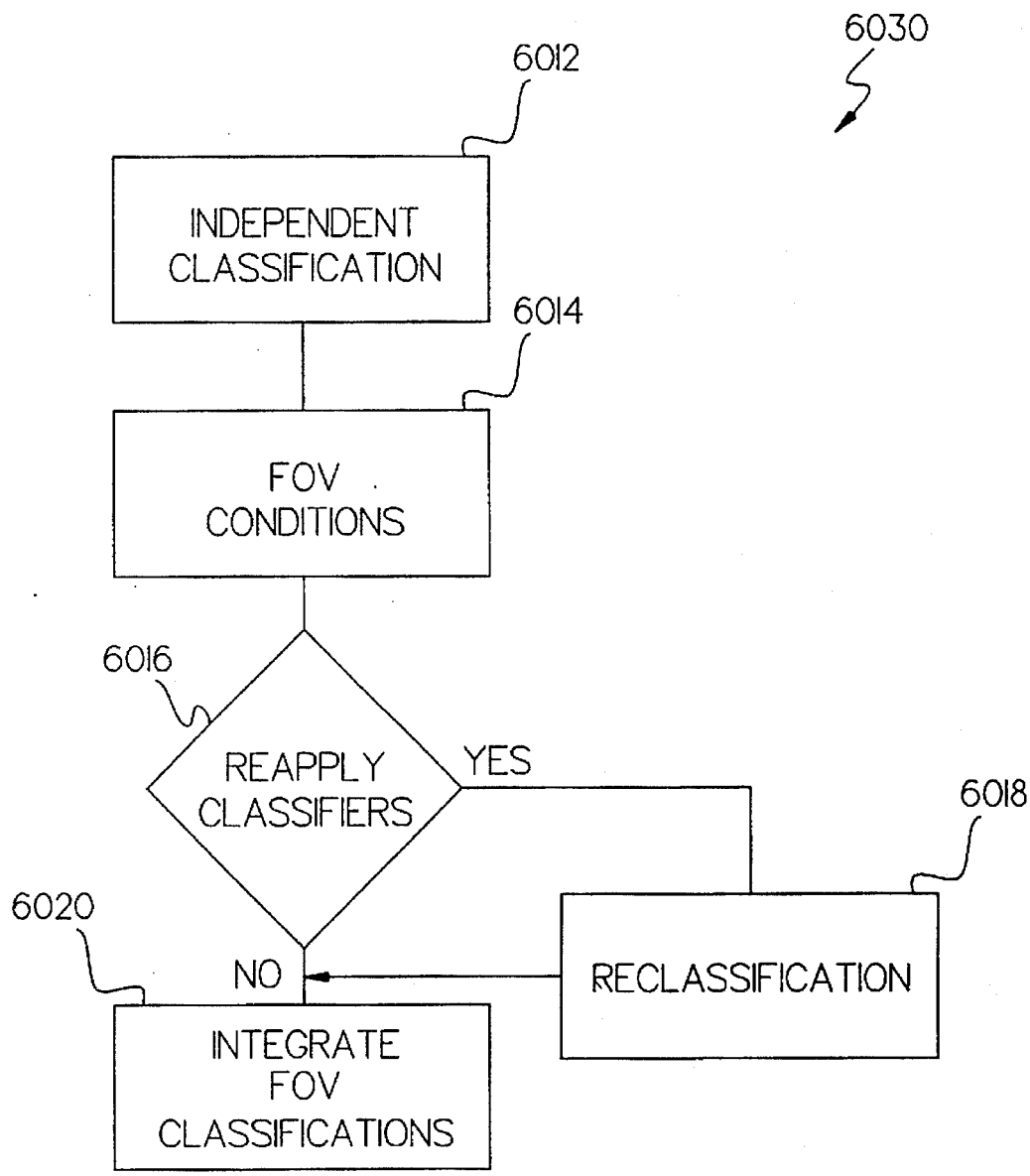
FIG. 7 shows a flow diagram for classification and integration.

Referring now to FIG. 7, a more detailed flow chart of an FOV integration method is shown. The FOV integrator 6030 is used to control and integrate the results of the three classifiers. The FOV integration includes four FOV integration steps:

independent application of the three classifiers to an image in step 6012;

determine the FOV conditions in step 6014;
re-apply object classifiers if needed in step 6018; and
integrate the FOV classification results in step 6020.

In the independent application of the three classifiers to an image in step 6012 three classifiers are applied to the same image independently.

The classification results of the three classifiers are used to determine the conditions of the FOV. The classifier results include the following:

(A) The outcomes of the single cell classifier 6032 are:
  (i) number of alarms; and
  (ii) number of negatives.

(B) The outcomes of the group classifier 6034 are:
  (i) number of detected groups;
  (ii) percent of abnormal groups among all detected groups in the FOV; and
  (iii) percent of normal groups among all detected groups in the FOV.

(C) The outcomes of the thick group classifier 6036 are:
  (i) number of detected thick groups; and
  (ii) percent of abnormal thick groups among all detected thick groups in the FOV.

The outcomes of the classifiers determine the FOV conditions. An FOV having co-existence of single cell alarm, group and thick group abnormals will most likely have true abnormal cells. In contrast, an FOV having zero single cell, group and thick group abnormal detections will most likely have no true abnormal cells. In both cases, the results from multiple classifiers are consistent and no classifier re-application is necessary.

On the other hand, there are cases where different classifiers yield inconsistent results. In these cases, the classifiers will be re-applied given the outcomes from the other classifiers as features to refine the original classification in an attempt to resolve the conflicts.

The conflict conditions between single cell and group classifiers that indicate re-classification of the single cell classifier are:

(a) single cell alarm>0 AND % group alarm=0 AND % group normal>0

(b) single cell alarm=0 AND single cell negative>0 AND % group alarm>0

The conflict conditions between single cell and thick group classifiers that indicate re-classification of the single cell classifier are:

(a') single cell alarm>0 AND % thick group alarm=0 AND # thick group>0

(b') single cell alarm=0 AND single cell negative>0 AND % thick group alarm>0

In cases (a) and (a') only the single cell alarms will be re-classified. For cases (b) and (b'), a set of objects having confidence values greater than a re-classification threshold, that is lower than the alarm threshold, will be re-classified. The decision rule is:

IF single cell object confidence value>re-classification threshold THEN re-classify ELSE no change The conflict conditions between group and single cell classifiers that indicate re-classification of the group classifier are:

(a) % group alarm>0 AND single cell alarm=0 AND single cell negative>0

(b) % group alarm=0 AND % group normal>0 AND single cell alarm>0

The conflict conditions between group and thick group classifiers that indicate re-classification of the group classifier are:

(a') % group alarm>0 AND % thick group alarm=0 AND # thick group>0

(b') % group alarm=0 AND % group normal>0 AND % thick group alarm>0

In cases (a) and (a') only the group alarms will be re-classified. For cases (b) and (b'), all segmented groups in the FOV will be re-classified.

The conflict conditions between thick group and single cell classifiers that indicate re-classification of the thick group classifier are:

(a) % thick group alarm>0 AND single cell alarm=0 AND single cell negative>0

(b) % thick group alarm=0 AND # thick group>0 AND single cell alarm>0

The conflict conditions between thick group and group classifiers warrant the re-classification of the thick group classifier are:

(a') % thick group alarm>0 AND % group alarm=0 AND % group normal>0

(b') % thick group alarm=0 AND # thick group>0 AND % group alarm>0

In cases (a) and (a') only the thick group alarms will be re-classified. For cases (b) and (b'), all segmented thick groups in the FOV will be re-classified.

To show the completeness of the logic, the relationships between single cell and group classifiers and their implications are listed in the following table:

|  | % group alarm > 0 | % group normal > 0 | # group = 0 |
| --- | --- | --- | --- |
| single cell alarm > 0 | in concert, no action | in conflict, re-classify | no action |
| single cell negative > 0 | in conflict, re-classify | in concert, no action | no action |
| # single cell object = 0 | no action | no action | no action |

The re-apply object classifiers if needed step 6018 reclassifies each slide based on classification goals. Since there are three classifiers and the conflict resolution process is order dependent, the order is pre-determined based on the slide classification goals. If the goal is the classification of abnormal vs. normal conditions, then the single cell classifier provides the primary classification feature. In this case, the conflict resolution sequence is:

(i) adjust thick group classifier conditioned on single cell classifier results;

(ii) adjust group classifier conditioned on the adjusted thick group classifier results; and (iii) adjust single cell classifier conditioned on the adjusted group classifier results.

If the goal is the classification of endocervical cell conditions, then the group classifier provides primary classification feature. In this case, the conflict resolution sequence is:

(i) adjust thick group classifier conditioned on group classifier;

(ii) adjust single cell classifier conditioned on the adjusted thick group classifier; and (iii) adjust group classifier conditioned on the adjusted single cell classifier.

The object re-classification classifiers use both original object features and object classification outcomes from the conflicting classifiers as features for classification. In a preferred embodiment of the invention, the classifiers were constructed through a training process as described in "A Processing Strategy for Automated Papanicolaou Smear Screening" by Lee et al. in the Analytical and Quantitative Cytology and Histology, Vol. 14 No. 5, pp. 415–425, October 1992. The Classification And Regression Trees (CART) (see "Classification And Regression Trees", by Breiman et al., Belmont, Calif., Wadsworth, 1984) is used as the basis for the classifiers.

The integrate the FOV classification results step 6020 integrates individual results into FOV integration results 6038.

After the object re-classification, the final object classification results are saved and accumulated to be used for slide classification. In addition, the FOV results of multiple classifiers are correlated and accumulated to improve the slide classification results. The FOV correlation features include:

f(GRP alarm¦SC alarm): the co-occurrence frequency of a single cell alarm having at least a group alarm in the same FOV;

f(TGRP alarm¦SC alarm): the concurrence frequency of a single cell alarm having at least a thick group alarm in the same FOV;

f(GRP alarm, TGRP alarm¦SC alarm): the co-occurrence frequency of a single cell alarm having at least a group alarm and at least a thick group alarm in the same FOV;

f(GRP normal¦SC alarm): the co-occurrence frequency of a single cell alarm having no group alarm yet having at least one group normal object in the same FOV;

f(TGRP normal¦SC alarm): the co-occurrence frequency of a single cell alarm having no group alarm yet having at least one thick group normal object in the same FOV;

f(GRP normal, TGRP normal¦SC alarm): the co-occurrence frequency of a single cell alarm having no group or thick group alarms and yet having at least a group and a thick group normal object in the same FOV;

f(SC alarm¦GRP alarm): the co-occurrence frequency of a group alarm having at least a single cell alarm in the same FOV;

f(TGRP alarm¦GRP alarm): the co-occurrence frequency of a group alarm having at least a thick group alarm in the same FOV;

f(SC alarm, TGRP alarm¦GRP alarm): the co-occurrence frequency of a group alarm having at least a single cell alarm and at least a thick group alarm in the same FOV;

f(SC normal¦GRP alarm): the co-occurrence frequency of a group alarm having no single cell alarm yet having at least one single cell normal object in the same FOV;

f(TGRP normal¦GRP alarm): the co-occurrence frequency of a group alarm having no thick group alarm yet having at least one thick group normal object in the same FOV;

f(SC normal, TGRP normal¦GRP alarm): the co-occurrence frequency of a group alarm having no single cell or thick group alarms and yet having at least a single cell and a thick group normal object in the same FOV;

f(SC alarm¦TGRP alarm): the co-occurrence frequency of a thick group alarm having at least a single cell alarm in the same FOV;

f(GRP alarm¦TGRP alarm): the co-occurrence frequency of a thick group alarm having at least a group alarm in the same FOV;

f(SC alarm, GRP alarm¦TGRP alarm): the co-occurrence frequency of a thick group alarm having at least a single cell alarm and at least a group alarm inn the same FOV;

f(SC normal,TGRP alarm): the co-occurrence frequency of a thick group alarm having no single cell alarm yet having at least one single cell normal object in the same FOV;

f(GRP normal,TGRP alarm): the co-occurrence frequency of a thick group alarm having no group alarm yet having at least one group normal object in the same FOV; and f(SC normal, GRP normal,TGRP alarm): the co-occurrence frequency of a thick group alarm having no single cell or group alarms and yet having at least a single cell and a group normal object in the same FOV.

The above FOV correlation features are accumulated over the FOVs from a slide. The accumulated results for the whole slide are then used as features to contribute in the slide classification stage.

The final outcomes of all classifiers 6032, 6034, and 6036 are accumulated for slide classification. FOV integration results 6038 are also accumulated. In addition, the difference between the preliminary outcomes and the final outcomes of each object classifier are recorded for each FOV. The difference represents the contribution of the contextual information to the classification results 6040. The difference information is accumulated over the whole slide. This information is used for slide classification.

The accumulated FOV features including the final object classification results, FOV integration features, and contextual information are used to perform slide classification. The slide classifier can again be constructed through a training process as described in "A Processing Strategy for Automated Papanicolaou Smear Screening" by Lee et al. in the Analytical and Quantitative Cytology and Histology, Vol. 14 No. 5, pp. 415–425, October 1992. The Classification And Regression Trees (CART) (see "Classification And Regression Trees", by Breiman et al , Belmont Calif., Wadsworth, 1984) can be used as the basis for the classifiers. The output of the slide classifier is the analysis score.

Refer again to FIG. 8 which shows FOV integration of the method of the invention. In a preferred embodiment of the implementation, the single cells are identified by the method disclosed in a pending U.S. patent application entitled "Method for Identifying Objects Using Data Processing Techniques," Ser. No. 07/838,395 described hereinbelow. The object classification and confidence value is assigned based, on the method disclosed in a pending U.S. patent application entitled "Method for Identifying Normal Biological Specimens," Ser. No. 07,838,064 described hereinbelow. In a conventionally prepared Papanicolaou smear, the number of detected single cells in a high resolution FOV (20× objective lens) varies significantly. The range may be from 1 to 200.

The group classifier 6026 detects and classifies groups of cells formed in sheet or syncytium arrangements. See, for example, Patten Jr., Stanley F., *Diagnostic Cytology of the Uterine Cervix*, Basel, Switzerland, Publisher: S. Karger, 1969 2nd Edition 1978, third volume in *Monographs in Clinical Cytology* edited by G. L. Weid. A sheet of cells is a grouping in which the component cells are regularly arranged in relation to one another and possess distinct cell boundaries. A syncytium is a group of cells which are irregularly arranged with respect to one another and have indistinct cell boundaries. The detected cell groups are classified as polymorphonuclear leukocytes, squamous cell groups, endocervical and metaplastic cell groups, or abnormal cell groups. As disease progresses, pre-malignant or malignant cells begin to form as groups of cells. The cells have rather irregular formations and often have a great deal of variation in size and shape between cells according to the severity of the disease. Polymorphonuclear leukocytes are white blood cells often associated with benign inflammatory conditions. Squamous cell groups are a group of benign squamous cells with rather uniform cell formations. Endocervical and metaplastic cell groups are cells sampled from the transformation zone of the cervical canal. The normal cell groups have a much more uniform structure and fewer cell to cell variations compared to abnormal ones. Cells from normal cell groups can be mistaken for pre-malignant or malignant cells when examined an individual, cell at a time without contextual information. However, when contextual information is included in the evaluation, diagnosis accuracy can be significantly improved.

The thick group classifier 6028 detects and classifies thick groups of cells formed as three-dimensional clusters of cells. A cell cluster is a more or less three-dimensional grouping of cells with altered polarity and usually poorly-defined cell boundaries. The detected thick groups are classified as normal cell clusters, endometrial cell clusters, or abnormal cell clusters. Cervical cancer of glandular origin such as adenocarcinoma tends to form as three dimensional clusters of cells.

Note that the same strategy can be applied to object processing with more than the above three classifiers.

Now referring jointly to FIGS. 6 and 7 which show the processing components and data flow diagrams for the object classification stage. The separate classifiers 6024, 6026, 6028 independently detect and classify the types of objects in step 6012, allowing information to be extracted from almost the entire field of view. The information from the different conditions present in the field of view is combined in step 6014. In step 6016, the combined information from the independent classifications is used to determine whether or not the classifiers should be reapplied for the field of view. If the classifiers are consistent, then the process proceeds to step 6020 where the field of view classifications are integrated. Otherwise, the classifiers are reapplied in step 6018, and then integrated in step 6020.

METHOD FOR IDENTIFYING OBJECTS USING DATA PROCESSING TECHNIQUES, U.S. patent application Ser. No. 07/838,395

As mentioned above the present invention comprises a method for use with image analysis systems for identifying objects of interest within the field of view of a microscope of the image analysis system. The method of the subject invention is particularly suited for use with image analysis systems constructed for analysis of cytological specimens and, more particularly, for analysis of the characteristics of the cells of the specimen.

Figure 8:
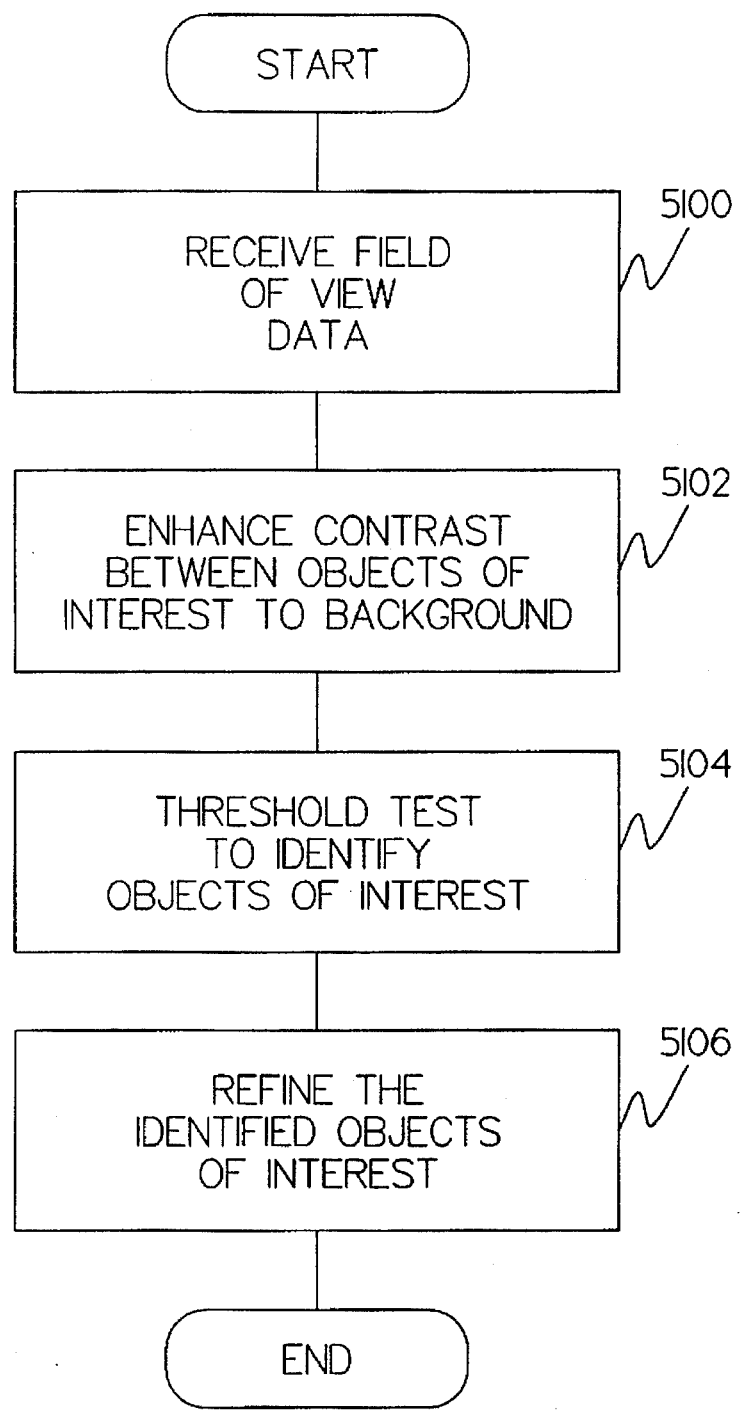
FIG. 8 is a method flow diagram illustrating generally the steps of a method employed by the subject invention for identifying objects of interest.

One method for identifying objects of interest within the field of view of a microscope is illustrated generally in FIG. 8. Therein, the first step is to receive the field of view data for analysis, step 5100. The field of view data is data from the microscope of the image analysis system that represents the image of a field of view of the microscope. In one embodiment of the invention, the microscope imaging apparatus may provide as many as 15,000 fields of view for one specimen. However, it will be apparent to those skilled in the art that many fields of view will have no objects of interest. Accordingly, the data received in step 5100 is assumed to have been prescanned, or otherwise preselected, as field of view data that includes objects of interest.

The field of view data is typically an array of data words wherein each data word represents a pixel (picture element) of the camera of the image analysis system. In the embodiment of the invention, the field of view data is grayscale field of view data, i.e., each data word is a multiple bit binary data word wherein the value of the data word is indicative of the transmissivity of the portion of the specimen associated with the pixel represented by the data word. However, portions of the present invention are equally applicable to binary field of view data, i.e., data wherein each data word indicates either the presence or absence of an object in the portion of the specimen associated with the pixel represented by the data word.

Figure 9A:
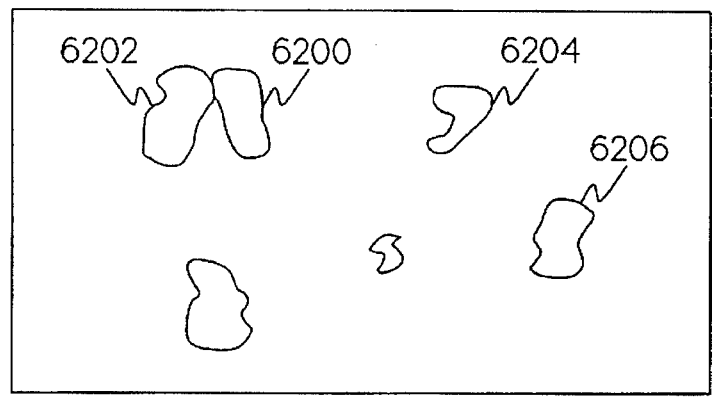
FIGS. 9A, 9B, and 9C are diagrams illustrating objects of a specimen on a slide.
Figure 9B:
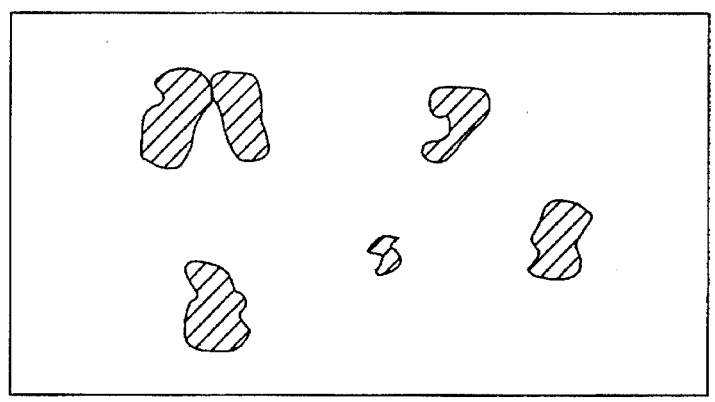
Figure 9C:
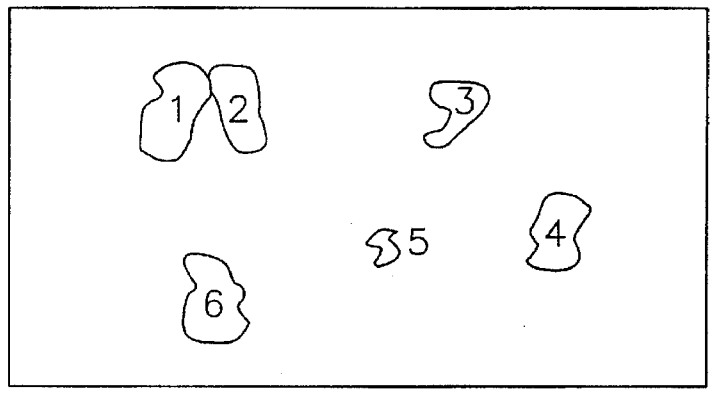

The field of view data, representing an image of the field of view of the microscope imaging apparatus, is processed individually to identify objects of interest within the field of view. The result of the method for identifying objects of interest, i.e., cells in the case of a cervical Pap smear, is a mask that identifies the size, shape, and location within the field of view of the object of interest and a mask that provides a unique identification value to each object in the image. With reference to FIG. 9A, a field of view of a microscope is illustrated including several objects of interest labeled 6200, 6202, 6204, and 6206. FIG. 9B illustrates the mask that will be developed for identifying the size, shape, and location of the objects of interest illustrated in FIG. 9A. FIG. 9C illustrates the mask that will be generated to provide the identification value to the objects of interest illustrated in FIG. 9A. It will be appreciated by those skilled in the art that when used for cervical Pap smear analysis, in addition to other cell analysis, the method for identifying objects will provide the mask illustrated in FIGS. 9B and 9C for both the nucleus and cytoplasm of each cell contained within the field of view of the microscope. Further, it will be apparent to those skilled in the art that the illustration provided in FIGS. 9B and 9C are representations of data generated in accordance with the method for identifying objects, and are not necessarily provided as the output of the method. The representations are provided here only to help in the description of the invention.

To identify the objects of interest and provide the mask illustrated in FIGS. 9B and 9C, the method first enhances the contrast between the objects of interest and the background, step 5102. This enhancement is provided to increase the differential between data representing the edge of an object and data representing the background. Thereafter, each object in the field of view is subjected to a threshold test to determine whether the brightness of the object lies within a predetermined range of brightness expected for objects of interest. Since the field of view may contain artifacts in addition to objects of interest, it is desirable to not only identify the size, shape, and location of the objects of interest, but to also eliminate from further analysis any artifacts, e.g., hair, dirt, dust, etc., that may inadvertently appear in the field of view. To this end, a range of predetermined values are provided for several characteristics of the objects of interest wherein the objects of interest are expected to lie within the range of values provided. The characteristics that are examined are brightness, size, and shape. It will be apparent, however, to those skilled in the art, that if the method is applied to other types of image analysis systems, other characteristics may be selected to identify various other objects of interest.

After performing the threshold test of step 5104, the objects of interest have been identified, The next step, therefore, is to refine the image of the objects of interest and to produce the mask illustrated in FIGS. 9B and 9C, step 5106.

Figure 10:
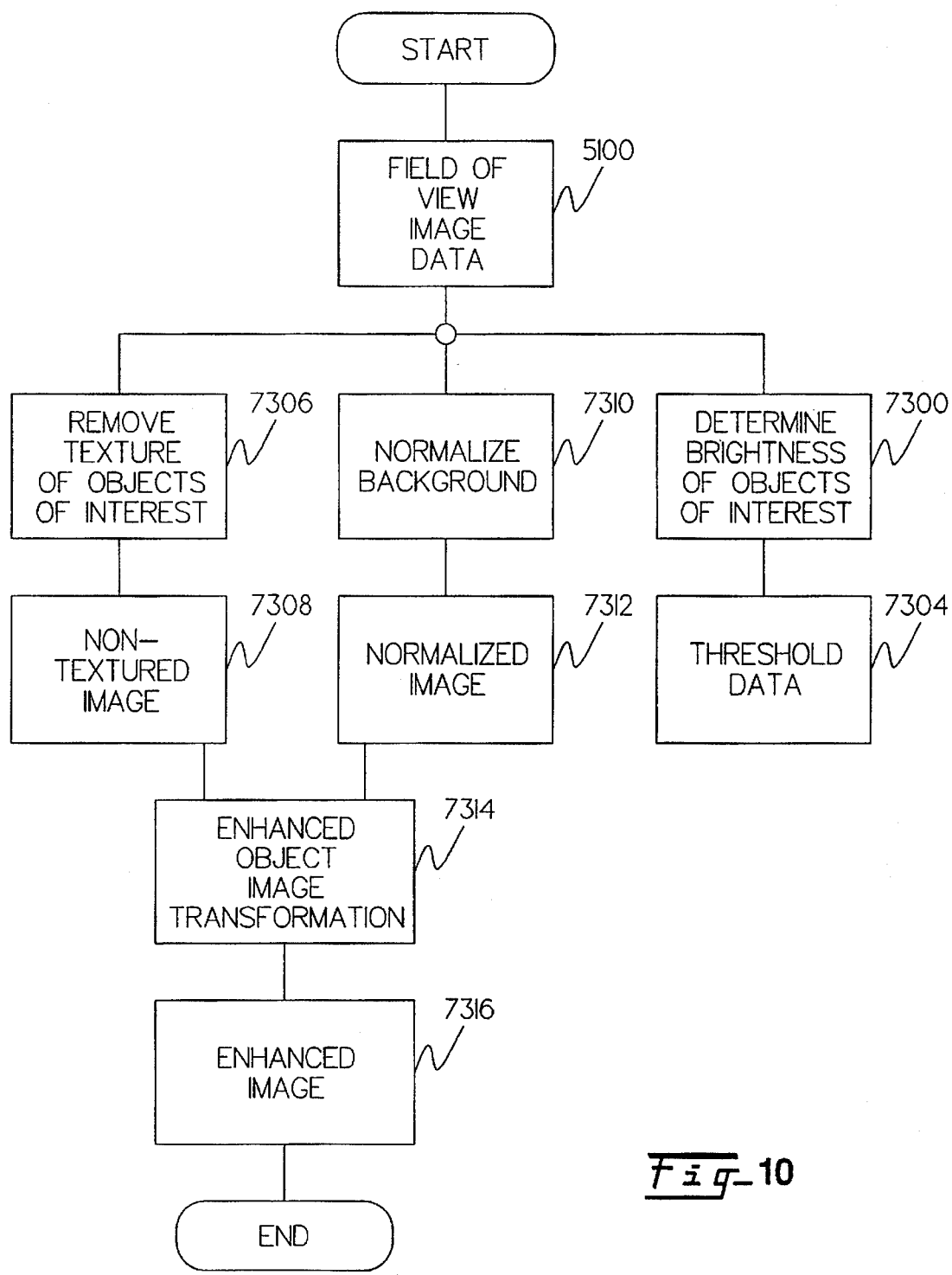
FIG. 10 is a method flow diagram illustrating substeps for executing step 5102 of FIG. 9.

A more detailed decision flow diagram illustrating the method for preforming the contrast enhancement of step 5102 is provided in FIG. 10. The first step in enhancing the image is to determine selected parameters of the field of view data. In the embodiment of the invention illustrated in FIG. 10, the selected parameters are the brightness of the nucleus, cytoplasm, and background, step 7300. Those skilled in the art will appreciate that the image analysis system may, for various reasons, have variations in brightness from field of view to field of view. The most obvious contributor to brightness variation being the brightness in the illumination system, or light provided to the slide, prior to taking the field of view image data. However, other factors can contribute to variation in brightness from one field of view to the next. Accordingly, the determination of step 7300 is made to effectively scale the brightness of the subject field of view.

Figure 11:
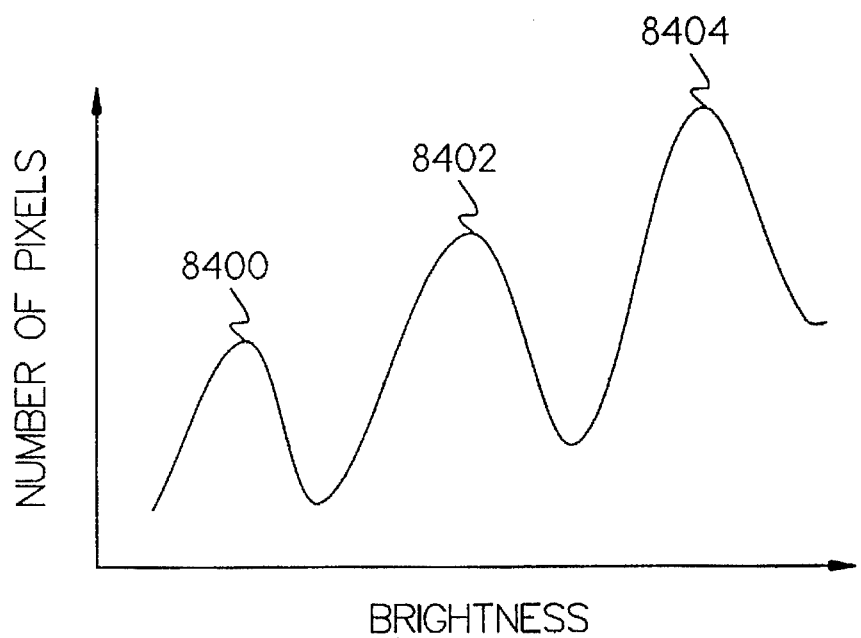
FIG. 11 is a graph illustrating an ideal distribution of pixel brightness for a slide used in combination with the subject invention.

The brightness determination of step 7300 may be performed by sing a histogram function to determine how many pixels within the grayscale field of view have a certain brightness. The results of the histogram may be graphed as illustrated in FIG. 11. Ideally, the result of the histogram will be a curve having three peaks, wherein the brightest peak 8404 is indicative of the number of pixels presenting the background of the field of view. The medium brightness peak 8402 is indicative of the number of pixels representing the cytoplasm of the cell of interest, and the darkest peak 8400 represents the number of pixels representing the nucleus of the cell.

Figure 12:
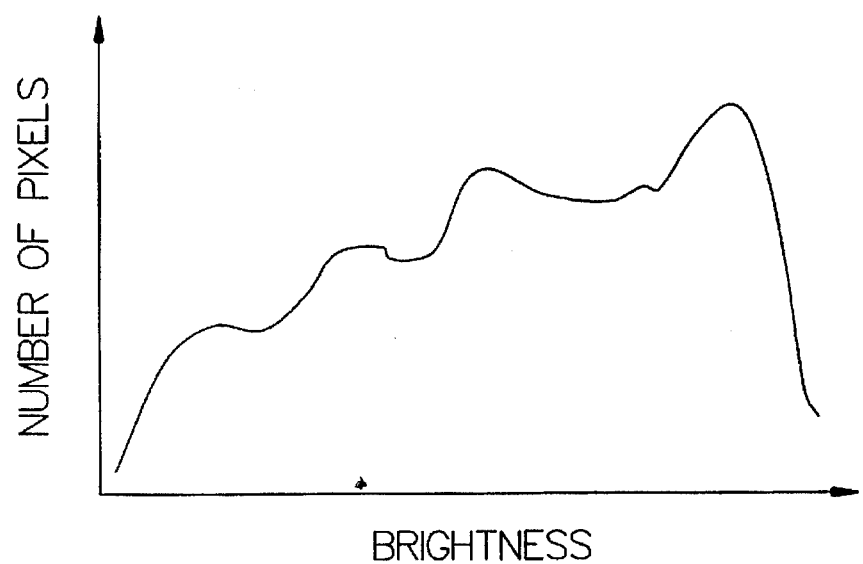
FIG. 12 is a graph of a distorted histogram wherein the peaks are virtually indistinguishable from the valleys and wherein the brightness at which a peak occurs is indeterminate.

However, since the method for identifying objects is intended for use without any special preparation of the specimen, cells may be provided in overlapping fashion or in clumps. These cells will tend to distort the results of the histogram, thereby deviating the histogram from the ideal illustrated in FIG. 11. Such a distorted histogram is illustrated in FIG. 12 wherein the peaks are virtually indistinguishable from the valleys and wherein the brightness at which the perk occurs is indeterminate. To reduce the impact of overlapping cells on the parameter determination of step 7300, morphological functions such as repeated dilation and erosion may be performed to remove overlapped objects from the field of view. The morphological functions of dilation and erosion are well known to those skilled in the art and need not be discussed in detail here.

Figure 13:
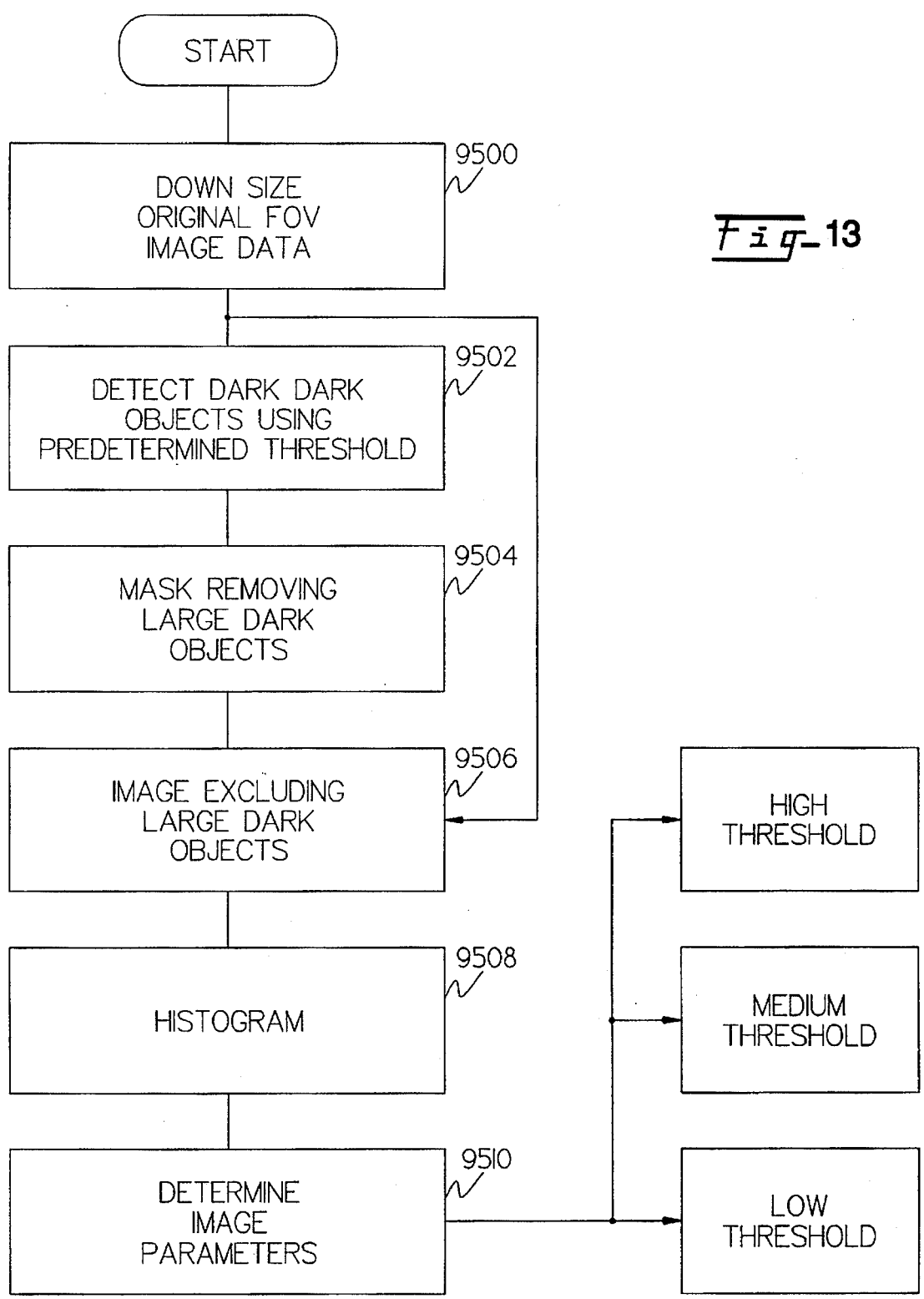
FIG. 13 is a method flow diagram illustrating steps used to determine the brightness distribution of pixels for a particular field of view.

Referring to FIG. 13, a method is provided for determining the brightness of objects of interest and providing the threshold data of steps 7300 and 7304. Therein, the original image is first downsized, step 9500. Downsizing of the original image is performed to save time in the parameter estimation stage. It is noted that detail of the size and shape of the original field of view image are not necessary for accurate determination of the threshold data. Downsizing may readily be performed by methods known in the art.

After downsizing of the original image, dark objects are detected using a predetermined threshold. This is performed by eliminating all field of view image data that is not equal to or above the predetermined threshold, step 9502. Thereafter, the large objects are removed from the image generated in step 9502. Removal of the large objects can be obtained using an opening residue operation. As is known in the art, an opening residue is simply a morphological opening to produce an opened image followed by a difference operation to combine the opened image with the original image. Thereafter, the downsized image is combined with the image created in step 9504 to exclude the large dark objects detected by the image of step 9504 from the downsized image of step 9500, step 9506.

As discussed above by reference to FIGS. 11 and 12, overlapped and closely packed cells will distort any distinction between the brightness of the nucleus, the cytoplasm, and the background of the field of view, thereby making the parameter determination extremely difficult, if not impossible. Steps 9502 and 9504 are therefore intended to remove large dark objects from the image data used for parameter determination, thereby isolating representative objects of interest. Those skilled in the art will appreciate that overlapping cells will be dark and distinguished from the dark nucleus by their size. Accordingly, steps 9502 and 9504 are intended to remove objects having a darkness similar to that expected for the nucleus and having a size much greater than that expected for the nucleus. It will be apparent to those skilled in the art that in other applications other criteria could be selected to remove objects that distort the parameters and to isolate objects representative of the parameters being measured.

After the large dark objects are removed from the downsized image, step 9506, a histogram is performed, step 9508, and the image brightness parameters determined, step 9510. In one embodiment of the invention, used to identify cells in a cervical Pap smear, the results of the image determination, step 9510, is a high threshold representing background, a medium threshold representing cytoplasm, and a low threshold representing the nucleus, as also illustrated in FIG. 11.

The results of the parameter determination of step 7300 is threshold data providing data indicative of the expected threshold of the nucleus, cytoplasm, and background of a particular field of view of a particular specimen, step 7304. Those skilled in the art will appreciate that the threshold data must be determined uniquely for each field of view since the variations in the image analysis system discussed above will cause the parameters to change from field of view to field of view. Further, although the parameters of the embodiment, discussed herein are brightness one the objects of interest, other parameters could be selected and determined in various other applications.

As mentioned above, the results of the method is to create a mask that identifies the size, shape, and location of the objects of interest, and to provide an ID value to the objects of interest, as illustrated in FIGS. 9A–9C. However, the objects of interest may appear to have texture, i.e., brightness discontinuities, that may detract from the ability to produce a mask. Accordingly, it is desirable to remove the texture of the objects of interest, step 7306. With particular reference to the image of cells of a cervical Pap smear specimen, it is desirable to remove the texture of the nucleus of any cells appearing in the field of view image. The texture removal may be accomplished on the original image by a grayscale morphological opening, as is known in the art. After the opening, the boundary of the objects of interest are recovered by conditional dilation. Thereafter, the remainder of the images are recovered to provide a non-textured image, step 7308.

The background is then normalized to decrease the difference in contrast between the background and the objects of interest, step 7310. This step is particularly useful for imaging ore cells, or other objects of interest, where the object of interest includes two portions having different levels of brightness, i.e., the nucleus and cytoplasm in the case of cell imaging. The result of the background normalization is to provide a normalized image, step 7312.

The normalized image provided from step 7312 and the non-textured image provided by step 7308 are combined in step 7314 to provide the enhanced image that is part of the result of step 5102. The enhanced object image transformation of step 7314 is performed by transforming the image to eliminate the effect of intensity variation due to nonuniform staining of the specimen. As is known in the art, a Pap smear is performed by staining a specimen to chemically enhance the difference in the transmissivity between portions of the specimen, i.e., the nucleus, the cytoplasm, and the background. However, since the staining can be nonuniform over the specimen, variations in grayscale intensity of the field of view image may result. The image transformation of step 7314 is performed by using Gaussian averaging techniques to mitigate against this nonuniformity. Particularly, the original image is filtered in a binomial filter. The non-textured image is then subtracted from the filtered image to provide the enhanced image, step 7316.

Accordingly, as illustrated in FIG. 10, the result of the contrast enhancement discussed above by reference to step 5102, FIG. 8, is to provide threshold data illustrating the grayscale intensity of various portions of the object of interest and the background, and to provide an enhanced image wherein the contrast between the background and the object of interest is enhanced.

Returning to FIG. 8, the threshold test to identify objects of interest, step 5104, is performed on the enhanced image (produced from step 7316, FIG. 10) using the threshold data (produced from the method of FIG. 13) to produce a binary image. The threshold test is generally one to compare each data word from each pixel of the field of view image data with a predetermined threshold value, and to identify as an object of interest any object having an intensity greater than the predetermined value. However, a feature of the method for identifying objects is that the value of the threshold is varied for each pixel. Stated another way, a threshold image is generated wherein the threshold image includes a threshold intensity value associated with each pixel of the field of view. The threshold test is thus performed by comparing the threshold intensity value associated with a particular pixel with the data word from that pixel. As is known in the art, if the data word is greater than or equal to the threshold intensity value, then the respective pixel of the binary image is assigned a "one" to indicate the presence of an object. Conversely, if the data word is less than or equal to the threshold intensity value, then the respective pixel of the binary image is assigned a "zero" to indicate the absence of an object.

Figure 14:
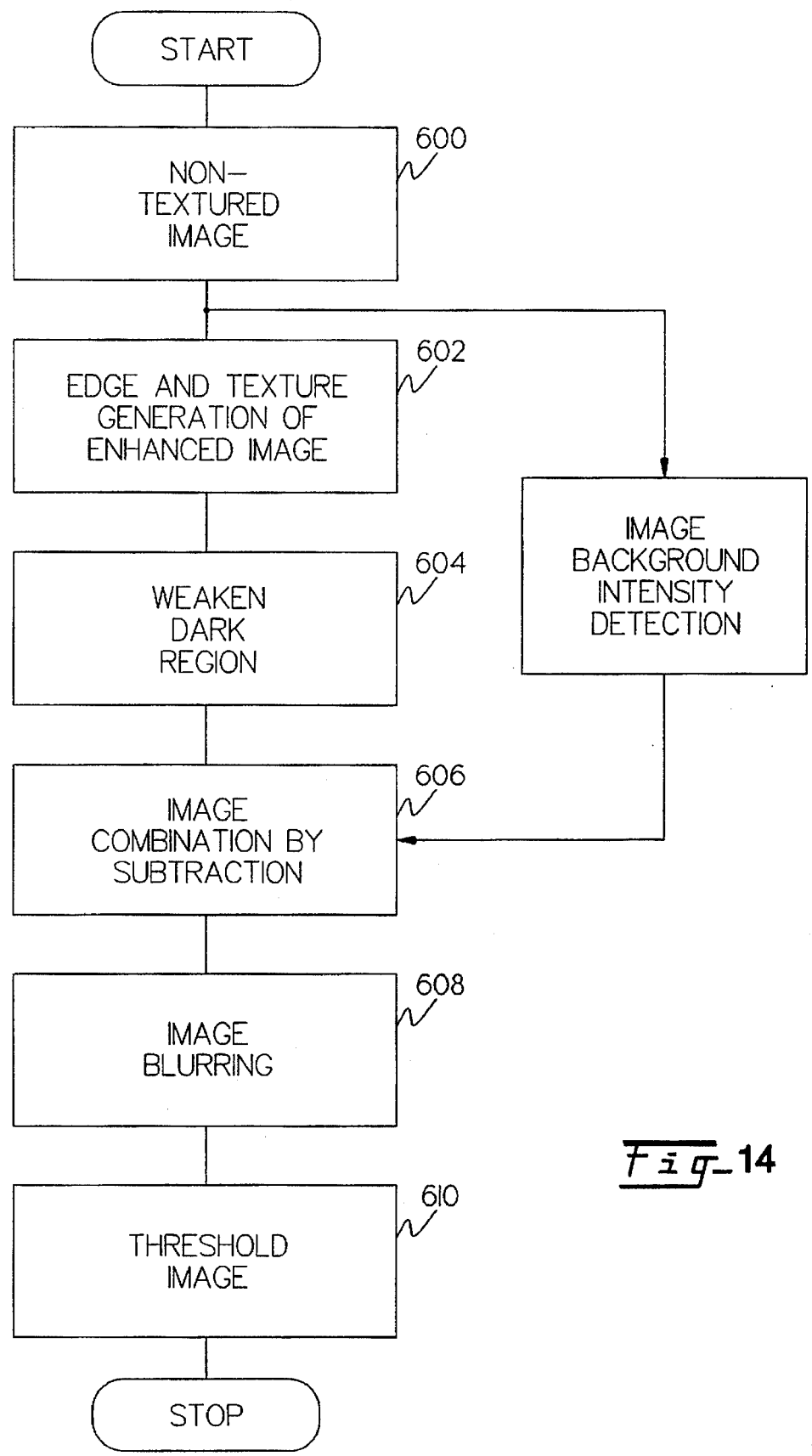
FIG. 14 is a method flow diagram illustrating steps used to create a threshold image.

With reference to FIG. 14, a method for generating a threshold image will be discussed. The threshold image is generated from the non-textured image and the enhanced image. The background of the non-textured image (see step 7308 of FIG. 10) is removed, step 600. Thereafter, the edge and texture of the enhanced image is generated, step 602, and the dark region weakened, step 604. The edge image is determined by a morphological dilation residue operation, and the texture image is derived by the difference of the non-textured image and the original image. The images resulting from step 600 and 604 are combined, step 606, and the combined image blurred, step 608, to produce the threshold image, step 610.

As mentioned above, the threshold image is combined with the original image to identify the objects of interest. The threshold image generated above, as described by reference to FIG. 14, may be used by itself with the original image to identify objects of interest, however, in one embodiment of the present invention, the threshold image is combined with the enhanced image to identify objects of interest. Additionally, as will be described in more detail below, the threshold image is combined with two predetermined offset values to generate three threshold images. A first predetermined offset is subtracted from each grayscale pixel value of the original threshold image to create a low threshold image, and a second predetermined value is added to each grayscale pixel value of the threshold image to create a high threshold image. The low threshold image, high threshold image, and original threshold image are each separately combined with the enhanced image to provide three binary threshold images.

It will be apparent to those skilled in the art that each of the images discussed hereinabove have been grayscale images, i.e., images wherein each pixel may have a range of values representing a variety of intensities. After the threshold images are combined with the enhanced image, as discussed above, the result is a binary image, i.e., an image wherein each pixel represents either the presence or absence of an object. Since the result of the method is to provide a mask, those skilled in the art will appreciate that the binary images produced by combining the threshold images with the enhanced image represents the mask that identifies the shape, size, and position of each object of interest within the field of view.

Still further, those skilled in the art will appreciate that a combination of the original threshold image with the enhanced image will provide a mask that identifies the size, shape, and position, of objects of interest wherein the mask is suitable for most applications. However, in the present application of the method, it is desirable to perform further data processing of the field of view image data to ensure that all objects of interest have been properly identified and are represented in the mask. Accordingly, the three binary threshold images produced as a result of step 5104 (FIG. 8), as discussed above, are refined, step 5106, as will be discussed in more detail below.

Generally, refinement of the binary threshold images begins with the binary threshold image produced by combining the original threshold image with the enhanced image. Data processing is performed to determine whether any artifacts, or non-nucleus, have been identified. The result of these tests are to generate what represents a very close approximation of the desired mask. Thereafter, all objects identified in the high threshold binary image are added into the best approximation mask created above. Lastly, further data processing is performed to determine whether any additional objects of interest are identified in the low threshold binary image that have not yet been incorporated into the mask and, if so, these objects are also incorporated into the mask.

Figure 16:
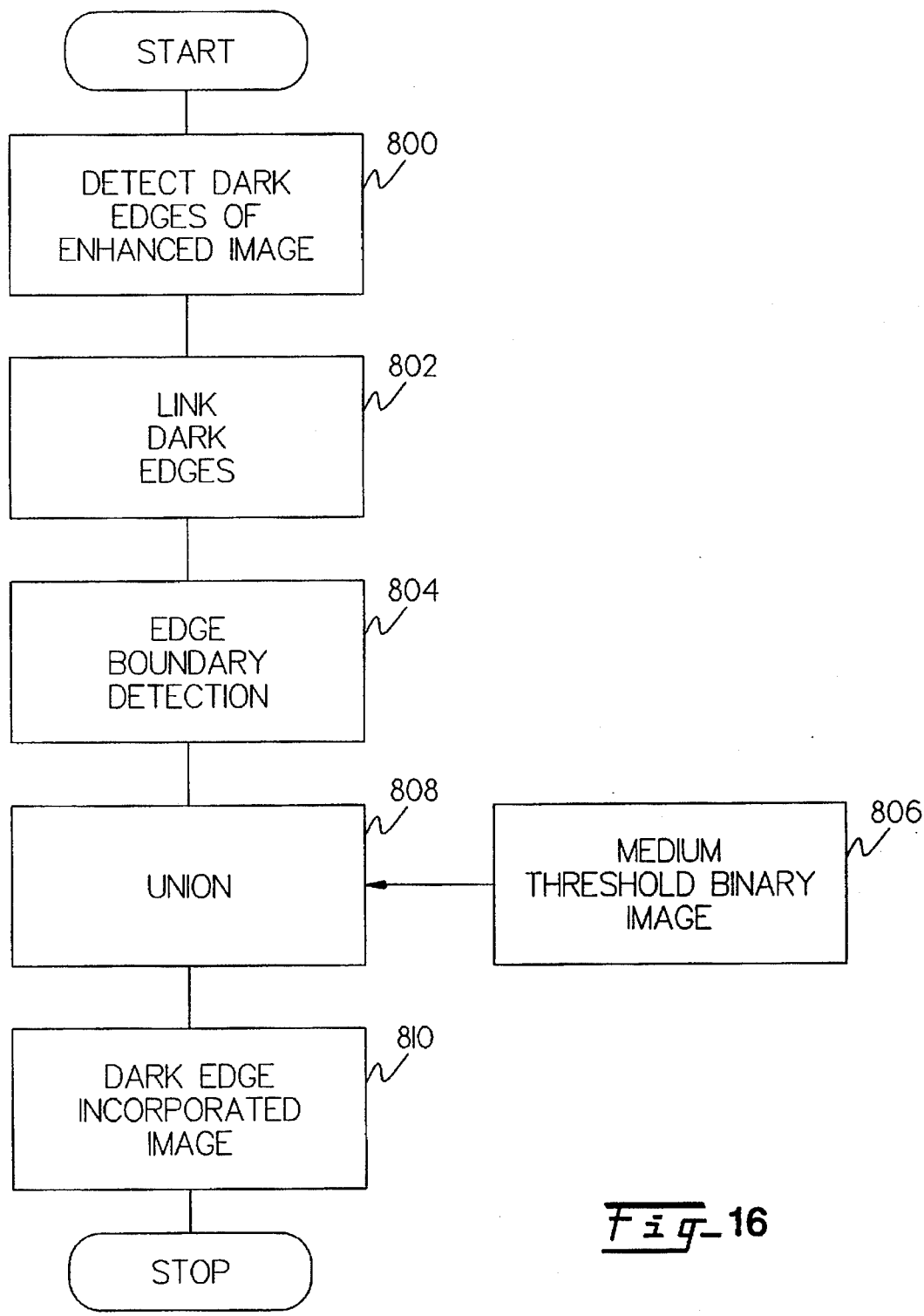
FIG. 16 is a method flow diagram illustrating steps for refining the objects of interest.

To refine the medium threshold binary image, the mask is operated upon to fill any holes. For example, the binary mask that should appear as indicated in FIG. 9B may have holes within objects of interest, as shown in FIG. 15A. The method of FIG. 16 is performed to refine the mask of FIG. 15A to eliminate any holes and provide a mask as illustrated in FIG. 15B. Initially, the dark edges of the objects of interest are identified by morphological erosion residue operations, as illustrated by the intermediate mask of FIG. 15B. To perform the dark edge incorporation, the dark edges of the enhanced image are detected. Dark edge detection may be performed simply by determining where there exists a variation between a pixel and a neighboring pixel. The dark edge is identified as the pixel representing an object of interest. Next, the dark edges are linked using a small morphological closing and subsequent opening to fill in holes in the dark edge, step 802. Thereafter, the boundary of the edge is detected and identified as the true dark edge mask, as illustrated in FIG. 15B. The medium threshold binary image is then combined in a set union with the image created by step 804 to create a dark edge incorporated image, step 810.

Figure 17:
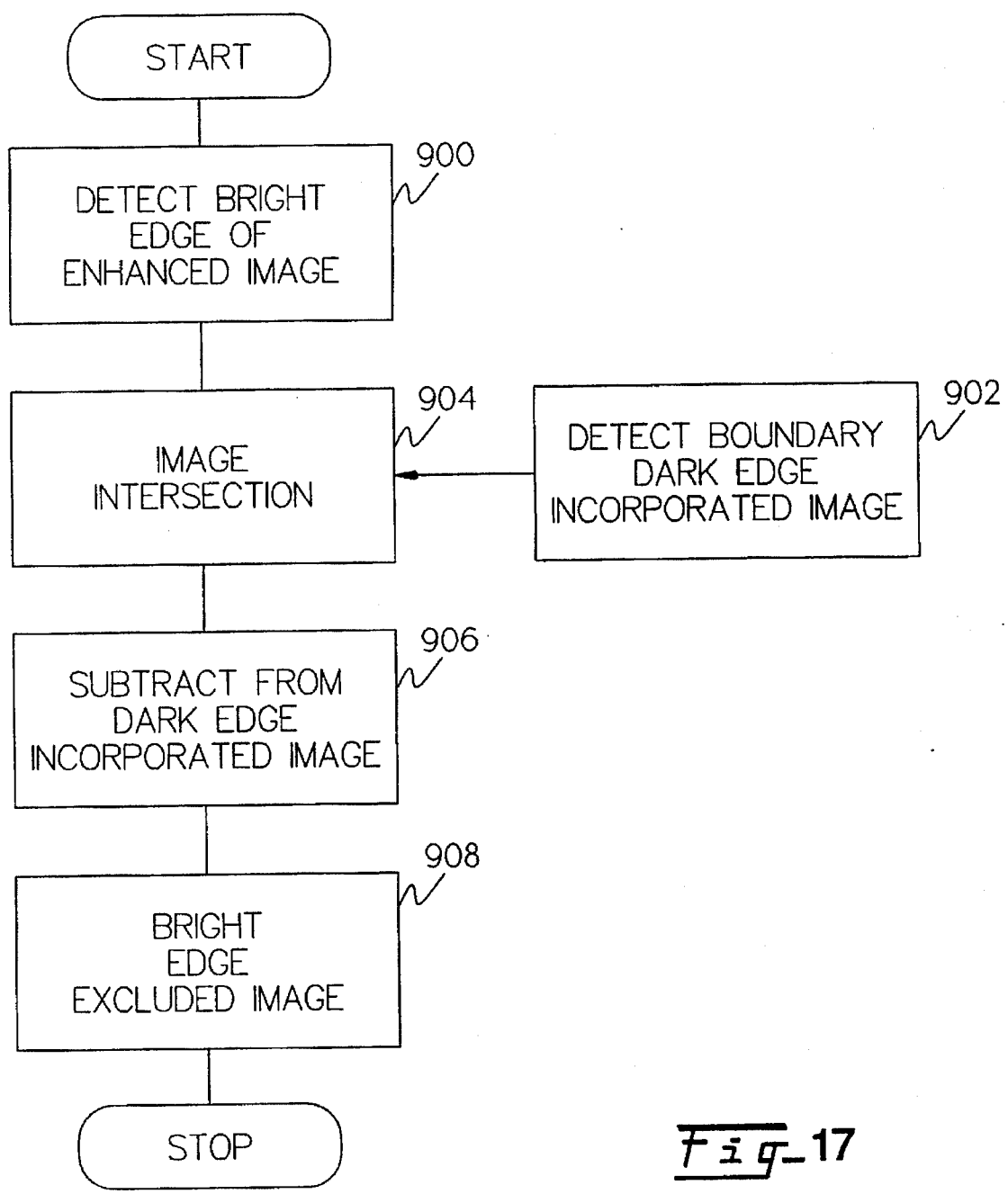
FIG. 17 is a method flow diagram illustrating steps for refining the objects of interest.

Refer now to FIG. 17. In similar fashion, the bright edges of the original image are then excluded from the medium threshold binary image. To this end, the bright edges of the enhanced image are detected, step 900. This is performed in a manner similar to the dark edge detection of step 800, discussed above, except that the edges of the pixels representing the absence of an object are identified as the bright edge. The boundary of the dark edge incorporated image created in step 810, above, is then detected, and the results of step 900 and 902 combine in a set intersection operation. The results of step 904 are then subtracted from the dark edge incorporated image, step 906, to create a bright edge excluded image, step 908. The medium threshold binary image is now represented by the bright edge excluded image.

Figure 18A:
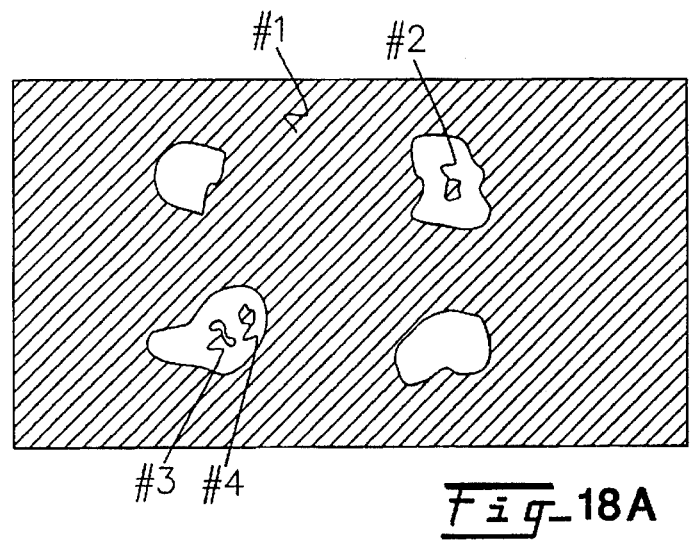
FIGS. 18A, 18B, and 18C are diagrams illustrating a method for eliminating holes in the objects of interest.
Figure 18B:
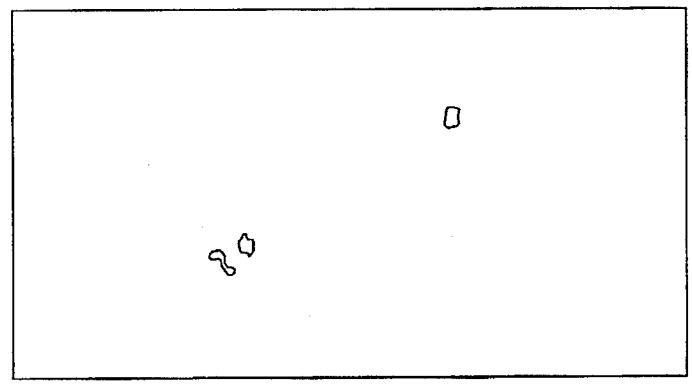

The objects of the bright edge excluded image are completed by filling any holes that may remain. Advantageously, the method is capable of filling holes without connecting close objects. To complete the refinement of the medium threshold binary image, the bright edge excluded image of step 908 is inverted to provide an image, as illustrated in FIG. 18A. Next, the objects of FIG. 18A are detected and labeled by a connected components labeling procedure. Objects are then identified that are larger than a predetermined size, and these objects are excluded from the image to provide an image as illustrated in FIG. 18B. The image thus created is then added to the original image to provide the completed medium threshold binary mask. It will be apparent to those skilled in the art that the predetermined size for excluding objects from the mask of FIG. 18A is selected to be larger than the expected size of objects of interest.

Figure 18C:
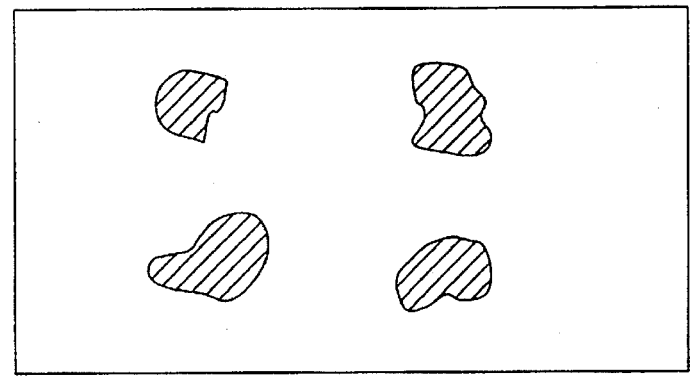

To further complete the medium threshold binary image, data processing is performed to separate objects that may not have been separated using the bright edge detection technique discussed above. To perform the object separation, the objects of the mask created in FIG. 18C are eroded by a first predetermined amount and then dilated by a second predetermined amount wherein the amount of erosion exceeds the amount of dilation, so that the objects after dilation are smaller than they were before erosion. Thus, the connected objects are separated. A morphological closing residue operation is then applied to determine the separation boundary. The separation boundary is then subtracted from the hole-filled image to create the overlap object separated binary image.

To ensure that no objects have been lost due to the above-noted separation, the overlap object separated image is dilated to generate an object mask. Small objects not included in the object mask are combined in a set union with the object separation image to provide an object recovered image.

Lastly, the high threshold binary image and the low threshold binary image are combined with the object recovered image, i.e., the completed medium threshold binary image, to create the final mask. To this end, all objects identified in the high threshold image are added to the completed medium threshold image using a set union operation. The resulting mask is then eroded by a small amount and dilated by a large amount, so that all objects that are identified are connected to a single object. The resulting mask is then combined with the low threshold mask so that any objects identified in the low threshold mask in an area not in close proximity to objects appearing in the completed medium threshold mask are added to the image. These objects are then added to the completed medium threshold image to create the finished mask. A connected components labeling procedure is applied to the finished mask to assign a unique label to each connected object.

METHOD FOR IDENTIFYING NORMAL BIOMEDICAL SPECIMENS, U.S. patent application Ser. No. 07/838,064.

Figure 19:
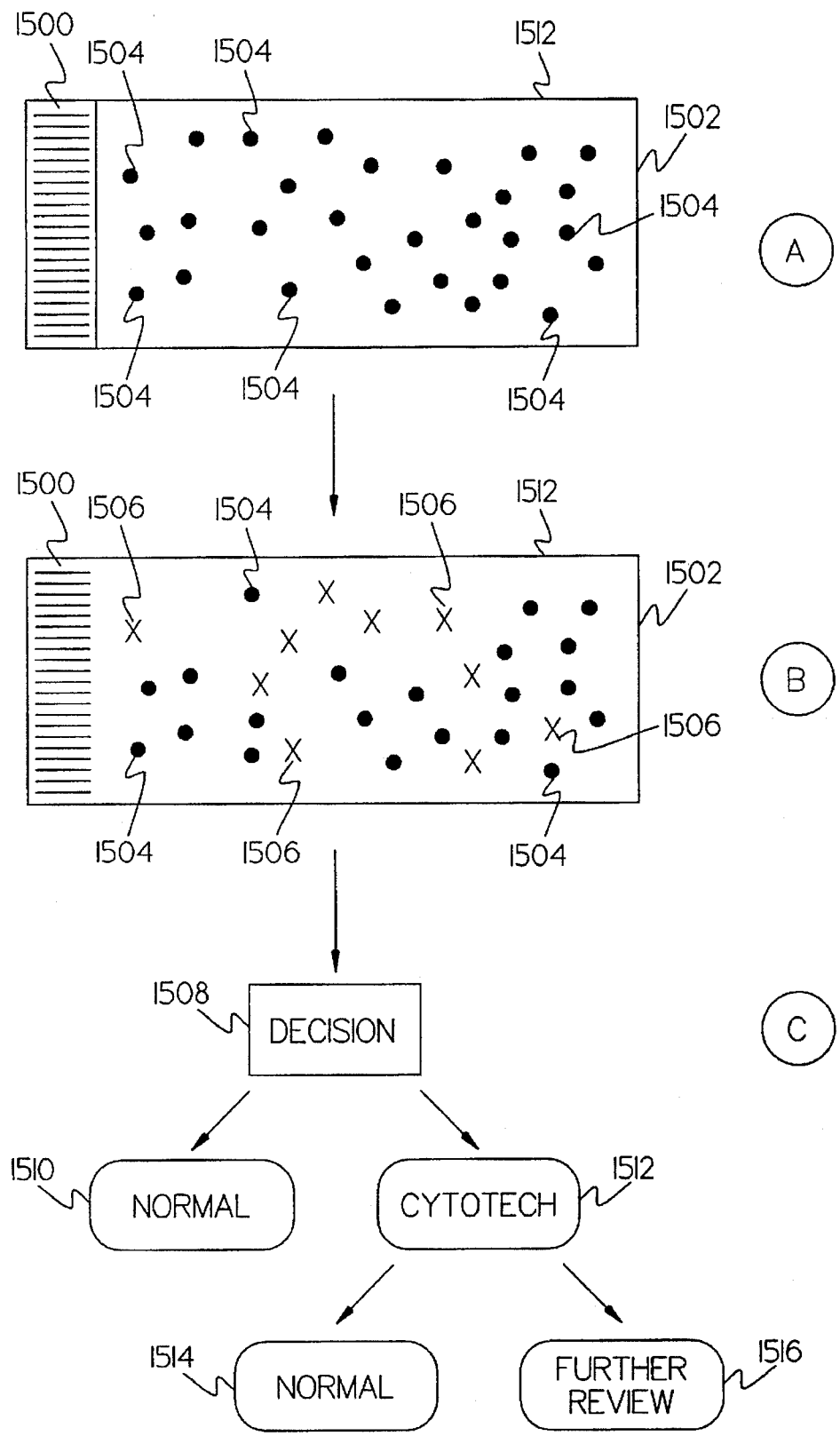
FIG. 19 is a diagram illustrating the general methodology for identifying normal biomedical specimens.

As illustrated in step A of FIG. 19, the specimen may include a plurality of objects 1504. Prior art devices for performing image prescreening are constructed to capture data representing the image of the objects 1504 on the slide 1512 and to analyze the captured image data to identify objects 1506 (step B) that do not appear normal. These prior art devices can store the recorded images of the located objects for review on a CRT by the cytotech.

In contrast, the image gathering and analysis system of the method for identifying normal biomedical specimens goes beyond the steps A and B to analyze the image data representing the objects 1506 and to make a decision, as illustrated at step 1508, as to whether the specimen mounted on the slide 1512 is normal. If the slide is normal, step 1510, the cytotech need not examine the slide. If, however, decision 1508 does not decide that the slide is normal, it is analyzed by the cytotech, step 1512, for an independent opinion of whether the slide is normal, step 1514, or whether the slide requires further review, step 1516.

Figure 20A:
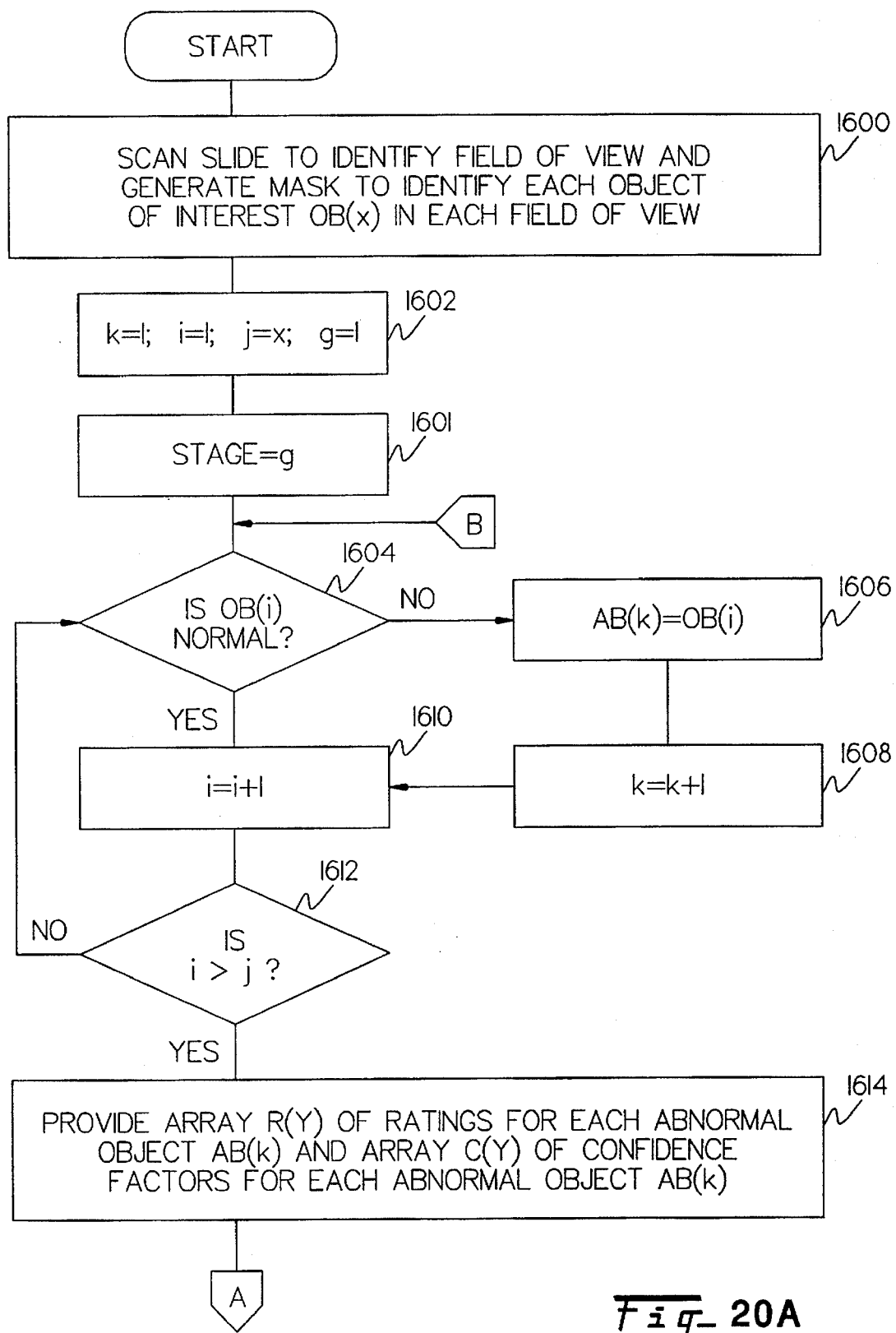
FIG. 20A and FIG. 20B are intended to be pieced together to show an illustrative flow diagram illustrating in more detail a method for identifying normal biomedical specimens.
Figure 20B:
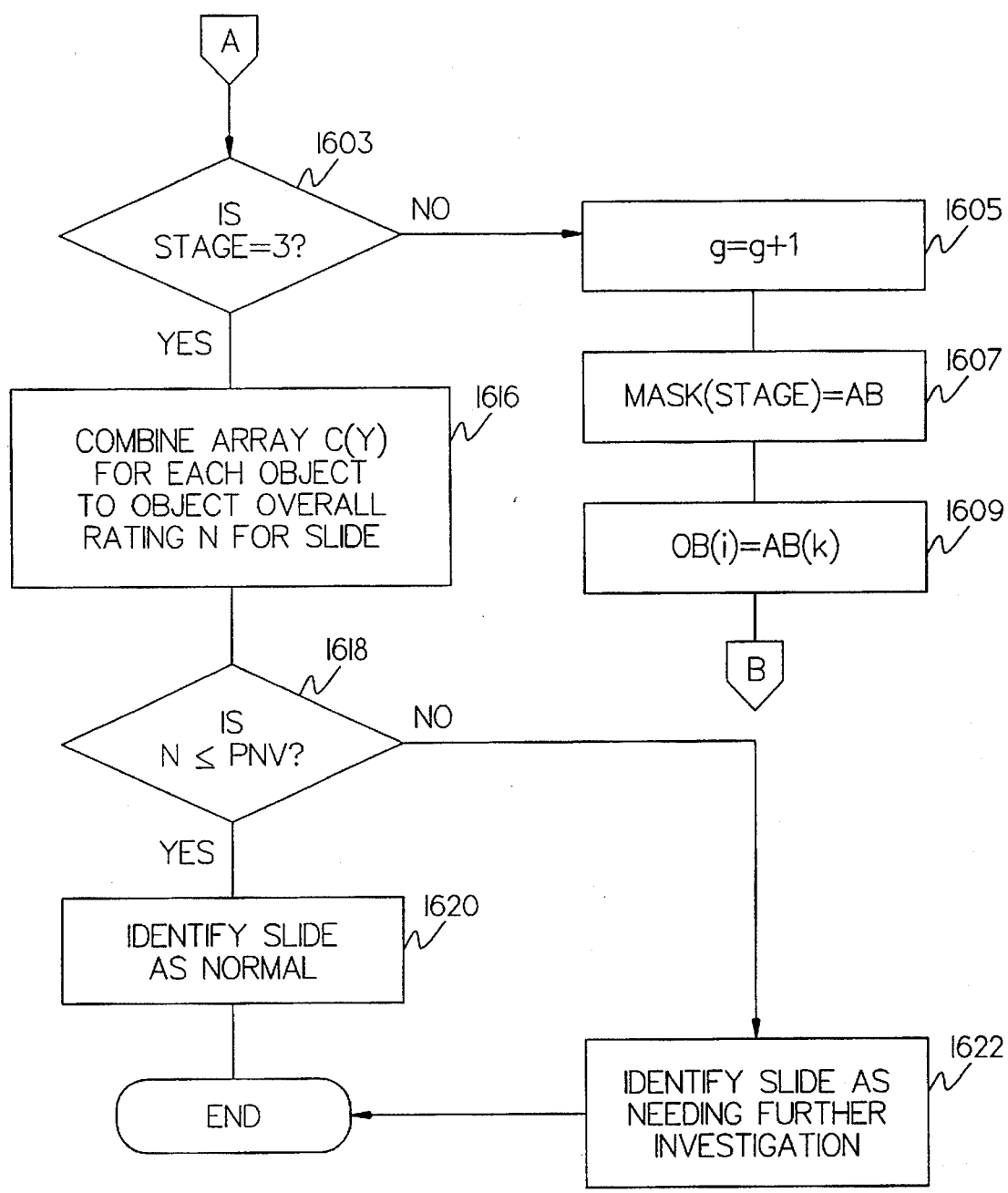

To implement the methodology illustrated in FIG. 19, the present invention performs the method steps illustrated in FIGS. 20A and 20B. Therein, the data processor provides control signals to the imaging system 502 (FIG. 1A) to scan the slide 1512 to provide the image data. The data processor 550 then processes the image data to identify objects of the specimen on the slide. It will be apparent to those skilled in the art that each object may comprise a cell, a group of cells, or an artifact. At step 1600 the data processor controls the imaging system to scan the slide a first time at a first magnification to determine which fields of view contain objects. The data processor controls the imaging system to scan the slide a second time at a higher, second magnification to obtain field of view image data representing the fields of view identified during the first scan. In this fashion, various resolutions of the image data are obtained.

As described above, for each set of field of view image data provided, the data processor generates a mask to identify each object of interest within the field of view. The mask thus generated includes a number of object identifiers OB(x), so that the mask can be combined with the original field of view data to generate data characterizing each object OB.

After the mask has been generated to identify the objects OB(x) in the field of view, variables are initiated for use in the method, step 1602. The variables k, i, and g are index variables and are initially set equal to 1. The variable j is used to identify the number of objects x in the mask of objects of interest. In one embodiment of the invention, the objects of interest are classified in three stages. Accordingly, a variable stage is set equal to g, step 1601, to record the present stage of evaluation. The mask of objects of interest OB for the first stage is therefore referred to as a stage mask.

Each object is then examined to determine whether the object appears normal or abnormal, step 1604. The determination of whether the object appears normal or abnormal is made by measuring a number of features of the object to characterize the object. Examples of features that may be measured to characterize the object, and thereby determine whether the object is normal include the object size, shape, density, and texture. In one embodiment of the invention, wherein the image gathering and analysis system is used for cervical Pap smear analysis, features of neighboring objects are measured to determine whether a subject object is normal. Examples of features of neighboring objects that can be measured are the number of abnormal objects proximate the subject object in addition to the number of total objects proximate the subject object. Additional features of neighboring objects may be measured, in other applications, to determine whether the subject object is normal.

It will be apparent to those skilled in the art that, although certain features have been described herein for use in determining whether a cervical Pap smear cell is normal, other features may be substituted therefor. Further, where the method for identifying normal biomedical specimens is applied to other fields of cytology, histology, or other image analysis areas, various other features, and feature combinations, may be desirable to determine whether a given object is normal or abnormal.

Regardless of the features selected, the feature measurements are combined as will be discussed below, and a determination made wherein the object appears normal or abnormal, step 1604. If the object appears abnormal, then the image data representing a mask of the object is recorded in an array AB(k), step 1606. Thereafter, the index variable k is incremented, step 1608. Alternatively, if the object appears normal, step 1604, then the index variable i is incremented, step 1610, and the variable i is compared to the variable j to determine whether all objects of the mask of objects of interest have been examined, step 1612. Steps 1604–1612 are repeated until all objects have been examined, at which point the array AB(k) includes image data identifying each object in the field of view that did not appear normal.

The image data representing the abnormal objects is used to create a stage 2 mask to identify the size, shape and location of the abnormal objects from the stage 1 mask. Those skilled in the art will appreciate that the stage 2 mask identifying the abnormal objects may be created in number of ways. As examples, the normal objects may be subtracted from the stage 1 mask so that objects identified as being abnormal remain. Alternatively, the stage 2 mask may be created by adding data representing the abnormal objects in the stage 1 mask to a blank mask. As still another alternative, the stage 1 mask may be refined by additional image processing on the original grayscale image to produce the stage 2 mask. Other methods for creating the stage 2 mask will readily become apparent to those skilled in the art.

So that steps 1601–1612 are repeated for three stages, the variable Stage is compared to three to determine if the third stage has been completed, step 1603, and, if not, the index variable g is incremented by 1, step 1605, the objects of the stage 2 mask indicated at step 1607 are stored in the object of interest array OB 1609. (FIG. 20B)

In accordance with one embodiment of the invention, different features are measured during each sequential stage to determine whether objects are normal or abnormal. As an example, abnormal objects may be identified by measuring their size and shape during stage 1. Any objects identified as abnormal during stage 1 will be measured during stage 2 to determine whether they are actually abnormal. During stage 2, the texture and density of the object may be measured to determine whether the object is normal or abnormal. Any objects identified as abnormal during stage 2 will be measured during stage 3 to determine whether they are normal or abnormal. During stage 3, the number of abnormal objects proximate the subject object and the total number of objects proximate the subject object may be measured to determined whether the object is normal or abnormal.

In determining whether an object is normal or abnormal, in either stage 1, stage 2, or stage 3, the feature measurements for the object are input into a modified binary decision tree wherein the terminal node of the decision tree identifies a region of the feature space used as the decision tree input. Particularly, each terminal node is assigned predetermined confidence values so that if the measurements of an object results in a particular terminal node of the binary tree, the predetermined confidence values are assigned to that object. In one embodiment of the invention, each terminal node assigns three confidence values to each object. One value is assigned to indicate the probability that the object is an artifact, another confidence value is assigned to indicate the probability that the object is a normal cell, and a third confidence value is assigned to indicate the probability that the object is abnormal. In one embodiment of the invention, the confidence value of the greater magnitude is used to determine whether the object is an artifact, normal cell, or abnormal cell. However, those skilled in the art will appreciate that the confidence values may be compared, combined, or used in various ways to classify the objects as normal, abnormal, or artifacts. Further, it will be apparent that other confidence values may be assigned to provide other or different classifications. Also, although a binary decision tree is used to combine the feature measurements, other data processing methods could be substituted here as well.

In this regard, the objects are classified with respect to features that are related to other objects on the slide in addition to being classified with respect to features such as those discussed above, that are related to the object itself. As an example, an object may receive a neighborhood feature measurement that is related to its neighboring objects. If the objects neighboring the subject object appear abnormal in size or shape, then the neighborhood feature measurement of the subject object will indicate relative abnormality. Conversely, if the neighboring objects all appear as normal cells, then the neighborhood feature measurement of the subject object will indicate relative normality. Similarly, each object may be given a numbers feature measurement indicating the normality of the object by reference to the number of cells neighboring the object. In this regard, if the number of cells neighboring the object are within a predetermined range, then the object will be given a numbers feature measurement indicating relative normality. Conversely, if the number of objects neighboring the subject object falls outside the predetermined range, then the object will be given a numbers feature measurement indicating relative abnormality.

With respect to the feature measurements provided the plurality of objects AB(k) that do not appear normal, each measurement may vary over a predetermined range so that a range of values can be assigned to the object. Further, those skilled in the art will readily appreciate that other features, both the features relating to the object and features relating to neighboring objects or conditions may be provided in addition to those features discussed herein. However, an important aspect of the classification method is that not only is the subject object classified in accordance with features relating to the subject object, but the subject object is classified in accordance with features external to the subject object. This allows a more accurate determination of whether the specimen as a whole is normal or abnormal.

Returning to FIGS. 20A and 20B, after stage 3 has been completed, the processor of the image gathering and analysis system includes classification data for each stage wherein the classification data identifies the number of normal objects identified during that stage, the number of abnormal objects identified during that stage, and the number of artifacts identified during that stage. To make the determination of whether the overall slide appears normal, the classification data is combined to provide an overall rating N for each slide, step 1616. The overall rating is then compared to a predetermined normal value PNV and, if the overall rating is less than, the predetermined normal value, then the slide is identified as normal, step 1620. If, however, the overall rating N is greater than or equal to the predetermined normal value, then the slide is identified as a slide needing further investigation, step 1622, and must be reviewed by a cytotech.

The classification data may be combined in a plurality of manners to provide the overall rating N. Similarly, a plurality of normal values, PNV, may be selected wherein the relative magnitude of the normal value will determine, in part, the accuracy of the method. A presently preferred method for combining the classification data to determine whether the slide is normal is to provide two classification factors $f_1$ and $f_2$ wherein the classification factors are defined as follows:

$$f_1 = \frac{\text{No. of stage 3 abnormal objects}}{\text{No. of stage 2 abnormal objects}}$$

and wherein $$f_2 = \frac{\text{No. of stage 3 abnormal objects}}{\text{No. of stage 1 normal objects +}}$$
$$\text{No. of stage 2 normal objects +}$$
$$\text{No. of stage 3 normal objects}$$

The overall rating N for the slide is then defined as an anomaly score as follows:

$$\text{anomaly score} = \Omega_1 f_1 + \Omega_2 f_2$$

wherein $\Omega_1$ and $\Omega_2$ are predetermined constants.

It will be apparent to those skilled in the art that the classification data may be combined in a number of ways to determine the overall rating for the slide. As examples, the number of normal objects for each stage may be compared to the number of artifacts and/or the number of abnormal objects. As another example, the number of abnormal objects for the various stages may be compared to the number of normal objects for the various stages. Still further, the confidence factors may be used in combination with the classification data to provide the overall rating for the slide. Those skilled in the art will appreciate that a wide variety of ways of combining the classification data and the confidence factors to provide an overall rating for the slide may be obtained.

A METHOD AND APPARATUS FOR ROBUST BIOLOGICAL SPECIMEN CLASSIFICATION, U.S. patent application Ser. No. 08/309,209

In this section, a method to achieve the balance between accuracy and robustness of an automated system is disclosed. To achieve the accuracy of the system, a distributed processing method is used. Multiple classifiers are designed, each is specialized in a specific range of feature variations to maximize its accuracy in that range. An information integration method is designed to integrate the highly accurate performance in each range into a highly robust and accurate system that performs over a full range of feature variations. The method described in this invention comprises three major steps: (1) determination of the overall classifier structure, (2) distributed classifier development, and (3) multiple classifier integration.

The block diagram is an example based on four distributed clusters. In the block diagram, the cluster membership generator generates the membership values for each classifier, $\mu_1$, $\mu_2$, $\mu_3$, and $\mu_4$. Each classifier generates the possibilities, or probabilities of being abnormal for each slide. The possibility of the abnormal for each classifier can be biased, so an offset value is introduced to compensate the bias effects.

Figure 21:
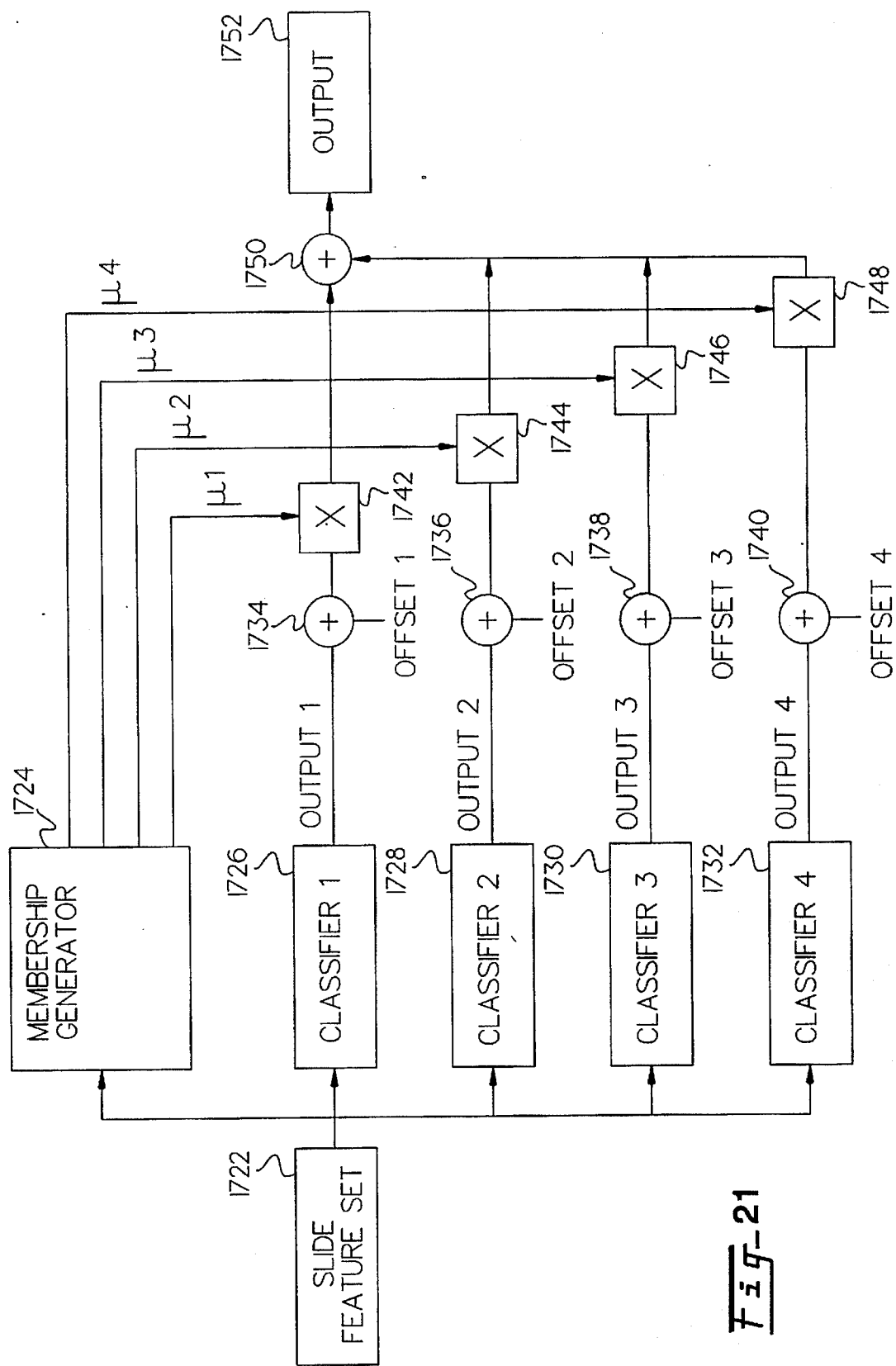
FIG. 21 shows a block diagram of a robust classifier of the invention.

Refer now to FIG. 21 which shows a block diagram of a robust classification apparatus. The slide feature set 1722 is input to a membership generator 1724, a first classifier 1726, a second classifier 1728, a third classifier 1730, and a fourth classifier 1732. The slide feature sets are used by the classifiers to provide an output that classifies the particular feature subset selected by the classifier. The outputs of each classifier are offset by predetermined offsets that are used to adjust to variations in the feature set. The resulting outputs of the weighted outputs of each classifier are added together using the summer 1750 to aggregate classification output 1752.

To determine the classifier structure, data is acquired from multiple sources with as wide a sell of variations as possible. The gathered data are used to establish data clusters. The slide specimens within each cluster have very similar characteristics. Unsupervised clustering methods can be used to determine the number of clusters and data may be assigned to each cluster. The unsupervised clustering algorithm provides the clusters which have a similar characteristic within each cluster. The most popular and general methods of the unsupervised clusterings are disclosed in J. T. Tou and R. C. Gomalez, *Pattern Recognition Principles*, Addisson-Wesley Publishing Company, 1974. An isodata algorithm, fuzzy isodata algorithm, and k means clustering algorithm, fuzzy c means clustering. This method is based on the distance metric in feature space or performance space. In a training stage, if a priori information cornering the slide is not available, the unsupervised clustering algorithm on the feature space can be used. However, if a priori information is available, for example, knowledge of the staining method, sampling method, or laboratory information, an unsupervised clustering algorithm on the performance space may be used rather than the feature space. The method in one embodiment of the invention uses the following as a performance metric. The cluster is built from the available slides and the performance in sensitivity and specificity is examined. The specificity and sensitivity as an ordered pair, forms the performance space. The performance metric is used to group slides of different known variations such as staining difference into difference clusters.

In the cases where no a priori information is available for the samples, the clustering can be done based on feature distributions. The features that a clustering method may use include but are not limited by the darkness of the slide stain which reflect the staining method used, nuclear size which could reflect the slide preparation method used, or the risk group that patients are from. This clustering result determines the number of classifiers needed and the range of feature variations that each classifier will be specialized in. This is the major step to reduce the performance variation and degradation due to variations of the characteristics of the slides.

Given these clustering results, all the available slide characteristics are searched for the indicators, features, that can best predict which cluster each slide will belong to. With these indicators and the given cluster, the membership generator 1724 shown in FIG. 21 is built. This membership generator would assign membership values $\mu_i (0 \leq \mu_i \leq 1)$, which are the possibilities, or probabilities that a specimen has originated from cluster i. Since the sum of the membership values is not necessarily equal to one, the membership values are normalized by the sum of the membership values. For example, if the membership values are $\mu_1, \mu_2, \ldots \mu_c$, then the normalized membership value is:

$$\mu_i \leftarrow \mu_i / \sum_{c=1}^{C} \mu_c$$

Based on the clustering results, a classifier is developed for each cluster. The data used to train each classifier are all the available data samples of all clusters, however, each sample is weighted by a factor which is the cluster membership value $\mu_i$ computed in the first step. This enables a proportionate and smooth contribution of each data sample to the classifier that is designed to be specialized for the cluster. Using this method, the variation of the overall result can be reduced in comparison to other methods using a clear-cut, exclusive training data set for each classifier. The methodology used for the classifier construction is not limited, although in one embodiment fuzzy type of classifiers may be used.

One fuzzy type classifier is the binary fuzzy decision tree. The structure of binary fuzzy decision tree is the same as the conventional binary decision tree. However, the operations of the nodes and links are different. The following is an example of the operation.

In a nonterminal node, let $\bar{x}$ be an input feature vector; and $\bar{w}$ be the selected unit projection vector. $P_L(P_R)$ and $\sigma_L(\sigma_R)$ be the mean and standard deviation of the projection scalars derived from the training population that went to the descending node. The conditional possibilities of reaching the direct left and right descending nodes from the nonterminal node, $\mu_L$, $\mu_R$, are computed based on the following equations. Note that the conditional possibility of reaching root node Q is 1.

$$\mu_L(\bar{x}) = 1 - \mu_R(\bar{x}) = \frac{1}{1 + \text{fax}(x)} \text{ where fax}(\bar{x}) =$$

$$\frac{\sigma_L}{\sigma_R} \exp\left[\frac{1}{2k^2}\left(\frac{\eta_L}{\sigma_L^2} - \frac{\eta_R}{\sigma_L^2}\right)\right] \text{ and}$$

$$\eta_L = \begin{cases} (p - p_L)^2; & (p - p_L)(p_R - p_L) > 0 \\ 0; & \text{otherwise} \end{cases} \text{ and}$$

$$\eta_R = \begin{cases} (p - p_R)^2; & (p - p_R)(p_L - p_R) > 0 \\ 0; & \text{otherwise} \end{cases}$$

$p = \bar{w}^T \bar{x}$ and k is the adjustment factor for the conditional possibility function. If k=1, then the possibility becomes probability under the Gaussian distribution assumption.

The link operation depends on the structure of the tree. From the structure of the tree, the parent node and child node relationship along any path from the root node to a terminal node is defined. To estimate the possibility of reaching a certain terminal node i, borrowing from the Baysian conditional probability, multiply the conditional possibility value of each node along the path from the root node to terminal node i:

$$\text{poss}(i, \bar{x}) = \prod_{j=1}^{N} \mu_{sj}(j, \bar{x})$$

where $_{sj}$ is L(R) if $(j-1)^{th}$ ascendant is left (right) side of $j^{th}$ ascendant.

Given a fixed tree structure, the evidence values of terminal nodes based on a training data set are computed.

The evidence values are the probability that $\bar{x}$ belongs to different classes for each terminal node, based upon the training data. If the possibilities of terminal nodes are $$poss(0,\bar{x}), poss(1,\bar{x}), \ldots, poss(T,\bar{x})$$

and their associated evidence values of class c are $$evid(0,c), evid(1,c), \ldots, evid(T,c),$$

then the membership to a given class c is $$mem(c, \bar{x}) = \sum_{i=0}^{T} poss(i, \bar{x}) \cdot evid(i, c)$$

For the membership generator, the outputs of the membership generator are mem(c,$\bar{x}$), $1 \leq c \leq C$. For the classifiers, the outputs from each of the classifiers are mem(c,$\bar{x}$), where c is an abnormal class.

Figure 22:
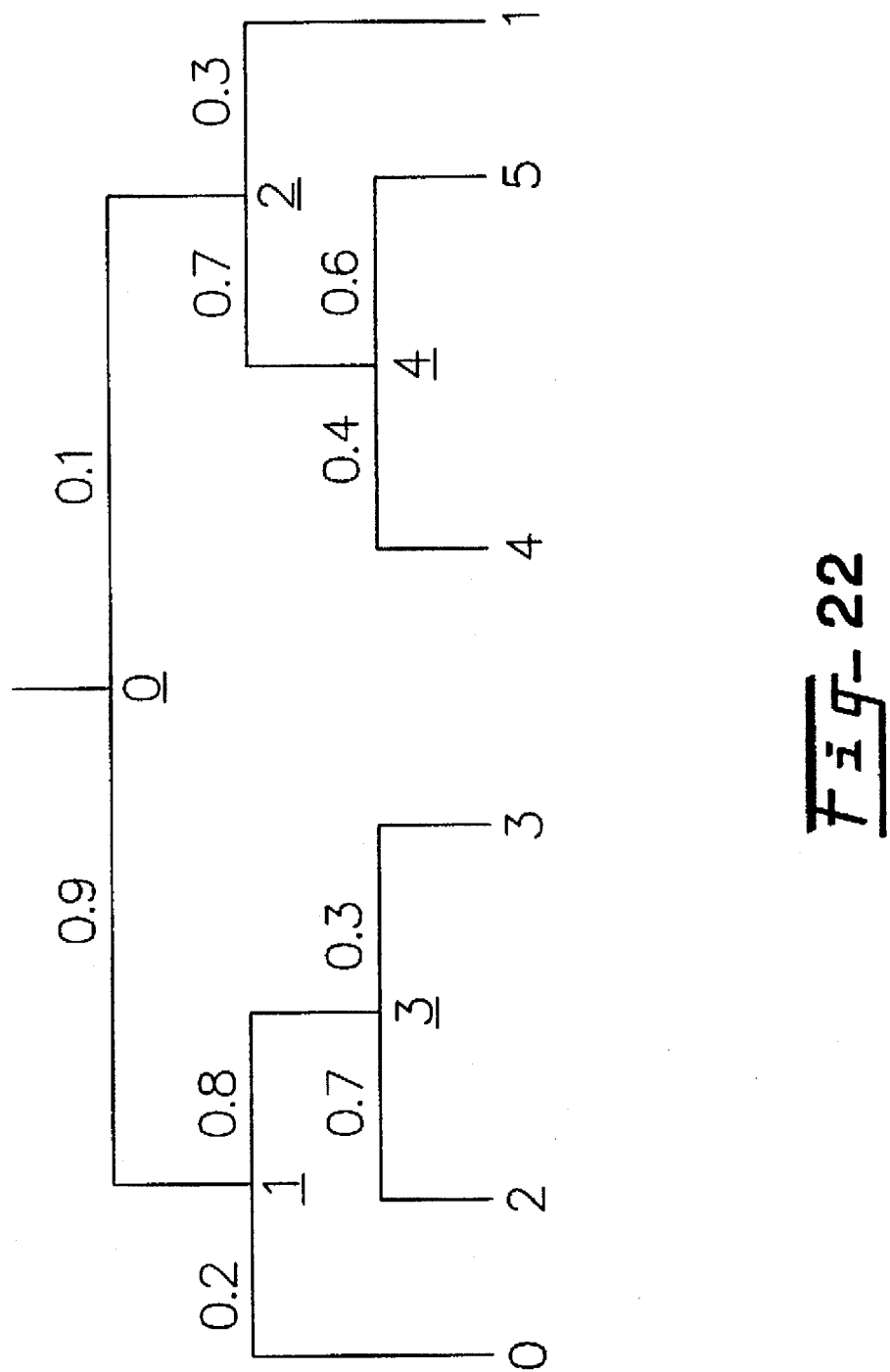
FIG. 22 shows an example decision tree.

To explain the operations of the tree, a hypothetical example is provided. One example tree structure is shown in FIG. 22. Given an input feature vector $\bar{x}$ we further assume the computed conditional possibilities of each nonterminal node. For example, $\mu_L$, $\mu_R$ of nonterminal node $\underline{0}$ are 0.9 and 0.1.

Based on the above conditional possibilities, the possibility value for each terminal node is:

poss(0,$\bar{x}$): 0.9·0.2=0.18 poss(1,$\bar{x}$): 0.1·0.3=0.03 poss(2,$\bar{x}$): 0.9·0.8·0.7=0.504 poss(3,$\bar{x}$): 0:9·0.8·0.3=0.216 poss(4,$\bar{x}$): 0.1·0.7·0.4=0.028 poss(5,$\bar{x}$): 0.1·0.7·0.6=0.042

The following are the evidence values for each terminal node:

| Terminal Node # | Class 0 | Class 1 | Class 2 | Class 3 |
|---|---|---|---|---|
| 0 | 0.35 | 0.45 | 0.08 | 0.12 |
| 1 | 0.04 | 0.03 | 0.50 | 0.43 |
| 2 | 0.34 | 0.34 | 0.15 | 0.17 |
| 3 | 0.23 | 0.20 | 0.30 | 0.27 |
| 4 | 0.27 | 0.24 | 0.26 | 0.23 |
| 5 | 0.16 | 0.10 | 0.40 | 0.34 |

The membership value for each class is:

mem(Class0,$\bar{x}$):
0.35·0.18+0.04·0.03+0.34·0.504+0.23·0.216+0.27·0.028+ 0.16·0.042=0.300 mem(Class1,$\bar{x}$):
0.45·0.18+0.03·0.03+0.34·0.504+0.20·0.216+0.24·0.028+ 0.10·0.042=0.307 mem(Class2,$\bar{x}$):
0.08·0.18+0.50·0.03+0.15·0.504+0.30·0.216+0.26·0.028+ 0.40·0.042=0.194 mem(Class3,$\bar{x}$):
0.12·0.18+0.43·0.03+0.17·0.504+0.27·0.216+0.23·0.028+ 0.34·0.042=0.199

The information produced by the distributed classifiers are integrated by the following method. Using the membership values and the results of the classifier for each clusters, the final result is computed as:

$$output = \frac{\sum_{c=1}^{C} \mu_i(output_i - offset_i)}{\sum_{c=1}^{C} \mu_i}$$

where output and $output_i$ are the final classification result and result of classifier i. The $offset_i$ is an offset value to adjust the bias value of classifier i. The bias is adjusted to achieve a balance of the accuracy and robustness. The above is for the operation of the classifier.

APPARATUS FOR AUTOMATED IDENTIFICATION OF CELL GROUPINGS ON A BIOLOGICAL SPECIMEN, U.S. patent application Ser. No. 08/309,061

Figure 23:
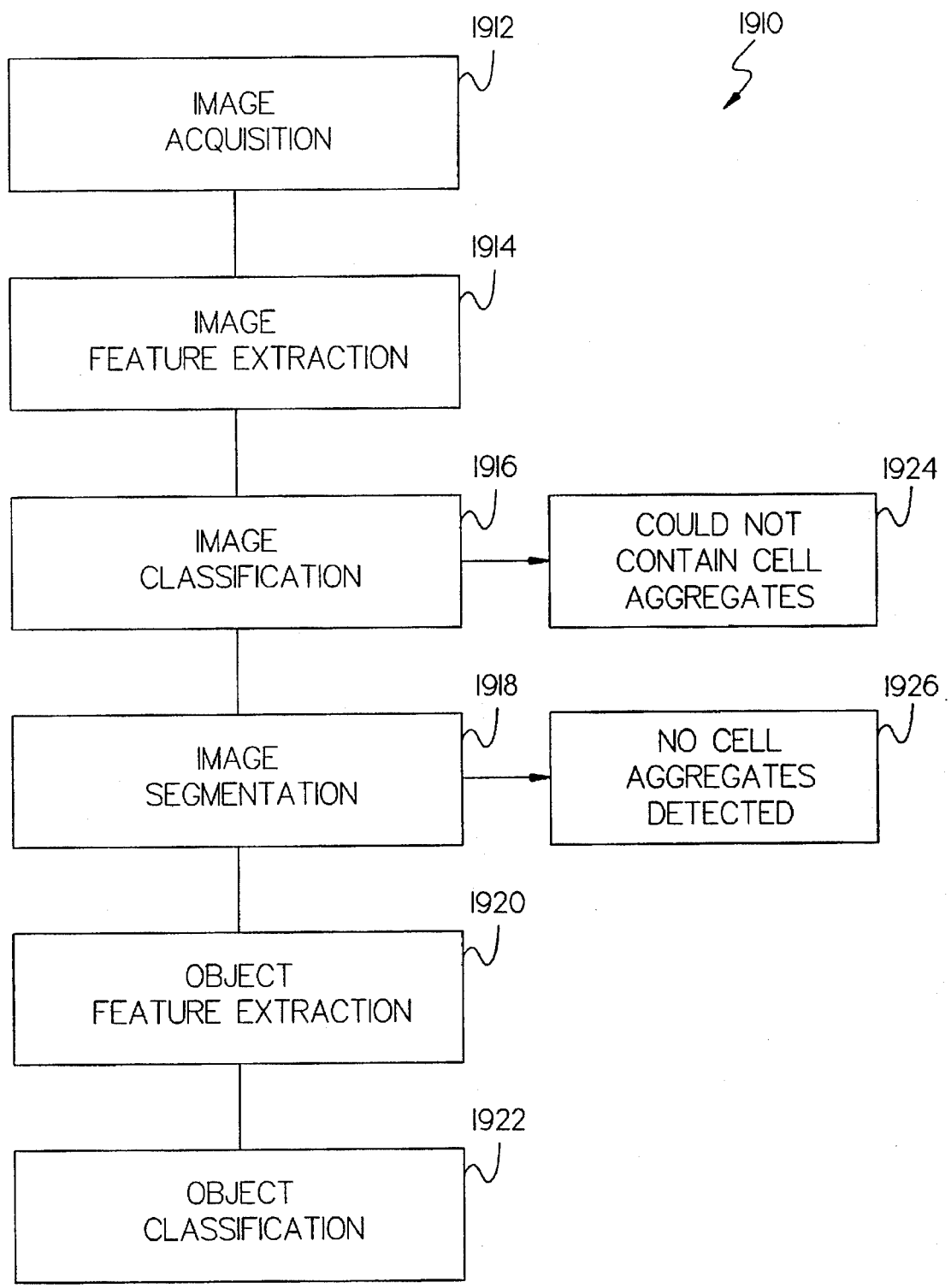
FIG. 23 shows a process flow diagram of the image processing and analysis performed for each image of biological specimens.

Refer now to FIG. 23 which shows a process flow diagram of a method employed by the invention to analyze cellular aggregates. An image is acquired in step 1912. In one embodiment of the invention, the image is acquired using a digital camera attached to a microscope as shown in FIGS. 1A, 1B and 1C. The image acquired by the camera is of the cytologic specimen, magnified by an objective lens of 20× magnification. The camera digitizes the image to 512 by 512 pixels to a depth of 8 bits. The magnification of 20× and an image size of 512 by 512 pixels is by way of example and not limitation, and one skilled in the art will appreciate that other magnifications and image sizes may be used without departing from the scope of the invention.

Since cellular aggregates may not exist in every acquired image, and since it is important to process images rapidly, the invention avoids extensive processing of images that contain no material of interest. Image feature extraction 1914 and image classification 1916 show the process to achieve rapid removal of unproductive images. Features and properties of the image are measured in image feature extraction in step 1914. The measured features are then used to determine if the image may contain identifiable cellular aggregates. In one embodiment, if a characteristic called AverageHighPixelValue is greater than 240, then the image is rejected. AverageHighPixelValue may be defined as the average intensity value of all pixels with pixel counts above 200 in an image where 0 is black and 255 is white. The AverageHighPixelValue rule will identify images with very little cellular material. Such images have little chance of representing a cellular aggregate.

Additionally, if:

(SmallDarkEdgeAverage*35000)+HighPixelCount<15000, then the image is rejected, where SmallDarkEdgeAverage may be defined as the average value of image subject to a 5×5 closing residue operation, SmallDarkEdgeAverage =

$$\frac{1}{N_{Pixels}} \sum_{All_{Pixels}} (((I_{orig} \oplus (5 \times 5)) \ominus (5 \times 5)) - I_{orig})$$

where $N_{Pixels}$ is the number of pixels in the image, $All_{Pixels}$ indicates that the summation covers all pixels in the image, $I_{Orig}$ is the original image, $\oplus$ is the morphological dilation operator (for example, as disclosed in Serra, J., "Image Analysis and Mathematical Morphology", Academic Press, 1982), $\ominus$ is the morphological erosion operator, closing residue is represented by the operation enclosed in parenthesis above, and HighPixelCount is the number of pixels with pixel counts above 200 in the original image. The SmallDarkEdgeAverage rule will identify images with so much material that reliable detection and identification of cellular aggregates is unlikely.

Figure 24:
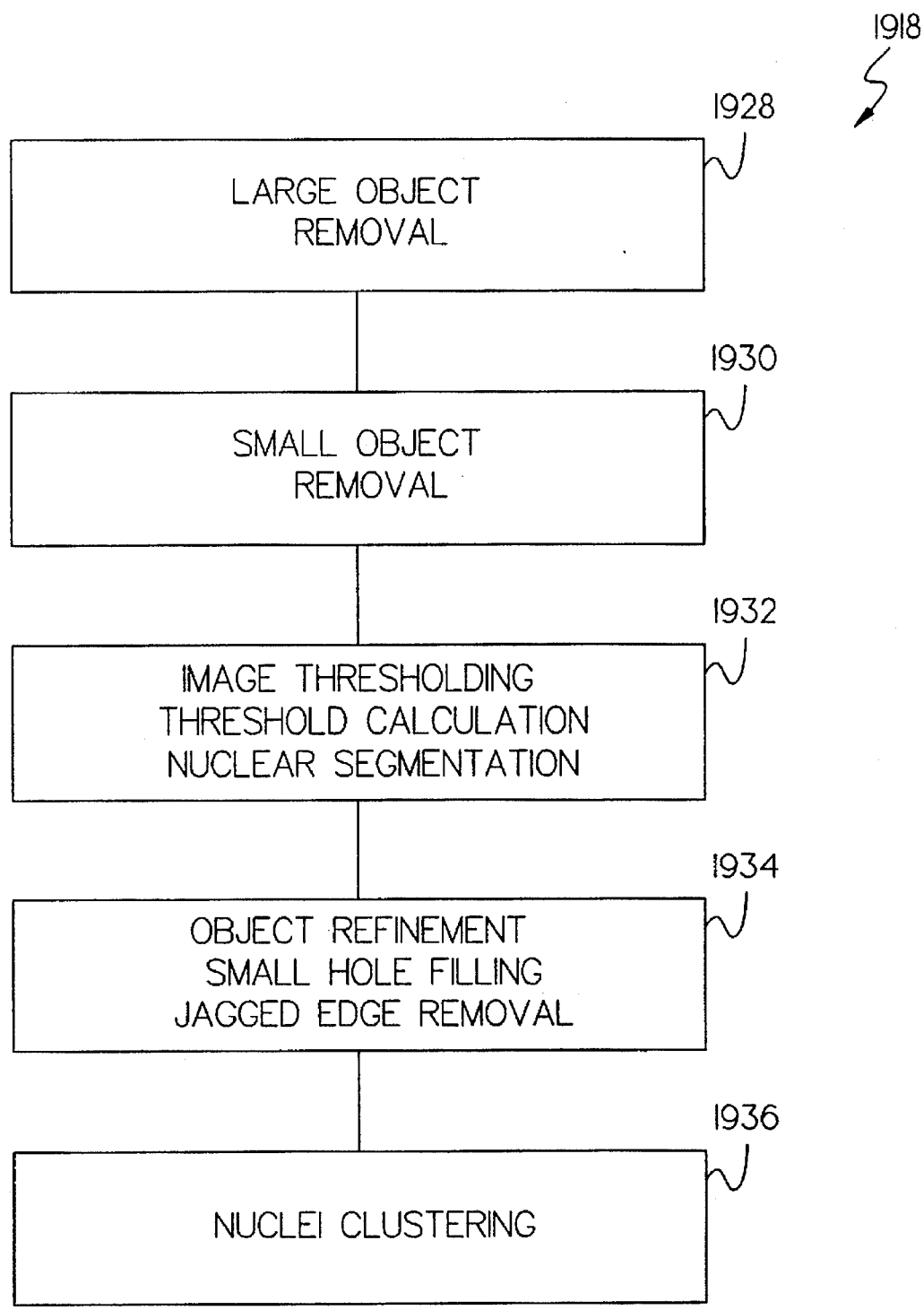
FIG. 24 shows a process flow diagram of a method of the invention to segment each image of biological specimens.

Refer now to FIG. 24 which shows an image segmentation method. The image segmentation step 1918, performs the identification of potential cellular aggregates. It is based on first identifying potential cell nuclei and then determining which nuclei lie close enough to other nuclei to be considered part of a cellular aggregate. In one embodiment, the image segmentation step includes five substeps. Segmentation steps 1928 and 1930 remove background objects, segmentation step 1932 is image thresholding, segmentation step 1934 is object refinement, and segmentation step 1936 is nuclei clustering.

Figure 25:
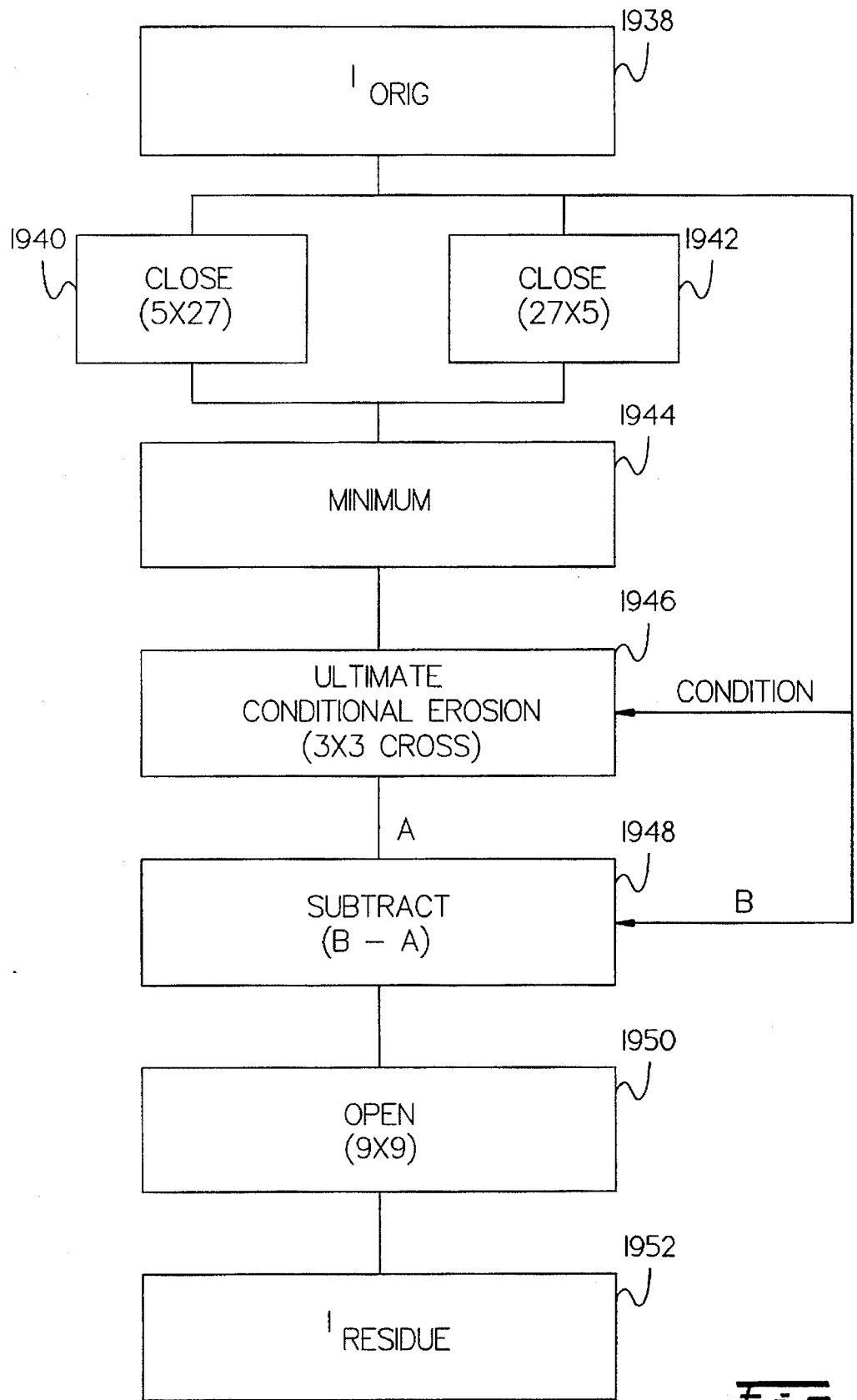
FIG. 25 shows a process flow diagram for background object removal.
Figure 26A:
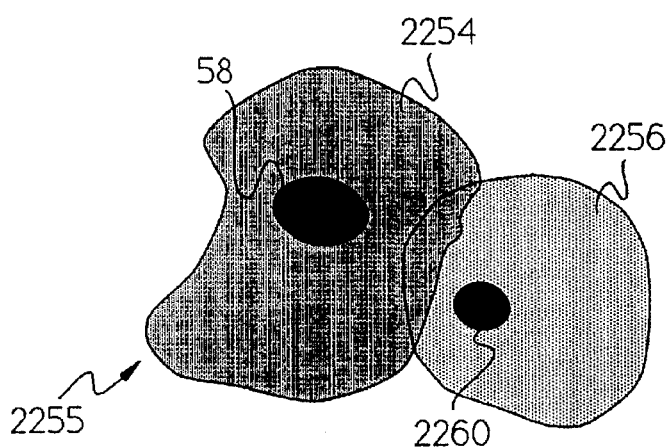
FIGS. 26A, 26B, 26C and 26D show a schematic of a combination of two segmentation masks.
Figure 26B:
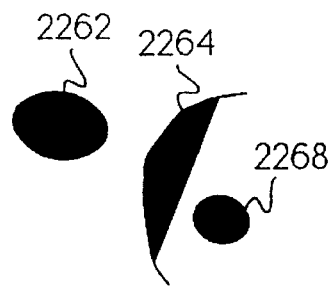
Figure 26C:
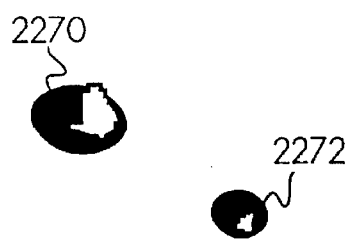
Figure 26D:
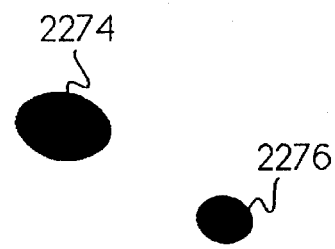

Refer now to FIG. 25 which shows a method for removing large objects from the image. Since nuclei have a finite size range, it is useful to remove objects larger and smaller than that range before image thresholding step 1932. In one embodiment, large objects are removed by closing the image 1938 with a known 27 by 5 flat top structuring element 1940 and with a known 5 by 27 flat top structuring element 1942.

$$I_{Closed} = \min[((I_{orig} \oplus (27 \times 5)) \ominus (27 \times 5)), (((I_{orig} \oplus (5 \times 27)) \ominus (5 \times 27)))]$$

The closed image 1944 is then iteratively eroded conditioned on the original image until no more erosion takes place. This is termed ultimate conditional erosion 1946. The structuring element for the ultimate conditional erosion is a known flat top cross of 3×3 pixels.

$$I_{Erode(0)} = I_{Closed}$$

$$I_{Erode(1)} = \max[I_{Orig}, (I_{Erode(0)} \ominus ((3 \times 3)_{Cross}))]$$

$i = 1$

While $(I_{Erode(i)} \neq I_{Erode(i-1)})$

{

$I_{Erode(i+1)} = \max[I_{Orig}, (I_{Erode(i)} \ominus ((3 \times 3)_{Cross}))]$ $i$ ++

$I_{Erode} = I_{Erode(i)}$

}

In the above equations, a 3×3 cross structure element is a center pixel, two adjacent horizontal pixels, and two adjacent vertical pixels, and where $I_{Erode(i)}$ represents the $i^{th}$ iteration of conditional erosion equation in the while loop above, of the image. The residue 1948 of the conditionally closed, eroded image and the original image contain only objects that are small enough to be nuclei, large objects are removed. The residue image is then opened with a 9 by 9 flat top structuring element 1950 to remove objects smaller than valid nuclei thereby producing a residue image 1952.

To define potential nuclear regions of the image, the gray scale image is thresholded to produce a binary mask in step 1932. In a binary mask, pixels may take on one of two values, active or inactive. Active pixels represent regions where potential nuclei have been identified. In one embodiment, thresholding is done by combining results of two different methods, thereby incorporating the advantages of one to offset the disadvantages of the other. The first method segments the majority of nuclei completely with little problem of over segmentation. In one embodiment, the nuclei identified by the first method is used when the second method confirms that the mask of the first is not a false segmentation shown schematically in FIGS. 26A, 26B, 26C and 26D.

Now refer to FIGS. 26A, 26B, 26C and 26D, which show a graphical example of combination of two segmentation masks to take advantage of the strengths of each. In this embodiment, the first segmentation mask is created by blurring, scaling, and clipping the original image 2255 for use as a threshold image for the image that resulted from step 1928 above. Blurring removes information other than background from the threshold image. Scaling provides appropriate threshold levels. Clipping assures that nuclei have at least a minimum residue strength before they are included in the mask. In one embodiment, the functions are implemented as:

$$I_{Blur} = ((I_{orig}) \ominus (9 \times 9)) \oplus (6 \times 6),$$

$$I_{Scale} = I_{Blur}/2,$$

$$I_{Clip} = \max (I_{Scale}, 10),$$

then the first mask is generated by the following rule:

For each Pixel i

{

If $(I_{iResidue} > I_{iClip})$ then $I_{iFirstMask} = 1$ else $I_{iFirstMask} = 0$,

} where $I_{iResidue}$ is the $i^{th}$ pixel of image $I_{Residue}$ and $I_{iClip}$ is the $i^{th}$ pixel of image $I_{Clip}$. In this embodiment, the second mask is created by conditioning the residue image $I_{Residue}$.

Often nuclei appear overlapped in an image. If a threshold is calculated for all nuclei without regarding overlap, nuclei that overlap will be segmented as one. If the threshold for overlapping objects is adjusted to segment less, the nuclei may segment as separate objects. When objects overlap, their apparent darkness is greater; their residue will be stronger. Therefore, in one embodiment, objects with strong residue are thresholded differently than those with weak residue.

A modified residue image, $I_{ResidueMax}$, containing only monotonically valued objects is created by conditionally dilating the residue image only in areas where pixels are greater than zero so that each object has all pixels equal to the value of the maximum pixel value for the object in the residue image.

$$I_{ResidueMax(0)} = I_{Residue}$$

$i = 1$ while $(i \leq 8)$

{

$I_{Temp} = (I_{ResidueMax(i-1)} \oplus ((3 \times 3)_{Cross}))$

For each Pixel $j$

{

If $(I_{jResidue} > 0)$ then $I_{jResidueMax(i)} = I_{jTemp}$ else $I_{jResidueMax(i)} = 0$

}

$i$ ++

}

An object is considered to have a strong residue if its maximum residue value is greater than StrongObjectTestValue where StrongObjectTestValue =

$$\frac{(\text{ImageBrightness} * 3) + \text{ImageEdgeStrength} - 225}{}$$

$$\text{ImageBrightness} = \frac{1}{N_{Pixels}} \left( \sum_{\text{Pixels}} \text{PixelValue}_i \right)$$

ImageEdgeStrength =

$$\frac{1}{2N_{Pixels}} \left( \sum_{\text{Pixels}} ((I_{Orig} \oplus (3 \times 3)) - I_{Orig}) + \sum_{\text{Pixels}} \text{abs}((I_{Orig} \ominus (3 \times 3)) - I_{Orig}) \right)$$

Where v represents a binomial filter (in the case of a 3×3, it is a convolution operation, for which the kernel weights would be 1/16, 2/16, 1/16 for the top row, 2/16, 4/16, 2/16 for the middle row, and 1/16, 2/16, 1/16 for the bottom row). An image, $I_{StrongObjects}$, is produced by retaining only the strong objects.

For each Pixel i

{

If ($I_{iResidueMax}$ > StrongObjectTestValue)

then $I_{iStrongObjects} = I_{iResidue}$ else $I_{iStrongObjects} = 0$

}

An edge image is created.

$$I_{Edge} = ((((I_{Residue}) \oplus (3 \times 3)) - I_{Residue}) - ((I_{Residue}) \ominus (3 \times 3))) * 2$$

From the edge image, the residue image, and the strong object image a threshold is computed.

$$I_{Thresh} = I_{Edge} + \tfrac{1}{2}(I_{Residue}) + \tfrac{3}{8}(I_{StrongObjects})$$

The mask for the second method is:
For each Pixel i

{

If ($I_{iResidue} > I_{iThresh}$)

then $I_{iSecondMask} = 1$ else $I_{iSecondMask} = 0$

}

The nuclei mask is the conditional dilation of the second mask conditioned on the first mask (the conditional dilation is repeated 4 times to allow the complete dilation of all nuclei).

i = 1 while (i ≤ 4)
{
$I_{Nuclei} = \min[I_{FirstMask}, (I_{SecondMask} \oplus ((3 \times 3)_{Cross}))]$ $I_{SecondMask} = I_{Nuclei}$ i++

}

Figure 27A:
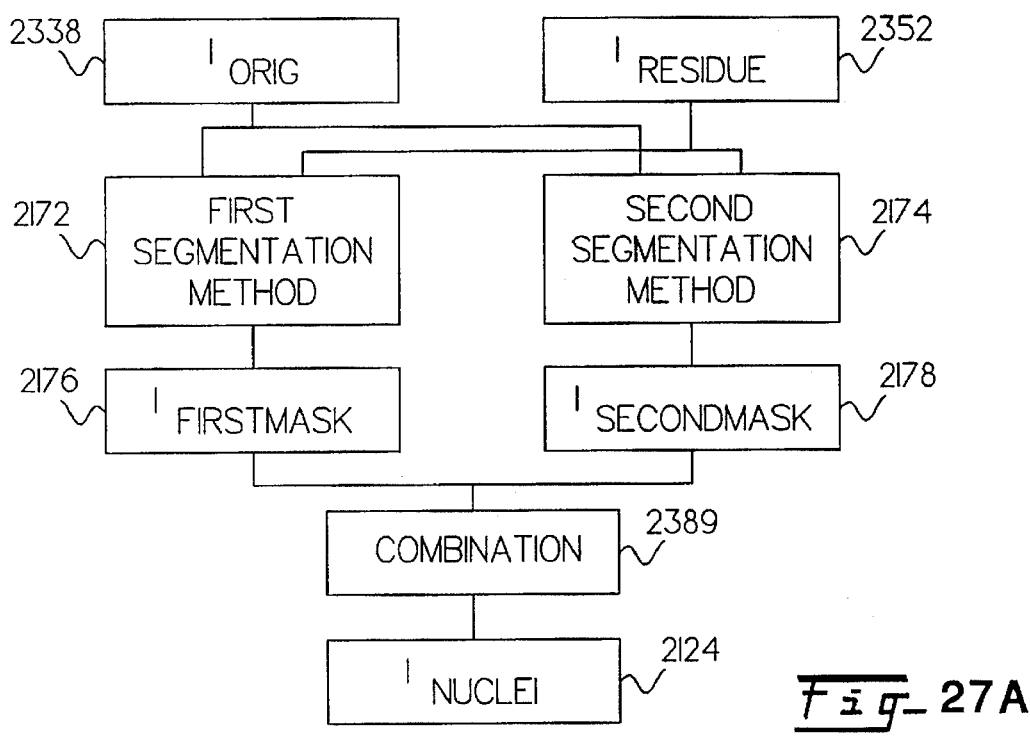
FIGS. 27A, 27B, 27C and 27D (including FIGS. 27E–27F) show process flow diagrams for the nuclear thresholding.

Now refer to FIG. 27A which shows one embodiment of nuclear thresholding as employed in the method of the invention. An original image 2338 and a residue image 2352 are fed to a first segmenter 2172 and a second segmenter 2174. The first segmenter 2172 generates a first mask 2176. The second segmenter 2174 generates a second mask 2178. The combination of the first mask 2176 and the second mask 2178 in combiner 2389 produces a nuclei image 2124.

Figure 27B:
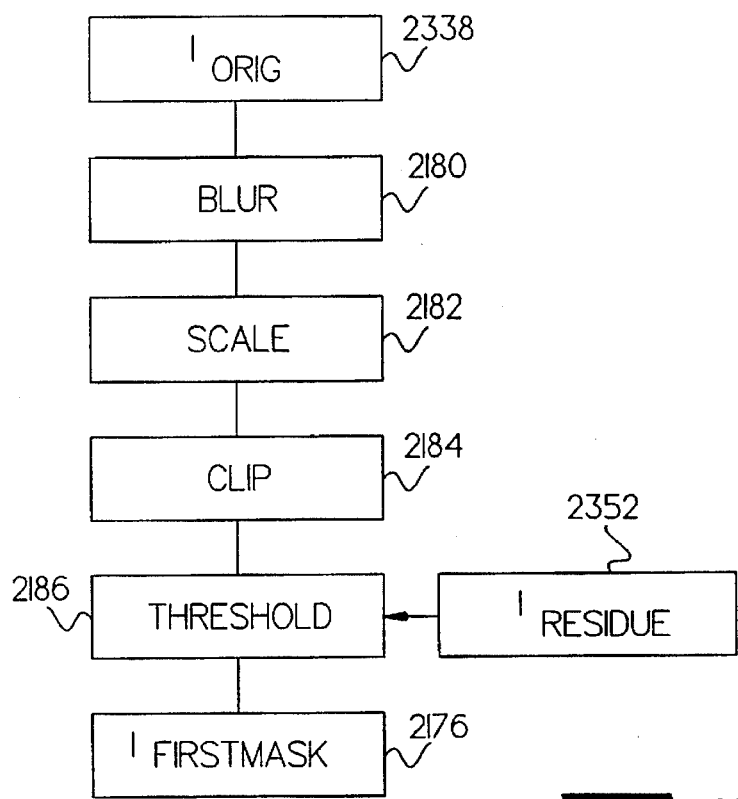

Now refer to FIG. 27B which shows the first segmenter of the invention. The original image 2338 is fed to be blurred in 2180. The image is then scaled in 2182. The image is then clipped in 2184. The residue image 2352 is then thresholded with the clipped image in 2186 to generate a first mask 2176.

Figure 27C:
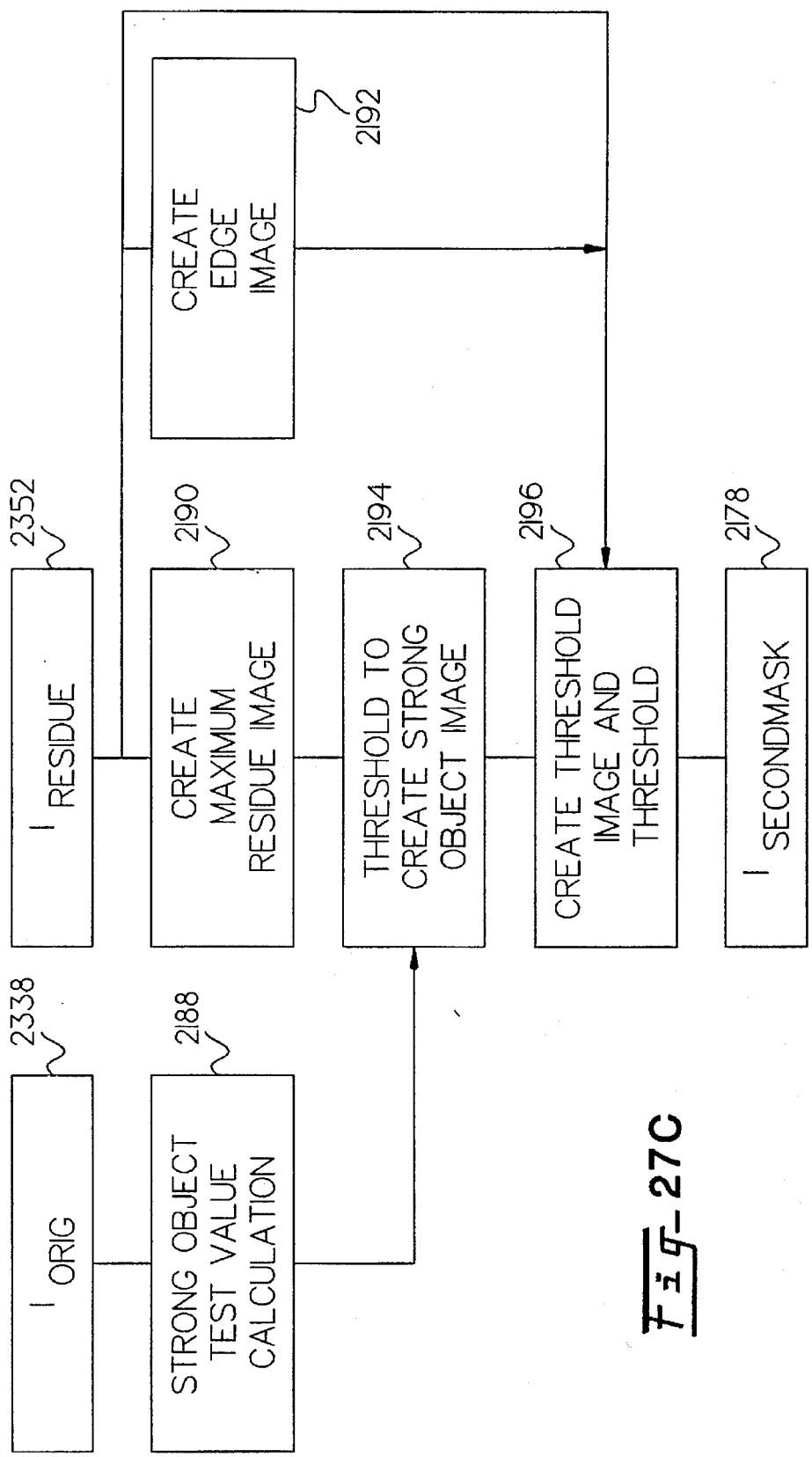

Now refer to FIG. 27C which shows the creation of the second mask 2178. The original image 2338 is fed to test the strong object value calculator 2188. The residue image is fed to create a maximum residue image 2190 and an edge image 2192. A strong object image is created by thresholding 2194. The second mask 2178 is created by taking the residue image 2352, and thresholding with the threshold images, generated from the strong object image 2194 and the edge image 2192.

Figure 27F:
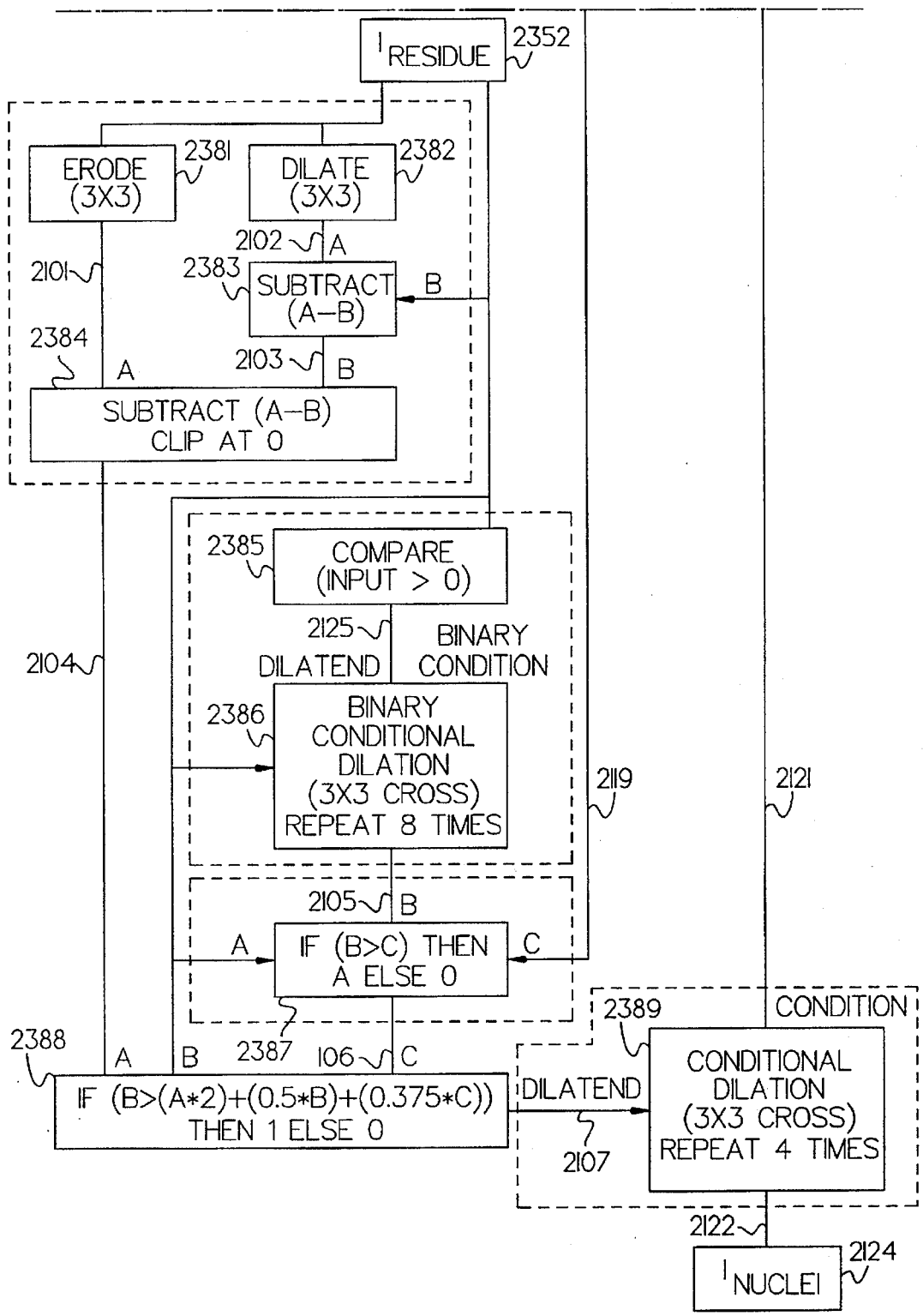

Now refer to FIGS. 27D–27F which show the processing flow for an embodiment of nuclear thresholding to find a nuclei image from an original image, where a residue image has already been created from the original image. The cytological image processing method starts with the step of obtaining a digital representation of the cytological image 2338. The invention then does a 3×3 erosion 2381 of the residue image 2352 to provide a first representation 2101. A 3×3 dilation 2382 of the residue image 2352 provides a second representation 2102. Subtracting 2383 the residue image 2352 from the second representation 2102 provides a third representation 2103. Subtracting 2384 the third representation 2103 from the first representation 2101 and setting all negative values to zero provides a fourth representation 2104. The invention then compares the residue image 2352 to zero to provide a binary condition control signal 2125. The invention then repeats a binary conditional dilation 2386 with a 3×3 cross, eight times to provide a fifth representation 2105. The residue image 2352 is transferred to a sixth representation 2106 if the fifth representation 2105 is greater than a nineteenth representation 2119. The invention then morphologically computes 2388 a binary result to a seventh representation 2107, the binary result being one if the residue image 2352 is greater than a predetermined combination of the fourth representation 2104, the residue image 2352 and the sixth representation 2106, zero otherwise. In one embodiment, if the residue image 2352 is greater than two times the fourth representation 2104 plus 0.5 times the residue image 2352 plus 0.375 times the sixth representation 2106, then the seventh representation 2107 is set to a one, zero otherwise. A 3×3 blurring 2391 of the original image 2338 provides an eighth representation 2108. A 3×3 dilation 2392 of the original image 2338 provides a ninth representation 2109. A 9×9 erosion 2394 of the original image 2338 provides a tenth representation 2110. The invention then subtracts the original image 2338 from the eighth representation 2108 to provide an eleventh representation 2111. Subtraction 2395 of the original image 2338 from the ninth representation 2109 provides a twelfth representation 2112. Dilation 2397 of the tenth representation 2110 provides a thirteenth representation 2113. Conversion of negative pixels to positive pixels of the same magnitude 2398 for the eleventh representation 2111 gives the fifteenth representation 2115. Computation of the pixel average 2399 of the twelfth representation 2112 provides a fourteenth representation 2114. Computation of the pixel average 2379 of the fifteenth representation 2115 provides a seventeenth representation 2117. Computation of the pixel average 2378 of the original image 2338 provides an eighteenth representation 2118. Shifting 2100 of the thirteenth representation 2113 right one bit provides a sixteenth representation 2116. Computation of the sum 2377 of the fourteenth representation 2114, seventeenth representation 2117, three times the eighteenth representation 2118 and subtracting 255 provides the nineteenth representation 2119. Taking the maximum 2375 of the sixteenth representation 2116 and the value 10 provides a twentieth representation 2120. Comparison 2390 of the residue image 2352 to the twentieth representation 2120 provides a twenty-first representation 2121. Conditional dilation 2389 of the seventh representation 2107 and twenty-first representation 2121 provides the nuclei image 2124.

Figure 28:
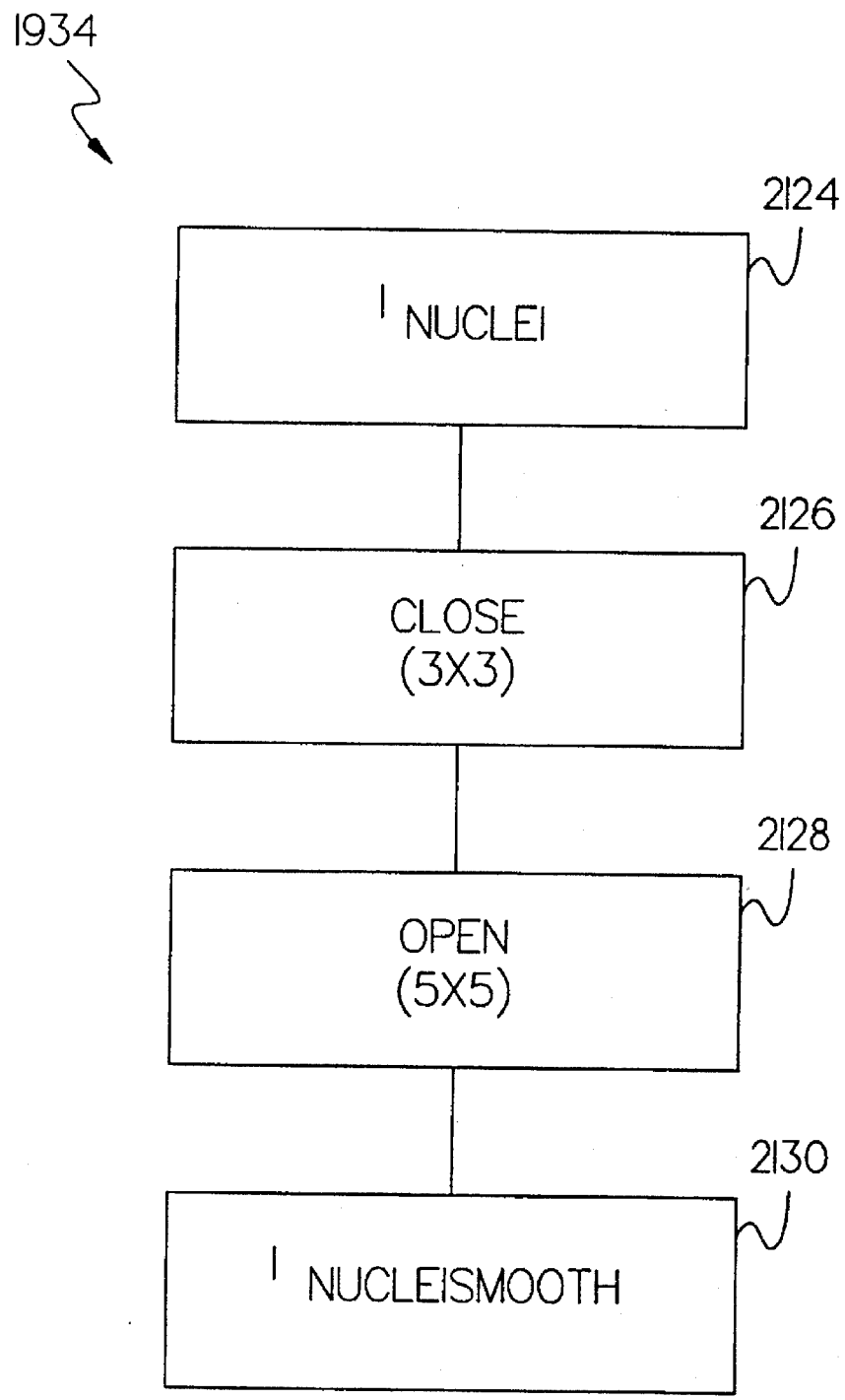
FIG. 28 shows a process flow diagram for object refinement.

Object refinement is conducted in step 1934, FIG. 24. FIG. 28 shows the object refinement step 1934 in more detail. Small holes may be filled in segmentation by closing with a 3×3 structuring element 2126. The segmentation mask may then be smoothed by opening with a 5×5 structuring element 2128. Note that the nuclei image is updated upon completion of the smoothing operation, creating the smooth nuclei image 2130.

$$I_{NucleiNoHoles} = (((I_{Nuclei} \oplus (3 \times 3)) \ominus (3 \times 3))),$$

$$I_{Nuclei} = I_{NucleiSmooth} = (((I_{NucleiNoHoles} \ominus (5 \times 5)) \oplus (5 \times 5)))$$

Figure 29:
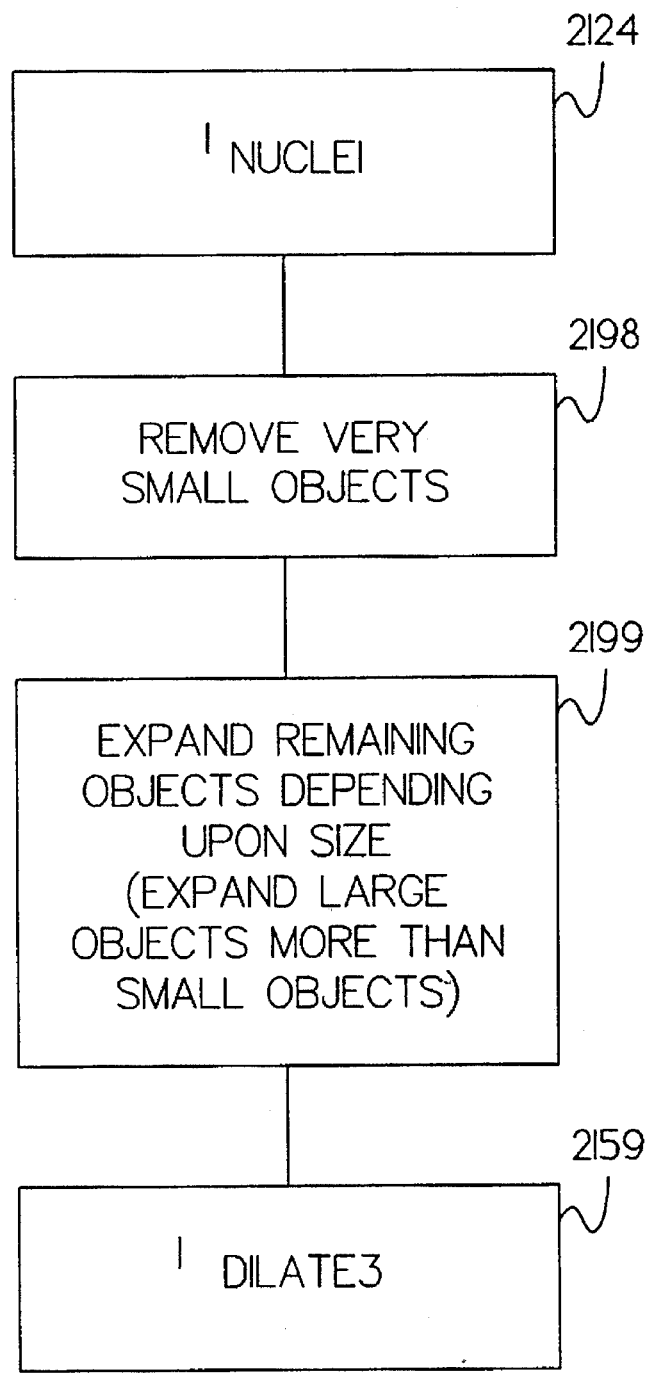
FIGS. 29 and 30 show process flow diagrams for nuclei clustering.

Now refer to FIG. 29 which shows the segmentation step for nuclei clustering. A nuclei image 2124 has very small objects removed at 2198. Remaining objects are expanded depending upon their size where large objects are expanded more than small objects 2199. A dilated image 2159 is generated.

Figure 30:
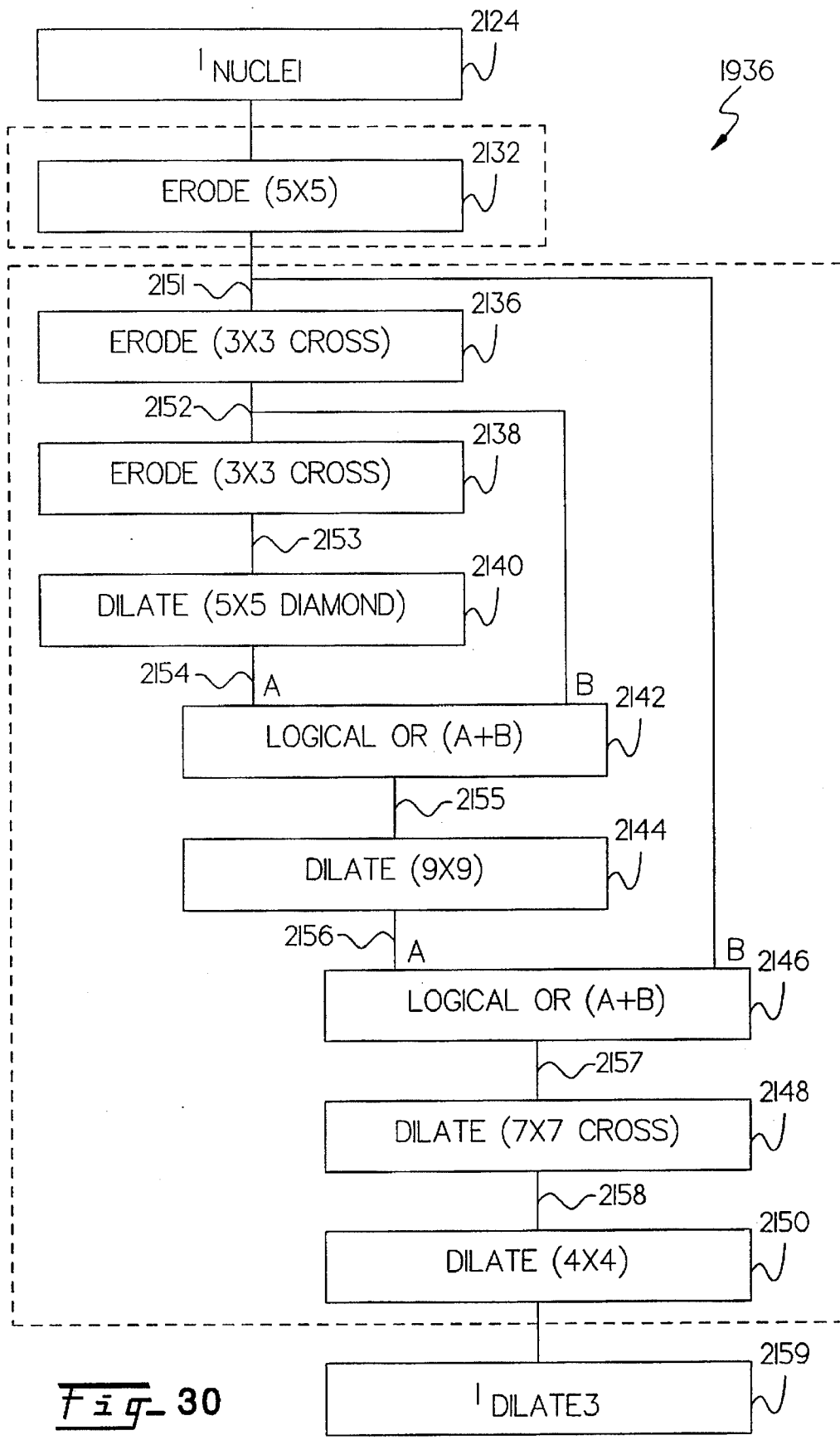

Now refer to FIG. 30 which shows processing flow for nuclei clustering. In one embodiment, clustering 1936 (FIG. 24) is nuclear size dependent. Small nuclei must be close to be considered part of an aggregate, while larger nuclei are not so restricted. Larger nuclei may be more distant and still considered part of an aggregate. Clustering is accomplished by dilating nuclei dependent on size. Size dependent dilation is accomplished by creating nuclei masks for nuclei of different sizes, then dilating each according to size range and "OR"ing the masks to give a final cluster mask.

$$I_{Size1} = (I_{Nuclei} \ominus (5 \times 5))$$

$$I_{Size2} = (I_{Size1} \ominus ((3 \times 3)_{Cross}))$$

$$I_{Size3} = (I_{Size2} \ominus ((3 \times)_{Cross}))$$

$$I_{Dilate1} = (I_{Size3} \oplus ((5 \times 5)_{Diamond})) + I_{Size2}$$

$$I_{Dilate2} = (I_{Dilate1} \oplus (9 \times 9)) + I_{Size1}$$

$$I_{Dilate3} = (I_{Dilate2} \oplus ((7 \times 7)_{Diamond})) \oplus (4 \times 4)$$

where a 5×5 Diamond structuring element is:

$$\begin{vmatrix} 0 & 0 & 1 & 0 & 0 \\ 0 & 1 & 1 & 1 & 0 \\ 1 & 1 & 1 & 1 & 1 \\ 0 & 1 & 1 & 1 & 0 \\ 0 & 0 & 1 & 0 & 0 \end{vmatrix}$$

and a 7×7 Diamond is the 5×5 Diamond dilated by a 3×3 Cross. The invention takes the nuclei image 2124 and does a 5×5 erosion 2132 of the nuclei image 2124 to provide a first cluster representation 2151. A 3×3 cross erosion 2136 of the first cluster representation 2151 provides a second cluster representation 2152. A 3×3 cross erosion 2138 of the second cluster representation 2152 provides a third cluster representation 2153. A 5×5 diamond dilation 2140 of the third cluster representation 2153 provides a fourth cluster representation 2154. The logical ORing 2142 of the second cluster representation 2152 and fourth cluster representation 2154 provides a fifth cluster representation 2155. Dilating 2144 the fifth cluster representation provides a sixth cluster representation 2156. Logical ORing 2146 the first cluster representation 2151 and sixth cluster representation 2156 provides a seventh cluster representation 2157. A 7×7 cross dilation 2148 of the seventh cluster representation 2157 provides an eighth cluster representation 2158. A 4×4 dilation 2150 of the eighth cluster representation 2158 provides the segmented image 2159.

In one embodiment, if objects in the segmented image 2159 ($I_{Dilate3}$) are larger than 2400 pixels, the object is considered to be a potential cellular aggregate. Other objects are removed from consideration.

Feature extraction 1920, is the measurement of features related to the segmented potential cellular aggregates. In one embodiment, the ratio of the standard deviation of the pixel values of the nuclei to the standard deviation of the pixel values of the cluster are measured. Also, the standard deviation of the nuclear compactness is measured. Where the nuclear compactness is defined as $$NuclearCompactness = (Perimeter^2)/Area$$

With feature values available the object classification 1922 step may be performed. In one embodiment, an object is classified as probable squamous artifact if:

$$(StdNuclei/StdCluster) + (StdNucCompact * 0.038) > 1.14.$$

APPARATUS FOR AUTOMATED IDENTIFICATION OF THICK CELL GROUPINGS ON A BIOLOGICAL SPECIMEN, U.S. patent application Ser. No. 08/309,116

Figure 32:
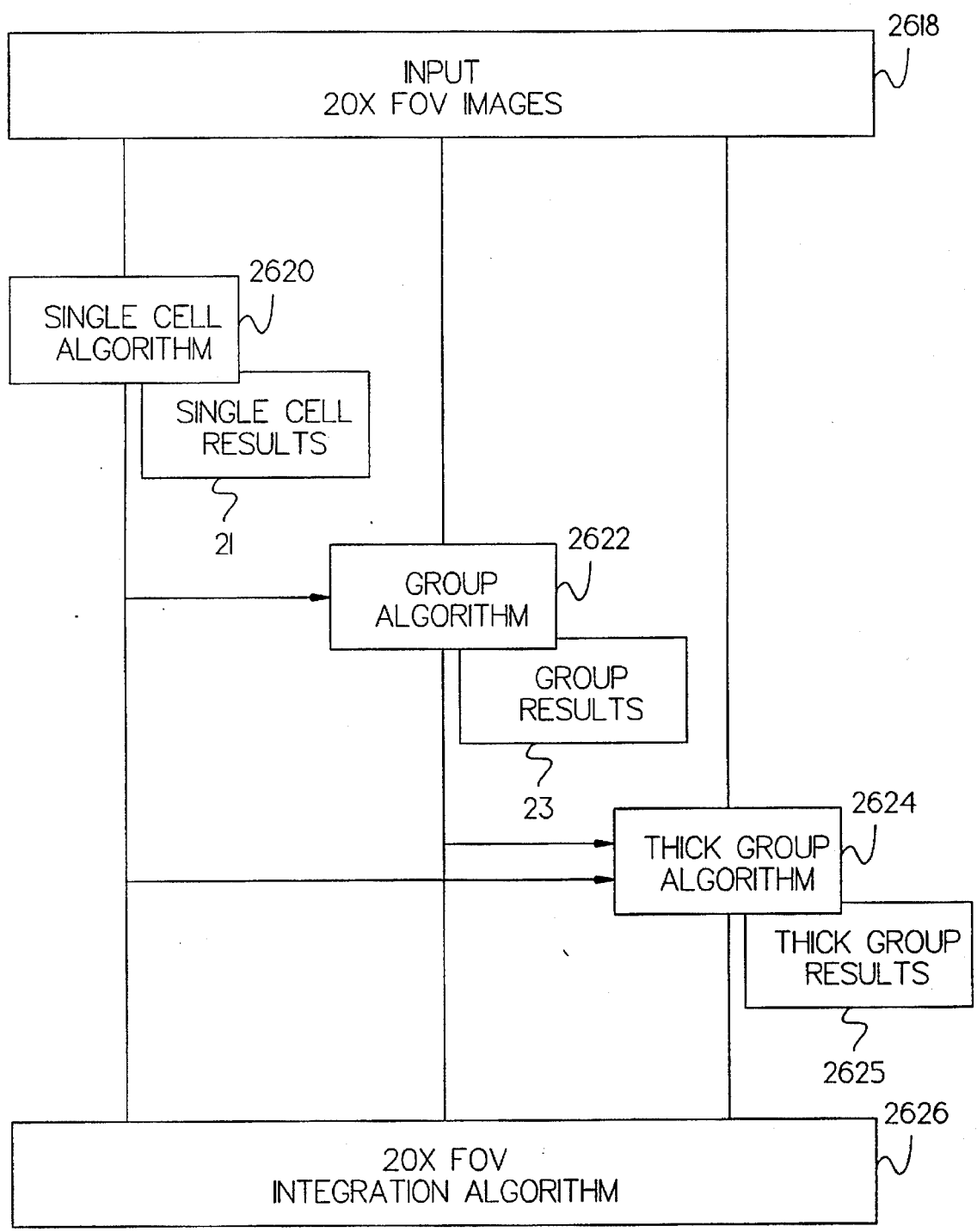
FIG. 32 shows a process flow diagram to process single cell, group, and thick group analysis.

During thick group analysis the computer system 540 receives input from three sources, as illustrated in FIG. 32.

20× FOV input images 2618

Results 2621 from a single cell analysis 2620

Results 2625 from the group analysis 2624

Images at 20× magnification from the image acquisition module are processed by the processor 540. These are images the computer has analyzed at 4× magnification and have been determined to have a likelihood of containing clusters of cells. These cells may be normal or potentially abnormal cells that tend to occur in thick groups. The invention is trained to recognize grouped cells that are so densely clustered that their nuclei are difficult to differentiate. Cells that tend to occur in such thick groups include normal and abnormal cells of the endocervix and endometrium. For a complete list of the object types that were used for training, see Table 1 below.

The method classifies each of its segmented objects as either abnormal, which are potentially abnormal thick groups, or other, which are cellular artifacts, non-cellular artifacts or normal cell groups. Classification results from multiple analysis at 20× magnification are accumulated and used for slide classification. The thick group process also receives whole image features from both the single cell analysis and endocervical group analysis to assist thick group classification.

The following table shows objects used for training of the classifier of thick groups. Objects identified with an (A) were trained to be classified as abnormal whereas objects denoted with an (O) were classified as other objects and disregarded.

TABLE 1

| cellular objects | artifact objects |
| --- | --- |
| (O) normal endometrial | (O) mucus |
| (A) atypical endometrial hyperplasia | (O) bacteria |
| (A) endometrial adenocarcinoma | (O) fibrous material |
| (O) normal endocervical | (O) bubble edge |
| (A) AGUS | (O) slide edge |
| (A) atypical endocervical | (O) ground glass |
| (A) adenocarcinoma endocervical | (O) graphite |
| (A) repair/reactive endocervical | (O) not under coverslip |
| (O) squamous cell groups | (O) out of focus |
| (A) herpes | (O) other |
| (A) adenocarcinoma in situ, endocx | (O) inside bubble |
| (A) carcinoma in situ, squamous | |
| (O) parabasal/metaplastic | |
| (O) cytoplasm only | |
| (A) adenocarcinoma | |
| (A) high grade SIL | |
| (O) lymphocytes | |
| (O) polys | |
| (O) red blood cells | |
| (O) histiocytes | |
| (O) corn flaking | |

(A) = abnormal
(O) = Other

Figure 31:
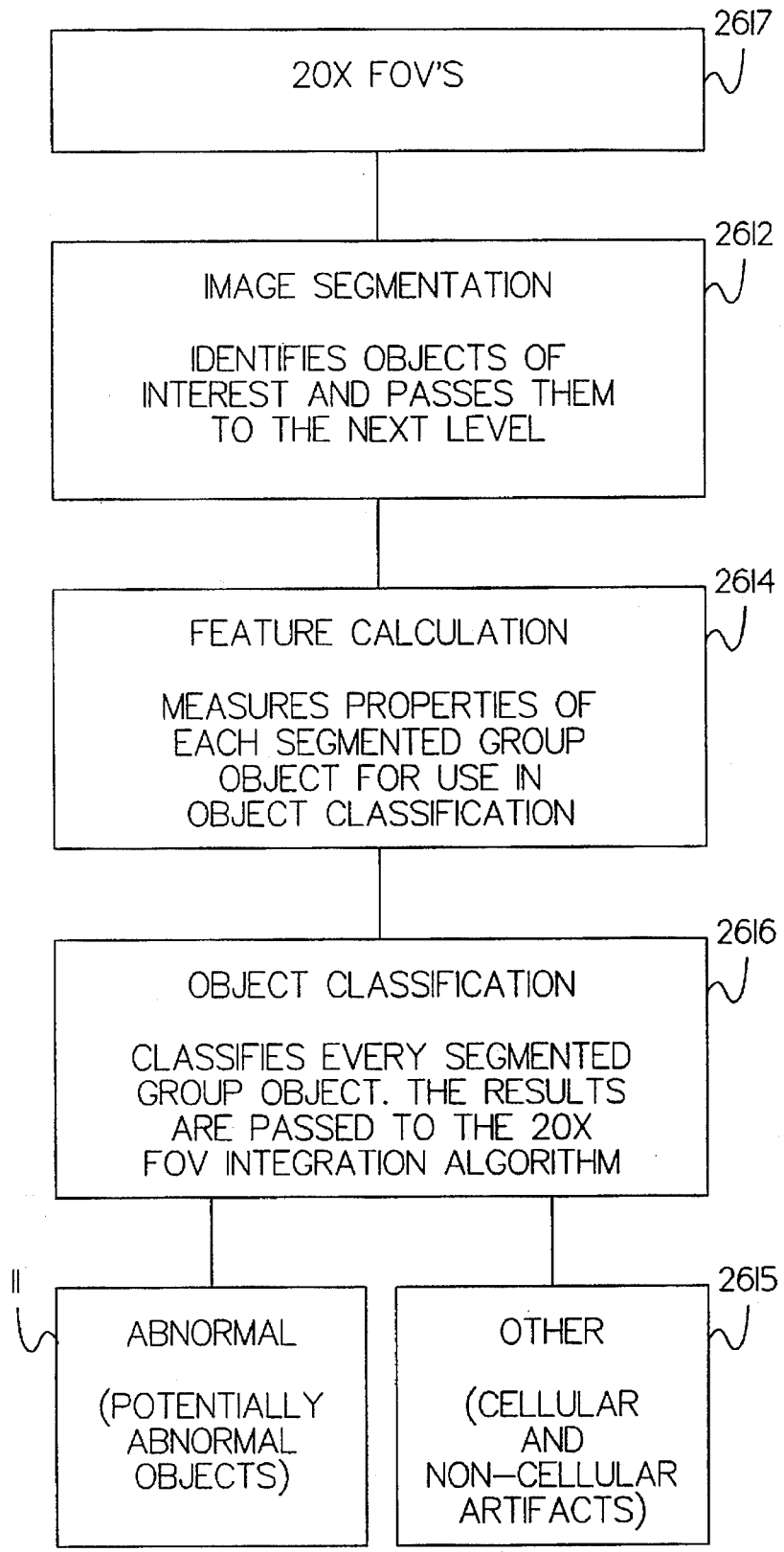
FIG. 31 shows a process flow diagram to process thick groups of cells.

Now refer to FIG. 31 which shows the thick group processing of the invention. An image of the biological specimen and whole image features are obtained 2617. The 20× magnification images are received from the image capture and focus system 516, which may be controlled by computer 562; some whole image features are received from the single cell analysis and group analysis.

The invention utilizes the following features from group classification. The magnitude of 2×1 dark edge in an FOV (feature #98).

These features are derived from single cell classification:
High mean (thick group feature #93), and
Low threshold (thick group feature #95).

The classification results of thick group analysis are:
number of objects segmented,
number of objects eliminated by box filters,
number of objects eliminated by classification stages 1, 2 and 3,
number of potentially abnormal objects remaining after the stage 3 classifier, and
5-bin confidence histogram of remaining, potentially abnormal objects.

Additionally, the method performs error checking that does the following:
Checks for proper return code from the classifiers, and
Performs a checksum on the number of objects classified.

If an error is detected, the code aborts with an error message.

Prior to the thick group analysis the computer system does the following:
Detects coverslip edges and excludes from image processing all areas that are outside of the area bounded by coverslip edges.
Accumulates slide level results from all 20× FOVs processed for thick groups for each slide.
Provides the scores to the user interface.
Controls image acquisition and assures that images passed for thick group analysis conform to image quality specifications. The method checks that images are acquired based on predetermined rules.
Handles errors if they are identified during thick group processing.

The thick group processing method identifies certain kinds of potentially abnormal cells that tend to occur in thick groups. These thick groups are collections of cells that are so densely clustered that it is difficult to distinguish individual nuclei. There are three major steps in processing:
Image Segmentation 2612,
Feature Calculation 2614, and
Object Classification 2616.

Figure 33:
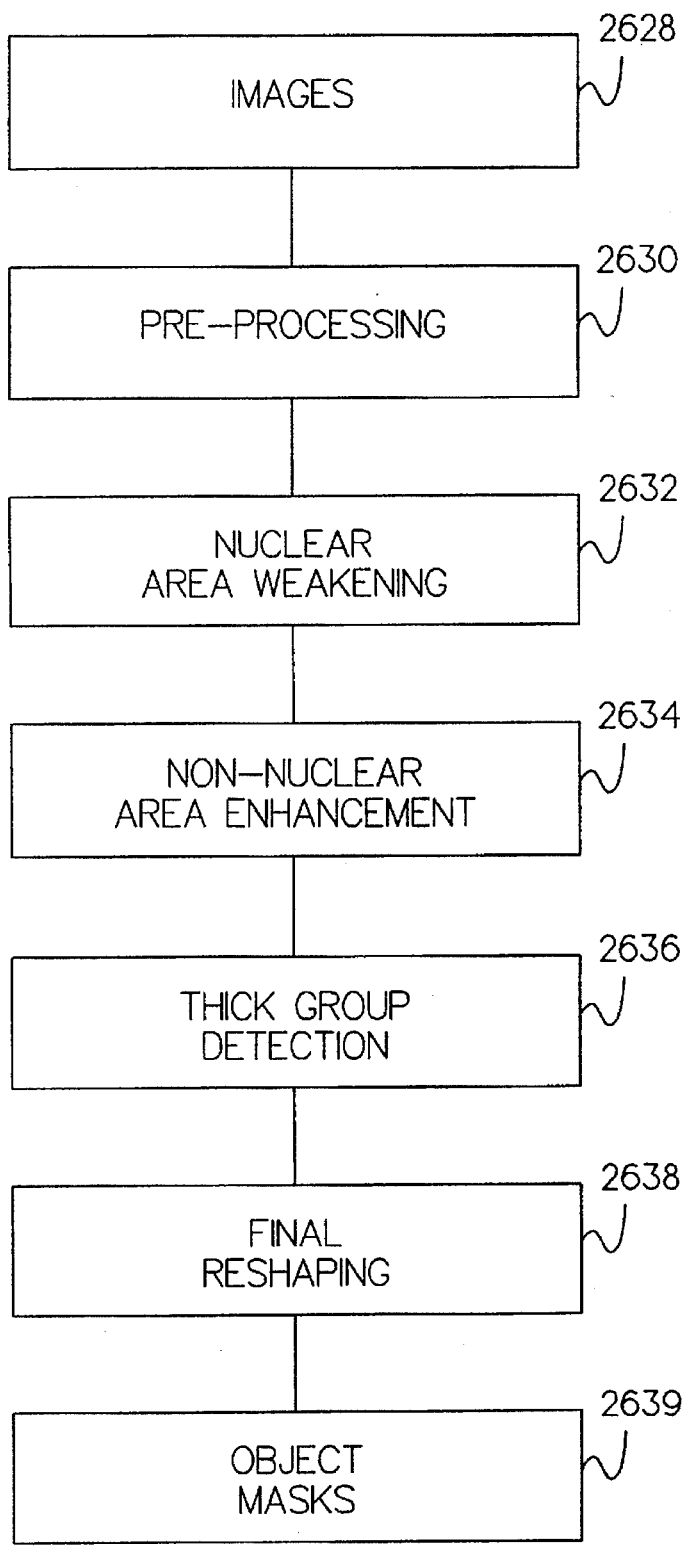
FIG. 33 shows a process flow diagram of a method for performing image segmentation.

Image segmentation 2612 is the process of identifying objects of interest within a gray scale image and creating an object mask. An object mask is a binary image that represents the objects. Each area of interest is represented as active pixels in the object mask. Image segmentation, one example of which is illustrated in more detail in FIG. 33, is a multiple step process.

The pre-processing stage 2630 eliminates single cells and detects nuclear grouping information. This information is used to integrate groups of cells into clusters. The information integration process uses the following image processing sequence:

| Operation | Input image location | Output image location | Structure element and size |
| --- | --- | --- | --- |
| Dilate | 1L | 1H | rod 7 × 1 |
| Erode | 1L | 1H | rod 9 × 1 |
| Dilate | 1H | 1H | rod 11 × 1 |
| Erode | 1H | 1H | rod 13 × 1 |
| Dilate | 1H | 1H | rod 15 × 1 |
| Erode | 1H | 1H | rod 17 × 1 |

Objects are subjected to a sequence of dilations and erosions. In each dilation and erosion operation, the structuring element is increased in size. This removes local, within cell, variations and isolates and highlights global, or inter-cell grouping information.

The nuclear area weakening stage 2632 detects the nuclear area by taking the image created during the pre-processing step then subtracting the original image from it. The detected nuclear area is added to the pre-processing image to remove isolated nuclei. This operation finds thick cell group areas in which individual nuclei cannot be delineated; it then derives object masks from these areas.

Non-nuclear area enhancement 2634 is designed to improve connectivity of the clusters. A sequence of morphological operations detects non-nuclear areas that are in close proximity to nuclei. Next, the non-nuclear area is subtracted from the weakened nuclear area image. The subtraction operation enhances the possibility of inclusion of these non-nuclear areas.

During thick group detection 2636, a two-state conditional thresholding process detects areas containing potential thick groups of cells. First a "less than" threshold is applied to the enhanced image to detect seed regions. Seed regions roughly define the shape of the thick group mask. Seed regions are dilated by a disk with a radius of 13 pixels. As this "less than" threshold value is increased, more pixels are detected. A higher threshold is applied to detect all potential thick group regions. These images are combined by finding pixels that are common to both the higher threshold and dilated images.

Opening, which is a simple binary morphological operation, reshapes objects to smooth boundaries and remove small regions in step 2638. A disk with a radius of 13 pixels is used as the structuring element for the opening. The result of opening is the final result of image segmentation, which creates thick group object masks 2639.

Refer again to FIG. 31, features are calculated according to a pre-established protocol in step 2614. Features are computed based either on portions of an image as defined by an object mask, or based on the whole image. Object based features are numerical values that correspond to some aspects of a thick group's presentation. For example, area is a feature that gives the size, in pixels, of a thick group of cells; fov_brightness is a whole image feature that provides information about the average brightness of an entire 20× FOV. Object Classification 2616 is accomplished using sets of features in a linear combination, then thresholding the result. A series of these combinations is integrated in a tree structure that together form a Fisher's linear binary decision tree classifier. Several classifiers are used in series to form the overall algorithm. One goal is for early classifiers to eliminate the majority of objects that are thick groups of cells of normal cells or artifacts that resemble thick groups of cells. The method classifies these groups of objects as "other". Objects that remain are more likely to be classified as potentially abnormal.

The method eliminates about 99% of artifact or normal cellular thick groups of cells, while retaining about 33% of potentially abnormal thick groups of cells.

Many types of abnormal cellular conditions tend to form in thick groups of cells. During training, the thick group method is designed to identify the following cell group types as potentially abnormal: adenocarcinoma and atypia of the endocervix and endometrium, general adenocarcinoma, adenocarcinoma in situ, atypical glandular cell of unidentified significance (AGUS), repair and reactive states of endocervical cells, herpes, and high-grade squamous intraepithelial lesions. All these cell types tend to appear in thick groups.

Figure 34:
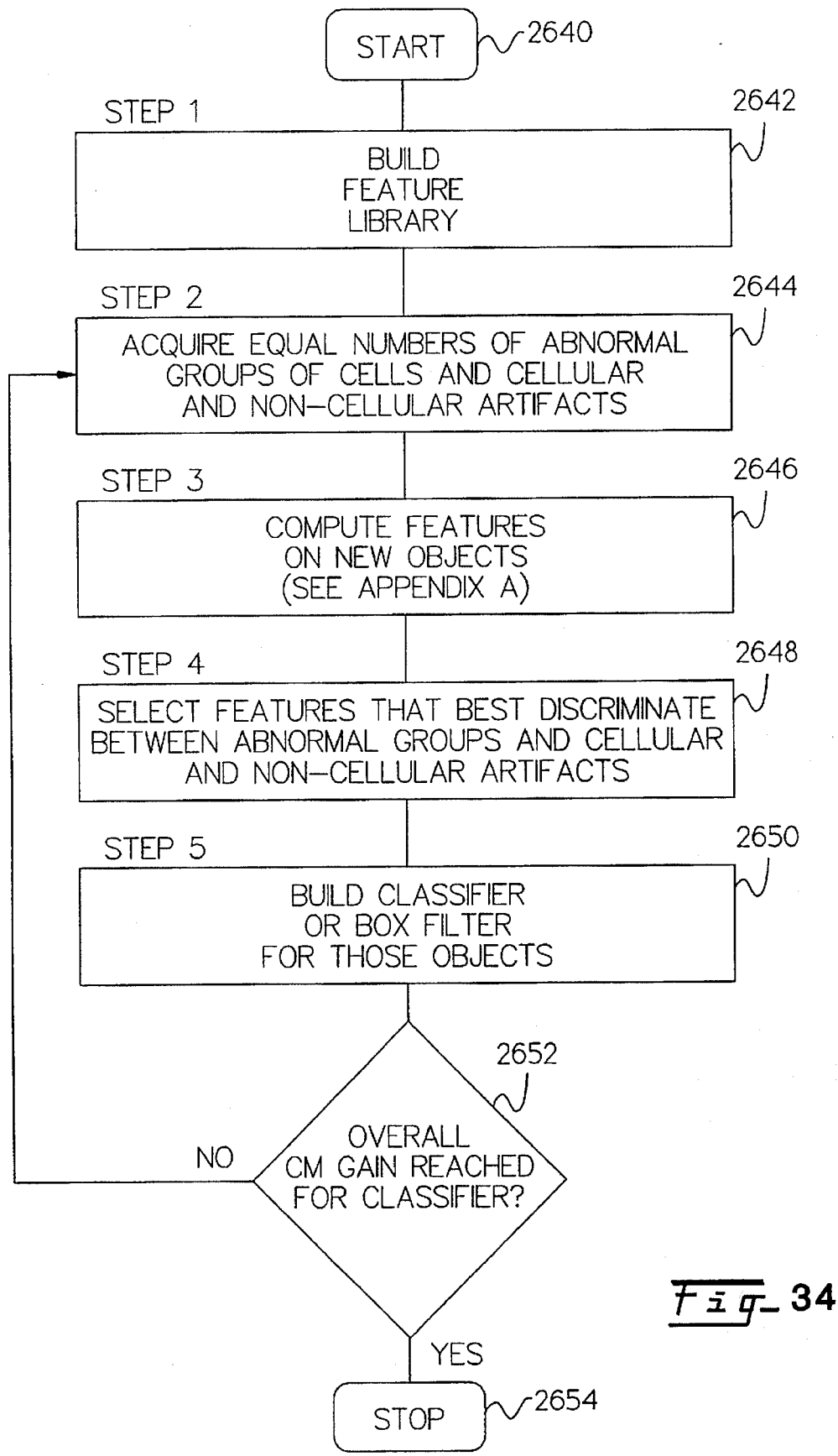
FIG. 34 shows a process flow diagram of a training method.

There are five major steps in invention training, as shown in FIG. 34. Step 2642 is to build a library of features that can be used to separate potentially abnormal objects from objects that are artifacts or normal cells. Step 2644 acquires objects used to train a ,given stage of processing. Step 2646 computes features identified in the feature library on new objects. Step 2649 selects those features in the feature library that most effectively separate objects in the training set. Step 2650 builds a given stage of classifier based on the selected features. Steps 2644 through 2650 may be repeated several times. Feature identification, object acquisition, feature selection, and object classification are described herein.

Thick group processing classifies as potentially abnormal those abnormal conditions listed inn Table 1. In general, the method discards normal cellular groups.

The method uses features that are compatible with endocervical group analysis. However, the thick group method uses only those features that do not involve nuclear segmentation.

A wide range of features is necessary to properly discriminate segmented groups. Features used can be categorized in two different ways:
They can be identified by the kind of information they measure—object shape, size, and texture, and so forth.
They can be identified by what part of an image they measure—the object of interest, a small area around the object, or the whole image.

For algorithm training, about equal numbers of normal or artifact groups, "other", and abnormal groups were acquired. The abnormal classification includes all objects that are groups of potentially abnormal cells configured in thick groups. The other classification includes artifacts and groups of normal cells. See Table 1 for identification of the abnormalities and other conditions used for training.

To manually acquire objects, a cytotechnologist screens abnormal slides and circles areas containing abnormal thick groups. These slides are then placed in the apparatus of the invention, and the abnormal thick group is positioned underneath the objective lens. The video cameras capture an image at 20×. Later, a cytopathologist verifies the diagnosis of the group. Once verified, these images become a part of the manual cell library that contains a number of images of conditions.

Other normal cell thick groups and all artifact groups were obtained by implementing the classifier as a prototype machine running with normal slides. That process yielded a set of objects that passed. the classifier at a given stage in its development. At the beginning of machine development, only the segmenter was implemented in code. The slides were processed and fields of view were saved in which at least one thick group was segmented. These field of views were reviewed by a cytotechnologist and placed in one of the object categories listed in Table 1.

Based on this data, a given stage in the classification process was built and coded. As indicated by FIG. 34, the process is again repeated, except now only those objects that pass the most recent classifier were used to train the next stage.

Once a training set has been constructed for a given stage, it is necessary to select the features that are best able to discriminate between object classes. Feature sets may be determined using SAS' stepwise discriminant analysis. The measure used to select features was Wilkes' lambda. A definition for this measure and the underlying theory governing the discriminant process is given in the SAS/STAT User's Guide, Volume 2, pp 1493-1509.

Step 2644 of FIG. 34 describes the process of constructing a data set that is used to train a classifier. Each object is given a label as shown in Table 1. The task of the classifier is to establish decision boundaries so that the assigned classification most often matches the abnormal or other label given in Table 1. Selected features are used in a linear combination and thresholded. As will be appreciated by those skilled in the art, when several such combinations are combined in a binary tree structure, they form a Fisher's linear binary decision tree classifier. For a more detailed account of the Fisher's linear decision tree and the process used to build them, refer to the paper "A Binary Decision Tree Classifier" by Joo and Haralick in Machine Vision International, Feb. 19, 1986.

In addition to Fisher's linear decision trees, the thick group method uses box filters. These filters are implemented in the form:

$$0 \geq a0*(feature2) + a1 - feature1$$
where a0, a1 = constants
feature 1, feature 2 = feature values If the expression is true, the object is classed as an artifact and stops further classification.

Box filters are trained on abnormal cell populations and specific artifact types because a significant portion of the artifact feature distribution does not overlap with the abnormal distribution, even in two-dimensional space. Therefore, box filters may be used to eliminate a substantial portion of artifacts at a small expense in both processing time and loss of potentially abnormal objects.

Figure 35:
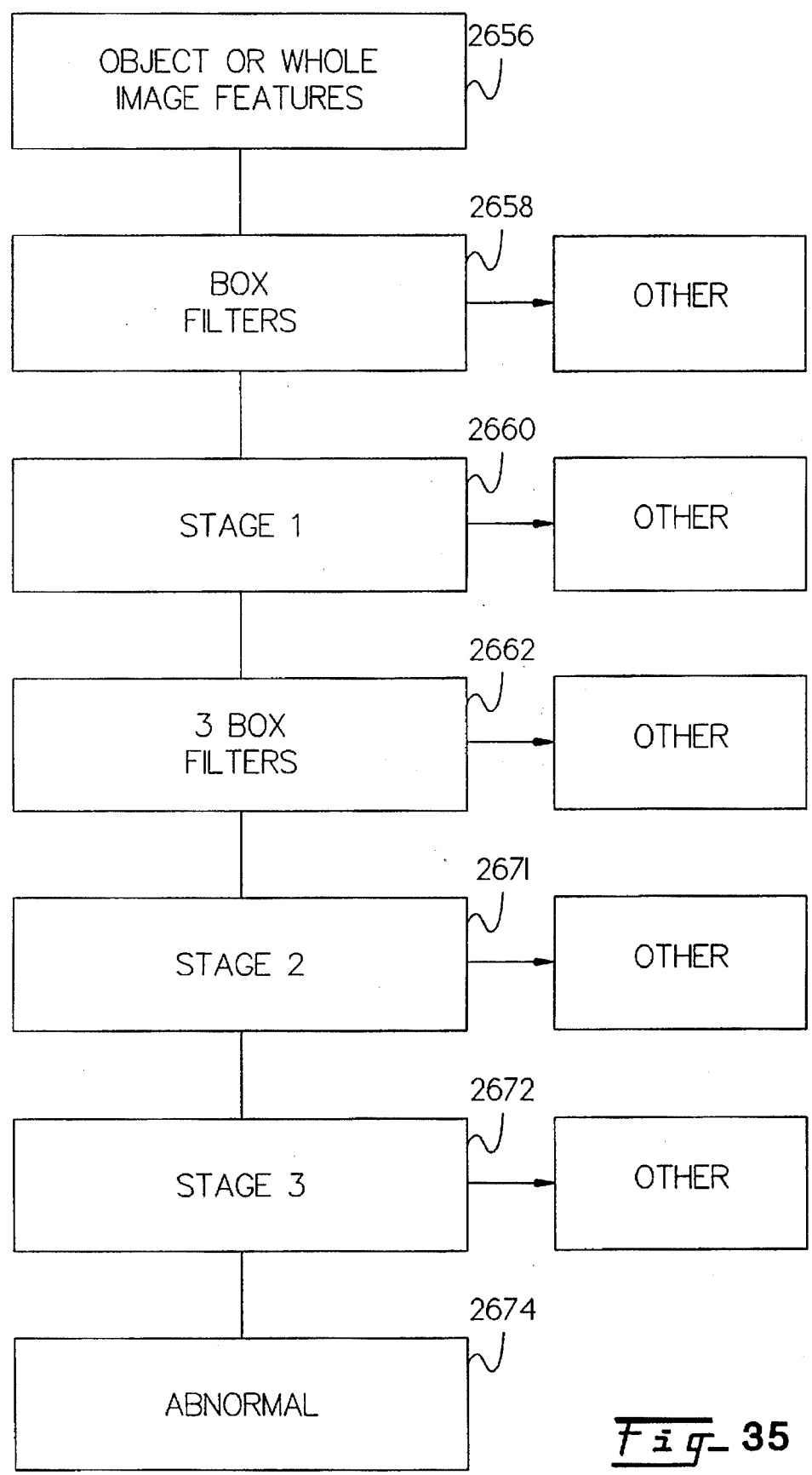
FIG. 35 shows a process flow diagram of an object classification method.

FIG. 35 shows a flowchart of the thick group analysis method. The graphic shows that the first step 2658 is a series of box filters intended to reject obvious artifact groups. Next, three Fisher's linear decision tree classifiers (stages 1-3) are used in series to refine the classification of potentially abnormal thick groups. Note that three box filters precede the stage 2 classifier 2671. These were defined because, after artifact collection that followed the design of the stage one classifier 2660, a review of feature pair values indicated that these filters could eliminate a large percentage of normal/artifact objects. Following are more detailed descriptions of the classifiers used and the number of samples used to train them. Box Filters 2658 are the first step in object classification. A series of box filters are designed to remove obvious artifacts. Features are used in pairs by the box filters, which are structured to eliminate commonly occurring artifacts that may resemble segmented groups of abnormal cells.

There are 10 box filters that are applied in six areas the number of a particular type of filter appears in parenthesis. The features mentioned in the text below will be described under "Thick Group Feature Descriptions" below.

Area box filter (1)

This filter establishes whether a potential group is larger than 1,000 pixels. Only groups of that size and larger are considered as potential thick groups. This filter is a part of the image segmenter.

Whole image feature box filters (2)

Two whole image-based boxes are used to reject all kinds of artifacts. These artifacts, called other by the algorithm, include cellular artifacts, non-cellular artifacts, and groups of normal cells that are present as thick groups.

If:

$$0 \geq -1.11 \times feature93 + 262 - feature106$$

$$0 \leq 0.05 \times feature96 + 8 - feature106$$

then the object is classified as other. If not, the object is passed to the next box filter.

Out-of-focus box filters (3)

Three out-of-focus box filters are used to eliminate any segmented objects that are not properly in focus. These out-of-focus box filters are designed to remove objects that were poorly focused during image acquisition. Since identification of out-of-focus objects is unreliable, the algorithm should not attempt to classify them. The out-of-focus filter, the cytoplasm filter, the graphite filter, and the poly filter use one object feature in combination with either a whole image feature or another object-based feature:

If:

$$0 \leq -0.0027 \times feature70 + 0.427 - feature7$$

$$0 \leq -0.185 \times feature70 + 54.7 - feature119$$

$$0 \leq 0.148 \times feature100 + 0.459 - feature8$$

then the object is classified as other. If not, the object is passed to the next box filter.

Cytoplasm box filters (2)

The algorithm uses two box filters to eliminate as many objects as possible that are cytoplasm only artifacts:

If:

$$0 \geq 27.3 \times feature98 + 218.4 - feature93$$

$$0 \leq -380 \times feature11 + 142 - feature119$$

then the object is classified as other. If not, the object is passed to the next box filter.

The graphite filter (1)

This filter removes objects that are graphite artifacts. Glass laboratory slides of Pap smears commonly contain artifacts that prove to be graphite particles left by pencils:

If:

$$0 \geq -12.2 \times feature33 + 106.11 - feature95$$

then the object is classified as other. If not, the object is passed. to the next box filter.

Poly filter

The purpose of the poly filter is to eliminate segmented objects that are polymorphonucleocytes white blood cells:

If:

$$0 \geq 0.02 \times feature96 + 8.5 - feature22$$

then the object is classified as other. If not, the object is passed to the next box filter.

Stage 1 Classifier

The stage 1 classifier is a Fisher's linear binary decision tree. The stage 1 classifier 60 is designed to separate other objects—thick groups of normal cells as well as cellular and non-cellular artifacts—from potentially abnormal groups. Stage 1's feature set consists of the following 14 features:

| feature 7   | clus_light_2_dir    |
| ----------- | ------------------- |
| feature 8   | clus_light_5_mag    |
| feature 22  | clus_edge_9_9       |
| feature 24  | clus_blur_3_3_ave   |
| feature 25  | clus_blur_3_3_sd    |
| feature 70  | cluster + brightness |
| feature 78  | plus_edge_9_9       |
| feature 79  | plus_edge_17_17     |
| feature 89  | plus_blur_15_15_sd  |
| feature 93  | high_mean           |
| feature 98  | clus_edge_2_mag     |
| feature 100 | clus_edge_5_mag     |
| feature 107 | clus_blue_3_3_ave   |
| feature 119 | image_sd            |

The features are described in Table 2.

Stage 2 Box Filters

Two pre-stage 2 box filters reject artifacts that made it through the box filters and stage 1.

The box filters are implemented by the following rules, where if the statement is true the object is rejected as artifact/normal:

$$0 \leq 0.6 \ feature102 - 1.04 - feature112$$

$$0 \leq 0.025 \ feature13 + 0.21 - feature66$$

$$0 \leq 0.025 \ feature121 + 0.099 - feature42$$

Stage 2 Classifier

The stage 2 classifier 71 is a Fisher's linear decision tree. Stage 2 uses the following 16 features:

| feature 1   | image_sd           |
| ----------- | ------------------ |
| feature 8   | clus_light_5_mag   |
| feature 30  | clus_blur_7_7_sk   |
| feature 58  | ring_blur_7_7_sk   |
| feature 66  | ring_polar_max     |
| feature 70  | plus_brightness    |
| feature 78  | plus_edge_9_9      |
| feature 79  | plus_edge_17_17    |
| feature 81  | plus_blur_3_3_sd   |
| feature 88  | plus_blur_15_15_ave |
| feature 93  | high_mean          |
| feature 104 | clus_edge_5_5      |
| feature 107 | clus_blur_3_3_ave  |
| feature 119 | image_sd           |
| feature 120 | image_sk           |
| feature 121 | image_ku           |

Stage 3 Classifier

The Stage 3 classifier 2672 is a Fisher's linear decision tree. Stage 3 uses the following 9 features:

| feature 1 | area |
| feature 12 | clus_light_3_3 |
| feature 15 | clus_edge_2_mag |
| feature 16 | clus_edge_2_dir |
| feature 19 | clus_edge_9_mag |
| feature 24 | clus_blur_3_3_ave |
| feature 32 | clus_blur_15_15_ave |
| feature 67 | ring_polar_max_45 |
| feature 93 | low_threshold |

The thick group algorithm sends its accumulated results to a 20× FOV integration algorithm. Its seven outputs are:

1. Number of objects eliminated by box filters.
2. Number of objects eliminated by the stage 1 classifier 2660.
3. Number of objects eliminated by the stage 2 classifier 2671.
4. Number of objects eliminated by the stage 3 classifier 2672.
5. Number of potentially abnormal objects that remain after stage 3.
6. A bin confidence histogram of the remaining objects, which are potentially abnormal cell groups. Confidence reflects the likelihood of an object being abnormal and, as such, ranges from 0.5 to 1.0. Each node in the decision tree is assigned a confidence value based on results during training. For example, a confidence value of 0.9 would be assigned to a given node if it were found that during training, 90 percent of the objects that terminated in that node were abnormal objects. During normal operation, if an object terminated in this node, the object would be classed as potentially abnormal, and the 5th bin in the confidence histogram (for confidence of 0.9 to 1.0) would be incremented. The range of confidence values assigned to each bin are as follows:

Bin1 0.5<=confidence<0.6

Bin2 0.6<=confidence<0.7

Bin3 0.7<=confidence<0.8

Bin4 0.8<=confidence<0.9

Bin5 0.9<=confidence<=1.0

Since only the confidence histogram is retained on a slide it is not possible to obtain the confidence assigned to any one abnormal object.

7. The invention checks to make certain that a proper return was made from the classifiers and performs a checksum to make certain that the number of objects processed is correct. Detection of an error causes an error message to be printed, the algorithm to be aborted, and a −1 returned to the algorithm dispatcher.

Thick Group Feature Library

Table 4 lists the library of features: that were used in thick group algorithm development and classifier training. Detailed descriptions of the features used by thick group processing follow Table 2. Features computed for thick groups are a subset of those computed for group objects. In the following table, feature numbers for the thick group features are cross-referenced to the feature number for the same feature used by the group processing.

The characters in the Type column indicate the feature type: o indicates an object; i indicates a whole image.

TABLE 2

Thick Group Feature Library

| Thick Group Number | Feature Name |
|---|---|
| feature 1 | Cluster area |
| feature 2 | Cluster compactness |
| feature 4 | Standard deviation of cluster intensity |
| feature 5 | Cluster brightness |
| feature 6 | Magnitude of 2 × 1 bright edge in cluster |
| feature 7 | Directional disparity of 2 × 1 bright edge in cluster |
| feature 8 | Magnitude of 5 × 1 bright edge in cluster |
| feature 9 | Directional disparity of 5 × 1 bright edge in cluster |
| feature 10 | Magnitude of 9 × 1 bright edge in cluster |
| feature 11 | Directional disparity of 9 × 1 bright edge in cluster |
| feature 12 | 3 × 3 bright edge in cluster |
| feature 13 | 9 × 9 bright edge in cluster |
| feature 14 | 17 × 17 bright edge in cluster |
| feature 15 | Magnitude of 2 × 1 dark edge in cluster |
| feature 16 | Directional disparity of 2 × 1 dark edge in cluster |
| feature 17 | Magnitude of 5 × 1 dark edge in cluster |
| feature 18 | Directional disparity of 5 × 1 dark edge in cluster |
| feature 19 | Magnitude of 9 × 1 dark edge in cluster |
| feature 20 | Directional disparity of 9 × 1 dark edge in cluster |
| feature 21 | 5 × 5 dark edge in cluster |
| feature 22 | 9 × 9 dark edge in cluster |
| feature 23 | 17 × 17 dark edge in cluster |
| feature 24 | 3 × 3 blur residue mean in cluster |
| feature 25 | 3 × 3 blur residue standard deviation in cluster |
| feature 26 | 3 × 3 blur residue skewness in cluster |
| feature 27 | 3 × 3 blur residue kurtosis in cluster |
| feature 28 | 7 × 7 blur residue mean in cluster |
| feature 29 | 7 × 7 blur residue standard deviation in cluster |
| feature 30 | 7 × 7 blur residue skewness in cluster |
| feature 31 | 7 × 7 blur residue kurtosis in cluster |
| feature 32 | 15 × 15 blur residue mean in cluster |
| feature 33 | 15 × 15 blur residue standard deviation in cluster |
| feature 34 | 15 × 15 blur residue skewness in cluster |
| feature 35 | 15 × 15 blur residue kurtosis in cluster |
| feature 36 | Polarity area in cluster |
| feature 37 | Polarity range in cluster |
| feature 38 | Polarity maximum in cluster |
| feature 39 | Polarity in maximum direction +45° in cluster |
| feature 40 | Polarity in maximum direction +90° in cluster |
| feature 41 | Polarity in maximum direction +135° in cluster |
| feature 42 | Normalized cluster brightness |
| feature 43 | Magnitude of 2 × 1 dark edge in normalized cluster |
| feature 44 | Directional disparity of 2 × 1 dark edge in normalized cluster |
| feature 45 | Magnitude of 5 × 1 dark edge in normalized cluster |
| feature 46 | Directional disparity of 5 × 1 dark edge in normalized cluster |
| feature 47 | Magnitude of 9 × 1 dark edge in normalized cluster |
| feature 48 | Directional disparity of 9 × 1 dark edge in normalized cluster |
| feature 49 | 5 × 5 dark edge in normalized cluster |
| feature 50 | 9 × 9 dark edge in normalized cluster |
| feature 51 | 17 × 17 dark edge in normalized cluster |
| feature 52 | 3 × 3 blur residue mean in normalized cluster |
| feature 53 | 3 × 3 blur residue standard deviation in normalized cluster |
| feature 54 | 3 × 3 blur residue skewness in normalized cluster |
| feature 55 | 3 × 3 blur residue kurtosis in normalized cluster |
| feature 56 | 7 × 7 blur residue mean in normalized cluster |
| feature 57 | 7 × 7 blur residue standard deviation in normalized cluster |
| feature 58 | 7 × 7 blur residue skewness in normalized cluster |
| feature 59 | 7 × 7 blur residue kurtosis in normalized cluster |
| feature 60 | 15 × 15 blur residue mean in normalized cluster |
| feature 61 | 15 × 15 blur residue standard deviation in normalized cluster |
| feature 62 | 15 × 15 blur residue skewness in normalized cluster |

TABLE 2-continued

Thick Group Feature Library

| Thick Group Number | Feature Name |
|---|---|
| feature 63 | 15 × 15 blur residue kurtosis in normalized cluster |
| feature 64 | Polarity area in ring around cluster |
| feature 65 | Polarity range in ring around cluster |
| feature 66 | Polarity maximum in ring around cluster |
| feature 67 | Polarity in maximum direction +45° in ring around cluster |
| feature 68 | Polarity in maximum direction +90° in ring around cluster |
| feature 69 | Polarity in maximum direction +135° in ring around cluster |
| feature 70 | cluster +brightness |
| feature 71 | Magnitude of 2 × 1 bright edge in cluster+ |
| feature 72 | Directional disparity of 2 × 1 dark edge in cluster+ |
| feature 73 | Magnitude of 5 × 1 dark edge in cluster+ |
| feature 74 | Directional disparity of 5 × 1 dark edge in cluster+ |
| feature 75 | Magnitude of 9 × 1 dark edge in cluster+ |
| feature 76 | Directional disparity of 9 × 1 dark edge in cluster+ |
| feature 77 | 5 × 5 dark edge in cluster+ |
| feature 78 | 9 × 9 dark edge in cluster+ |
| feature 79 | 17 × 17 dark edge in cluster+ |
| feature 80 | 3 × 3 blur residue in cluster+ |
| feature 81 | 3 × 3 blur residue standard deviation in cluster+ |
| feature 82 | 3 × 3 blur residue skewness in cluster+ |
| feature 83 | 3 × 3 blur residue kurtosis in cluster+ |
| feature 84 | 7 × 7 blur residue mean in cluster+ |
| feature 85 | 7 × 7 blur residue standard deviation in cluster+ |
| feature 86 | 7 × 7 blur residue skewness in cluster+ |
| feature 87 | 7 × 7 blur residue kurtosis in cluster+ |
| feature 88 | 15 × 15 blur residue mean in cluster+ |
| feature 89 | 15 × 15 blur residue standard deviation in cluster+ |
| feature 90 | 15 × 15 blur residue skewness in cluster+ |
| feature 91 | 15 × 15 blur residue kurtosis in cluster+ |
| feature 92 | SIL high_count variable |
| feature 93 | SIL high_mean variable |
| feature 94 | SIL medium_threshold variable |
| feature 95 | SIL low_threshold variable |
| feature 96 | FOV brightness |
| feature 97 | FOV edge |
| feature 98 | Magnitude of 2 × 1 dark edge in FOV |
| feature 99 | Directional disparity of 2 × 1 dark edge in FOV |
| feature 100 | Magnitude of 5 × 1 dark edge in FOV |
| feature 101 | Directional disparity of 5 × 1 dark edge in FOV |
| feature 102 | Magnitude of 9 × 1 dark edge in FOV |
| feature 103 | Directional disparity of 9 × 1 dark edge in FOV |
| feature 104 | 5 × 5 dark edge in FOV |
| feature 105 | 9 × 9 dark edge in FOV |
| feature 106 | 17 × 17 dark edge in FOV |
| feature 107 | 3 × 2 blur residue mean |
| feature 108 | 3 × 3 blur residue standard deviation in FOV |
| feature 109 | 3 × 3 blur residue skewness in FOV |
| feature 110 | 3 × 3 blur residue kurtosis in FOV |
| feature 111 | 7 × 7 blur residue mean in FOV |
| feature 112 | 7 × 7 blur residue standard deviation in FOV |
| feature 113 | 7 × 7 blur residue skewness in FOV |
| feature 114 | 7 × 7 blur residue kurtosis in FOV |
| feature 115 | 15 × 15 blur residue mean in FOV |
| feature 116 | 15 × 15 blur residue standard deviation in FOV |
| feature 117 | 15 × 15 blur residue skewness in FOV |
| feature 118 | 15 × 15 blur residue kurtosis in FOV |
| feature 119 | Whole image standard deviation |
| feature 120 | Whole image skewness |
| feature 121 | Whole image kurtosis |

Thick Group Feature Descriptions

The following are feature descriptions for all features that were selected from the feature library during training. They are arranged by thick group feature number (Feature 1 through Feature 121). Thick group features are cross referenced with the feature name and the feature type. Features of type "O" are based on the object segmentation mask, whereas objects of type "i" are based on the entire 20× FOV.

Feature Descriptions

| feature1 | area | O |
|---|---|---|

Feature 1 is the area, in pixels, of the cluster mask. Feature 1 is used by the stage 2 and stage 3 classifiers.

| feature7 | clus_light_2_dir | O |
|---|---|---|

Feature 7 is the 2×1 (2 pixels horizontally by 1 pixel vertically) bright edge directional disparity within the cluster. Bright edge directional disparity is a combination of two measures. Pixels are examined to find those that have darker neighbors on both sides horizontally, then those that have darker neighbors vertically. For each pixel that passes the neighbor test, the magnitude of the difference is recorded. The magnitude of differences for all horizontal pixels are summed. Then all pixels in the vertical are summed. Feature 7 is calculated as the minimum of these two values divided by the sum of the two. It provides a measure of whether there are significantly more relatively bright pixels in one direction versus the other. This feature shows whether there is some directionally dominant texture in the cluster. In this case, the texture is very fine, or of a high spatial frequency. Feature 7 is used by one of the out-of-focus box filters and by the stage 1 classifier.

| feature8 | clus_light_5_mag | O |
|---|---|---|

Feature 8 is the 5×1 bright edge magnitude. As with the directional disparity described in Feature 7, this measure is made up of two directions: horizontal and vertical. In this case, rather than looking for pixels that are surrounded by dark pixels in one direction, groups of three pixels are examined to see if they are bounded by dark pixels on both sides horizontally and vertically. Feature 8 is calculated by squaring the two measures, summing them, then taking their square root. This feature gives a measure of how much edge there is in the cluster that is about three pixels wide in either direction. It also gives a measure for the amount of texture there is that has bright spots about three pixels in size. Feature 8 is used by one of the out-of-focus box filters, and by the stage 1 and stage 2 classifiers.

| feature11 | clus_light_9_dir | O |
|---|---|---|

Feature 11 is similar to feature 7 except that groups of seven pixels are checking for dark neighbors rather than a single pixel. Feature 11 is used by the cytoplasm box filter.

| feature12 | clus_light_3_3 | O |
|---|---|---|

Feature 12 is the 3×3 bright edge strength in the cluster. The algorithm searches for pixels that have dark pixels around them in all directions. The difference between the bright pixel and its surrounding pixels are accumulated for all such pixels in the cluster. The accumulated figure is normalized by the total number of pixels in the cluster. This measures the amount of texture in each cluster that consists of bright regions about one pixel in size that are surrounded by darker pixels on all sides. Feature 12 is used by the poly box filter.

| feature13 | clus_light_9_9 | O |
|---|---|---|

Feature 13 is similar to feature 12 except that groups of pixels, 7×7 in size, are checked for darker neighbors. Feature 13 is used by the stage 2 pre-box filter.

| feature15 | clus_edge_2_mag | O |
|---|---|---|

Feature 15 is the magnitude of the 2×1 dark edge. This feature is the same as Feature 8 except that single, dark pixels are searched for rather than bright regions 3 pixels wide. This measure is of the total amount of dark area covered by single pixels bounded in two directions by bright area. Feature 15 is used by the stage 3 classifier.

| feature16 | clus_edge_2_dir | O |
|---|---|---|

Feature 16 is the directional disparity of 2×1 dark edge in cluster. The feature is similar to feature 7 with the exception that the pixels are examined to find those that have brighter neighbors. This feature is used by the stage 3 classifier.

| feature19 | clus_edge_9_mag | O |
|---|---|---|

Feature 19 is the magnitude of the 9×1 dark edge. This is the same as feature 15 except that regions of 7 pixels in width or height are searched for that have bright neighbors. This feature is used by the stage 3 classifier.

| feature22 | clus_edge_9_9 | O |
|---|---|---|

Feature 22 is 9×9 dark edge strength. This is the same as feature 12 except that pixels with brighter neighbors are searched for and the size of the dark region searched for is about 7×7. The texture this feature measures are dark spots about 4 microns on a side. Feature 22 is used by the poly box filter and by the stage 1 classifier.

| feature24 | clus_blur_3_3_ave | O |
|---|---|---|

Feature 24 is called mean 3×3 blur residue in the cluster. The algorithm measures the absolute difference between a 3×3 binomial filtered image and its original. The average pixel value of this difference is feature 24. This feature measures high spatial frequency in the cluster. Feature 24 is used by the stage 1 and stage 2 classifiers.

| feature25 | clus_blur_3_3_sd | O |
|---|---|---|

Feature 25 is the standard deviation of the 3×3 blur residue in the cluster. This measure gives some indication of how uniform high spatial frequencies are within the cluster. Feature 25 is used by the stage 1 classifier.

| feature30 | clus_blur_7_7_sk | O |
|---|---|---|

Feature 30 is the 7×7 blur residue skewness in cluster. The image is blurred using a 7×7 structure element. The difference between this and the original image is taken. The feature is the skewness of this difference in the area defined by the object mask. Feature 30 is used by the stage 2 classifier.

| feature32 | clus_blur_15_15_ave | O |
|---|---|---|

Feature 32 is the 15×15 blur residue mean in cluster. It is similar to feature 24 except that this feature uses a 15×15 structure element to perform the filtering. Feature 32 is used by the stage 3 classifier.

| feature33 | clus_blur_15_15_sd | O |
|---|---|---|

Feature 33 is similar to feature 32 except that standard deviation is computed. Feature 33 is used by the graphite box filter.

| feature42 | ring_brightn | O |
|---|---|---|

Feature 42 is the average brightness of the normalized cluster. The average intensity of the cluster is divided by the average intensity of the ring around the cluster. This ratio is average brightness. Feature 42 is used by the pre-stage 2 box filters.

| feature58 | ring_blur_7_7_sk | O |
|---|---|---|

Feature 58 is the 7×7 blur residue skewness. This is the ratio of the 7×7 blur residue skewness of the cluster to that of the ring around the cluster. This ratio indicates how texture variations compare from the cluster to the ring around the cluster. It identifies changes in texture from the cluster to the ring around the cluster. It also provides a measure of how similar the cluster is to its background when its spatial frequencies have been eliminated by a 7×7 filter. Feature 58 is used by the stage 2 classifier.

| feature66 | ring_polar_max | O |
|---|---|---|

Feature 66 is the maximum polarity in the ring around the cluster. This feature measures the amount of dark ovoid area that is within the ring around the cluster. The polarity is broken down into its maximum direction, its direction perpendicular to the maximum, and its direction to 45 degrees on either side of the maximum. Polarity in the maximum direction in the ring around the cluster gives the value for feature 66. Feature 66 is used by the pre-stage 2 box filters and by the stage 2 classifier.

| feature67 | ring_polar_max_45 | O |
|---|---|---|

Feature 67 is polarity in maximum direction plus 45 degrees in ring around cluster. Similar to feature 66 except the polarity is in the direction of the maximum plus 45 degrees. Feature 67 is used by the stage 3 classifier.

| feature70 | plus_brightness | o |
|---|---|---|

Feature 70 is cluster plus brightness. This is the average intensity of the pixels in the expanded cluster. Feature 70 is used by the stage 1 classifier.

| feature78 | plus_edge_9_9 | o |
|---|---|---|

Feature 78 is called 9×9 dark edge strength. This is the same as feature 22 except that it's calculated in the expanded cluster rather than in the cluster. Feature 78 is used by the stage 1 classifier and by the stage 2 classifier.

| feature79 | plus_edge_17_17 | o |
|---|---|---|

Feature 79 is a 17×17 dark edge in a cluster. The feature is the same as feature 78 except a 17×17 dark region is searched for. Feature 79 is used by the stage 1 and stage 2 classifiers.

| feature81 | plus_blur_3_3_sd | o |
|---|---|---|

Feature 81 is a 3×3 blur residue standard deviation in the expanded cluster. The difference between the original image and the image blurred by a 3×3 filter is taken. The feature is the standard deviation of the pixels in the expanded cluster. Feature 81 is used by the stage 2 classifier.

| feature88 | plus_blur_15_15_ave | o |
|---|---|---|

Feature 88 is 15×15 blur residue mean in the expanded cluster. The difference between the original image and the image blurred by a 15×15 filter is taken. The feature is the standard deviation of the pixels in the expanded cluster. Feature 88 is used by the stage 2 classifier.

| feature88 | plus_blur_15_15_sd | o |
|---|---|---|

Feature 89 is a 15×15 blur residue standard deviation in the expanded cluster. Similar to feature 81 except a 15×15 filer is used. Feature 89 is used by the stage 1 classifier.

| feature93 | high_mean | i |
|---|---|---|

Feature 93 is the single cell algorithm's high_mean variable measurement. This is the average value of all pixels in an image that have values between 199 and 250. This feature provides some information about an image's background. Feature 93 is used by one of the cytoplasm box filters, and by the stage 1 and stage 2 classifiers.

| feature95 | low_threshold | i |
|---|---|---|

Feature 95 is the single cell algorithm's low_threshold value. This value is calculated during single cell segmentation. It is the result of an adaptive threshold calculation for a certain range of pixel intensities in an image. It gives a measure for how much dark matter there is in an image. If the threshold is low, there is a fair amount of dark matter in the image. If the threshold is high, there are probably few high density objects in the image. Feature 95 is used by the graphite box filter and the stage 3 classifier.

| feature98 | clus_edge_2_mag | i |
|---|---|---|

Feature 98 is the magnitude of the 2×1 dark edge in an image. This feature is calculated in the same way as feature 15 except that it is calculated over the whole image. Feature 98 is used by the stage 1 classifier.

| feature100 | clus_edge_5_mag | i |
|---|---|---|

Feature 100 is the magnitude of the 5×1 dark edge in an FOV. This feature is calculated the same way as feature 15 except that dark 3-pixel regions are searched for instead of single dark pixel. Feature 100 is used by the stage 1 classifier.

| feature104 | clus_edge_5_5 | i |
|---|---|---|

Feature 104 is 5×5 dark edge strength. This feature is computed by finding 3×3 clusters of pixels that are surrounded by brighter pixels. The difference between the surrounding pixels and each pixel in the cluster is computed. This difference is accumulated for all the pixels in the cluster and normalized by the number of pixels in the whole image. The feature characterizes texture with dark spots that measure 1 to 2 microns on a side. Feature 104 is used by the stage 2 classifier.

| feature106 | clus_edge_17_17 | i |
|---|---|---|

Feature 106 is a 17×17 dark edge strength. This feature is the same as feature 104 except that the accumulation is based on clusters that are 17×17 pixels in size. Feature 106 is used by the area box filter and by two whole image box filters.

| feature107 | clus_blur_3_3_ave | i |
|---|---|---|

Feature 107 is a 3×3 blur residue mean. This is calculated the same way as feature 24 except that the feature is calculated over the entire image rather than just over the cluster. Feature 107 is used by the stage 1 and stage 2 classifiers.

| feature109 | clus_blue_3_3_sk | i |
|---|---|---|

Feature 109 is similar to feature 107 except the skewness instead of the mean is computed. Feature 109 is used by the pre-stage 2 box filters.

| feature112 | clus_blur_7_7_sd | i |

Feature 112, a blur residue using a 7×7 structure element, is computed for a whole image. Feature 112 is the standard deviation of this feature. Feature 112 is used by the pre-stage 2 box filters.

| feature119 | image_sd | i |

Feature 119 is the standard deviation for the whole image. This is tile standard deviation of the pixel values for every pixel in an image. This feature provides a measure of the amount of variation in pixel intensity across the entire 20× FOV. Feature 119 is used by one of the out-of-focus box filters, the cytoplasm box filters, and by stage 1 and stage 2 classifiers.

| feature120 | image_sk | i |

Feature 120 is the whole image skewness. This feature is the skewness of the values of every pixel in an image. It is a measure of how much pixel values are biased to one side or the other of mean pixel intensity. Skewness provides a measure of image content. Feature 120 is used by the stage 2 classifier.

| feature121 | image_ku | i |

Feature 121 is a whole image kurtosis. The feature is the 4th statistical moment or kurtosis taken on the whole image. Kurtosis provides a measure of the percentage of the population that is in the tails of the distribution. Feature 175 is used by the stage 2 classifier.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

We claim:

1. In a biological specimen examination system where biological specimen slides all originate from a selected laboratory and are scored, a method of determining at least one initial analysis score threshold comprising the steps of:
   (a) selecting a plurality of slides from a slide population from said selected laboratory as calibration slides;
   (b) scoring the calibration slides to generate a plurality of analysis scores;
   (c) determining at least one initial analysis score threshold for the selected laboratory based on an analysis of said calibration slides so as to assure that a proportion of slides are selected for review.

2. In a biological specimen examination system where biological specimen slides all originate from a selected laboratory and are scored and at least one analysis score threshold has been predetermined, a method of dynamically adjusting the at least one analysis score threshold comprising the steps of:
   (a) scoring a new slide from the selected laboratory to generate an analysis score;
   (b) dynamically adjusting the at least one analysis score threshold for the selected laboratory based on the analysis score to provide at least one adjusted analysis score threshold so as to assure that a proportion of slides are selected for review.

3. The method of claim 2 further including the step of dynamically adjusting the at least one initial analysis score threshold by dynamically updating at least one representation of a batch of slides while slide processing at least one slide.

4. The method of claim 3 wherein the at least one representation comprises at least one batch.

5. The method of claim 3, wherein each one of the at least one representation comprises an oldest slide, and wherein each batch comprises slides belonging to a chronological group, wherein the chronological group comprises either a newest group, an oldest group, or at least one intervening group, the method further including the steps of:
   (a) qualifying at least one slide as a calibration slide and placing it in the newest group;
   (b) removing the oldest slide from the oldest group;
   (c) moving the oldest slide from the newest group to a newest intervening group;
   (d) continuing to move the oldest slide from each intervening group to a next newest intervening group for all intervening groups; and
   (e) moving the oldest slide from an oldest intervening group to the oldest group.

6. The method of claim 3 wherein the at least one representation comprises a long-term batch, a mid-term batch and a short-term batch.

7. The method of claim 6 further including the steps of weighing the short-term batch by a first factor, weighing the mid-term batch by a second factor, and weighing the long-term batch by a third factor.

8. The method of claim 3, wherein the the at least one representation further comprises a long-term and a short-term batch and the long-term batch and the short-term batch include an oldest slide, further including the steps of:
   (a) qualifying at least one of the plurality of slides as a calibration slide;
   (b) removing the oldest slide from the long-term batch;
   (c) moving the oldest slide in the short-term batch to the long-term batch; and
   (d) moving the calibration slide to the short-term batch.

9. The method of claim 3 wherein the at least one representation of a batch of slides is updated dynamically for a new slide.

10. In a biological specimen examination system where biological specimen slides all originate from a selected laboratory and are scored for the selected laboratory and at least one analysis score threshold has been predetermined for the biological specimen slides, a method of dynamically adjusting the at least one analysis score threshold comprising the steps of:
    (a) scoring a new slide to generate an analysis score;
    (b) dynamically adjusting the at least one analysis score threshold for the selected laboratory based on the analysis score to provide at least one adjusted analysis score threshold for the selected laboratory; and
    (c) verifying that the at least one adjusted analysis score threshold meets a predetermined criteria.

11. The method of claim 10 further including the step of dynamically adjusting the at least one predetermined analysis score threshold further including dynamic updating of at least one representation of a batch of slides while slide processing at least one slide.

12. In a biological specimen examination system where biological specimen slides all originate from a selected laboratory and are scored for the selected laboratory, a method of dynamically adjusting at least one analysis score threshold comprising the steps of:

(a) determining at least one initial analysis score threshold for the selected laboratory based on an analysis of a plurality of calibration slides;

(b) dynamically adjusting the at least one initial analysis score threshold based on a new slide to provide at least one adjusted analysis score threshold; and (c) verifying quality of the at least one adjusted analysis score threshold.

13. The method of claim 12 wherein the biological specimen slides are biological specimens prepared by the papanicolaou method.

14. The method of claim 12 further including the steps of determining if an analysis for a selected slide score is greater than a threshold, an if it is sending the slide for review and not updating a batch and, if the analysis score is greater than a second threshold then sending the slide for review and updating the batch, otherwise considering the slide normal and updating the batch.

15. The method of claim 12 wherein the step of verifying quality of the at least one adjusted analysis score threshold, wherein calibration slides are identified and placed in long-term, mid-term, and short-term batches, further includes the steps of:

(a) recording values of Qi, Ti, and Pi(Q) corresponding to each calibration slide, where Pi(Q) is an estimated probability of a slide rejected by qualification thresholds Q's for super batch_i, where super batch_i consists of all the plurality of calibration slides in batch_i as well as all successfully analyzed slides rejected by Q within a time period covered by batch_i;

(b) determining if a calibration population matches a current slide population, by checking if Pi(Q)=QR; and (c) determining if the calibration population does not match the current slide population, and adjusting a value of Q according to a following update rule for Q:

```
IF (Pi(Q) < first portion of QR or Pi(Q) >
second portion of QR) THEN
    re-calibrate
ELSE IF (Pi(Q) < third portion of QR or Pi(Q) >
fourth portion of QR) THEN
    Qi = adjust Q
ELSE Qi = Qi–1, wherein an adjust Q process
generates a new Q.
```

16. The method of claim 15 further comprising the step of checking if the adjustment suggests that the calibration population and the current slide population are significantly different, and if so, initiating a new calibration process.

17. The method of claim 15 further including the steps of:

(a) checking if (Qi<fifth portion of $Q_0$ or Qi>sixth portion of $Q_0$) then re-calibrating; and (b) checking if (Ti<seventh portion of $T_0$ or Ti>eighth portion of $T_0$) then re-calibrating.

18. An initial calibration method for a predetermined sort application comprising the steps of:

(a) selecting a plurality of slides wherein the plurality of slides originate from a selected laboratory, comprising a first predetermined number of representative normal and a second predetermined number of representative abnormal slides from a slide population;

(b) processing the plurality of slides to generate analysis scores for each of the plurality of slides;

(c) ordering the analysis scores;

(d) setting a threshold value for the selected laboratory, where the threshold value corresponds to a first top portion of a successfully processed normal slide population to an initial qualification threshold $Q_0$, wherein an expected percentage of normal slides rejected by $Q_0$, P(R'|N), is equal to a predetermined percent;

(e) determining the percentage of abnormal slides called review, P(R'|A), by $Q_0$;

(f) setting the threshold value corresponding to a second top portion of the successfully processed normal slide population as an initial dynamic threshold $T_0$;

(g) determining a percentage of abnormal slides called review by $T_0$, as P(R''|A);

(h) setting an abnormal proportion P(A) according to the slide population statistics of a lab of interest;

(i) setting a dynamic threshold population ratio; and (j) setting an expected qualification rejection proportion.

19. The method of claim 18 wherein the slide population statistics comprise 1% for quality control applications.

20. The method of claim 18 wherein the dynamic threshold population ratio comprises a quantity D determined by the equation:

$$D = ((\text{a portion determined by subtracting the first top portion}$$
$$\text{from the second top portion}) - (1 - P(A)) + P(A)\,(P(R''|A) -$$
$$P(R'|A)))/((1 - P(R'|N))(1 - P(A)) + P(A)(1 - P(R'|A))).$$

21. The method of claim 18 wherein a qualification rejection proportion comprises a quantity QR determine by the equation:

$$QR = P(R'|N)\,(1-P(A)) + P(A)\,P(R'|A).$$

22. A method of dynamically updating a representation of at least one batch of slides while slide processing a plurality of slides wherein the plurality of slides originate from a selected laboratory, wherein each of the at least one batch of slides includes an oldest slide, and wherein each of the plurality of batches of slides contains slides belonging to a chronological group, wherein each chronological group comprises either a newest group, an oldest group, or at least one intervening group, the method further including the steps of:

(a) qualifying at least one slide as a calibration slide for the selected laboratory and placing it in the newest group;

(b) removing the oldest slide from the oldest group;

(c) moving the oldest slide from the newest group to a newest intervening group;

(d) continuing to move the oldest slide from each intervening group to a next newest intervening group for all intervening groups; and (e) moving the oldest slide from an oldest intervening group to the oldest group.

23. A method of monitoring validity of a dynamic calibration process for a biological specimen slide scoring apparatus, wherein calibration slides all originate from a selected laboratory and are identified and placed in at least one batch, the method comprising the steps of:

(a) recording values of Qi, Ti, and Pi(Q) corresponding to each calibration slide, where Pi(Q) is a weighted probability of a slide rejected by qualification thresholds Q's for super batch_i, where super batch_i comprises all the calibration slides in batch_i as well as all successfully analyzed slides rejected by Q within a time period covered by batch_i;

(b) checking if Pi(Q) equals QR to determine that a calibration population matches a current slide population for the selected laboratory; and (c) determining if the calibration population does not match the current slide population, and adjusting a value of Q according to a following update rule for Q:

IF (Pi(Q)<first portion of QR or Pi(Q)>second portion of QR) THEN
re-calibrate

ELSE IF (Pi(Q)<third portion QR or Pi(Q)>fourth portion of QR) THEN
$Q_i$=adjust Q ELSE Qi=Qi−1, wherein an adjust Q process generates a new Q based on the super batch_i.

24. The method of claim 23 further comprising the step of checking if the adjustment of step (c) suggests that the calibration population and the current slide population are significantly different, and if so, initiating a new calibration process.

25. The method of claim 23 further including the steps of:

(a) checking if (Qi<first portion of $Q_o$ or Qi>a second portion of $Q_o$) then re-calibrating; and (b) checking if (Ti<a third portion of $T_o$ or Ti>a fourth portion of $T_o$) then re-calibrating.

* * * * *

UNITED STATES PATENT AND TRADEMARK OFFICE
CERTIFICATE OF CORRECTION

PATENT NO. : 5,627,908
DATED : May 6, 1997
INVENTOR(S) : Lee et al.

It is certified that error appears in the above-identified patent and that said Letters Patent is hereby corrected as shown below:

Column 4, line 59, delete the word "tile" and replace it with -- the --.

Column 8, line 15, delete the word "raking" and replace it with -- ranking --.

Column 8, line 64, delete the symbol "$Q_i$" and replace it with -- Qi --.

Column 9, line 57, delete the word "inn" and replace it with -- in --.

Column 12, line 9, after the word "integrate" delete the word "the".

Column 12, line 67, delete the word "inn" and replace it with -- in --.

Column 13, line 35, after the word "Belmont" insert a -- , --.

Column 13, line 45, after the word "based" delete the -- , --.

Column 14, line 11, after the word "individual" delete the -- , --.

Column 17, line 33, delete the word "one" and replace it with -- of --.

Column 17, line 56, delete the word "ore" and replace it with -- of --.

Column 22, line 33, after the word "in" insert -- a --.

Column 25, line 19, delete the word "sell" and replace it with -- set --.

UNITED STATES PATENT AND TRADEMARK OFFICE
CERTIFICATE OF CORRECTION

PATENT NO. : 5,627,908

DATED : May 6, 1997

INVENTOR(S) : Lee et al.

It is certified that error appears in the above-identified patent and that said Letters Patent is hereby corrected as shown below:

Column 31, line 13, the portion of the formula reading:

$$" \sum_{Pixels} abs\bigl((I_{Orig} \ominus (3x3)) - I_{Orig}\bigr) "$$

should read $$-- \sum_{Pixels} abs\bigl((I_{Orig} \oplus (3x3)) - I_{Orig}\bigr) -- .$$

Column 33, line 45, the portion of the formula reading $" I_{Size3} = (I_{Size2} \ominus ((3x)_{Cross})) "$ should read $-- I_{Size3} = (I_{Size2} \ominus ((3x3)_{Cross})) -- .$ Column 37, line 44, delete the word "inn" and replace it with -- in --.

Column 40, line 4, after the word "segmented" delete the -- . --.

Column 41, line 58, after the word "features" delete the -- : --.

UNITED STATES PATENT AND TRADEMARK OFFICE
CERTIFICATE OF CORRECTION

PATENT NO. : 5,627,908
DATED : May 6, 1997
INVENTOR(S) : Lee et al.

It is certified that error appears in the above-identified patent and that said Letters Patent is hereby corrected as shown below:

Column 47, line 46, the portion of the formula reading "feature88" should read -- feature89 --"

Column 49, line 14, delete the word "tile" and replace it with -- the --.

Column 54, line 3, delete the symbol "$Q_i$" and replace it with -- Qi --.

Signed and Sealed this

Fifteenth Day of September, 1998

Attest:

BRUCE LEHMAN

Attesting Officer

Commissioner of Patents and Trademarks